US007994225B2

(12) United States Patent
Bostian et al.

(10) Patent No.: US 7,994,225 B2
(45) Date of Patent: *Aug. 9, 2011

(54) BACTERIAL EFFLUX PUMP INHIBITORS FOR THE TREATMENT OF OPHTHALMIC AND OTIC INFECTIONS

(75) Inventors: Keith Bostian, Atherton, CA (US); Tomasz Glinka, Cupertino, CA (US); Olga Lomovskaya, Mill Valley, CA (US); Mark Surber, San Diego, CA (US); Neil Berkley, San Diego, CA (US); David Griffith, San Marcos, CA (US)

(73) Assignee: Rempex Pharmaceuticals, Inc., San Diego, CA (US)

( * ) Notice: Subject to any disclaimer, the term of this patent is extended or adjusted under 35 U.S.C. 154(b) by 909 days.

This patent is subject to a terminal disclaimer.

(21) Appl. No.: 11/856,657

(22) Filed: Sep. 17, 2007

(65) Prior Publication Data

US 2008/0132457 A1 Jun. 5, 2008

Related U.S. Application Data

(63) Continuation-in-part of application No. 11/082,745, filed on Mar. 16, 2005.

(60) Provisional application No. 60/554,143, filed on Mar. 17, 2004, provisional application No. 60/564,916, filed on Apr. 22, 2004, provisional application No. 60/845,749, filed on Sep. 18, 2006, provisional application No. 60/858,510, filed on Nov. 13, 2006.

(51) Int. Cl.
*A61K 31/13* (2006.01)
*A61K 31/155* (2006.01)

(52) U.S. Cl. .................. 514/638; 514/631; 514/636

(58) Field of Classification Search .................. 514/631, 514/636, 638
See application file for complete search history.

(56) References Cited

U.S. PATENT DOCUMENTS

| | | | |
|---|---|---|---|
| 4,324,794 A | 4/1982 | Tidwell et al. | |
| 4,397,863 A | 8/1983 | Tidwell et al. | |
| 4,619,942 A | 10/1986 | Tidwell et al. | |
| 4,823,784 A | 4/1989 | Bordoni et al. | |
| 4,853,416 A | 8/1989 | Anaebonam et al. | |
| 4,895,719 A | 1/1990 | Radhakrishnan et al. | |
| 4,933,347 A | 6/1990 | Tidwell et al. | |
| 4,963,589 A | 10/1990 | Tidwell et al. | |
| 5,049,389 A | 9/1991 | Radhakrishnan | |
| 5,084,480 A | 1/1992 | Pai et al. | |
| 5,089,527 A | 2/1992 | Lord | |
| 5,162,361 A * | 11/1992 | Rosenthal et al. | 514/396 |
| 5,202,320 A | 4/1993 | Tidwell et al. | |
| 5,204,113 A | 4/1993 | Hartley et al. | |
| 5,206,236 A | 4/1993 | Tidwell et al. | |
| 5,262,157 A | 11/1993 | Bernard et al. | |
| 5,334,374 A | 8/1994 | Hartley et al. | |
| 5,355,872 A | 10/1994 | Riggs et al. | |
| 5,364,615 A | 11/1994 | Debs et al. | |
| 5,366,726 A | 11/1994 | Debs et al. | |
| 5,428,051 A | 6/1995 | Tidwell et al. | |
| 5,474,759 A | 12/1995 | Fassberg et al. | |
| 5,485,827 A | 1/1996 | Zapol et al. | |
| 5,521,189 A | 5/1996 | Boykin et al. | |
| 5,534,496 A | 7/1996 | Lee et al. | |
| 5,556,637 A | 9/1996 | Hager et al. | |
| 5,597,573 A | 1/1997 | Kamireddy et al. | |
| 5,602,172 A | 2/1997 | Boykin et al. | |
| 5,606,058 A | 2/1997 | Boykin et al. | |
| 5,622,955 A | 4/1997 | Boykin et al. | |
| 5,627,184 A | 5/1997 | Boykin et al. | |
| 5,668,166 A | 9/1997 | Tidwell et al. | |
| 5,668,167 A | 9/1997 | Tidwell et al. | |
| 5,674,911 A | 10/1997 | Emanuele et al. | |
| 5,686,456 A | 11/1997 | Boykin et al. | |
| 5,723,495 A | 3/1998 | Hall et al. | |
| 5,725,871 A | 3/1998 | Illum | |
| 5,741,517 A | 4/1998 | Hager et al. | |
| 5,770,585 A | 6/1998 | Kaufman et al. | |
| 5,843,980 A | 12/1998 | Hall et al. | |
| 5,869,091 A | 2/1999 | Carter et al. | |
| 5,873,359 A | 2/1999 | Zapol et al. | |
| 5,989,832 A | 11/1999 | Trias et al. | |
| 6,008,247 A | 12/1999 | Boykin et al. | |
| 6,025,398 A | 2/2000 | Hall et al. | |
| 6,076,522 A | 6/2000 | Dwivedi et al. | |
| 6,098,619 A | 8/2000 | Britto et al. | |
| 6,114,310 A | 9/2000 | Chamberland et al. | |
| 6,123,924 A | 9/2000 | Mistry et al. | |
| 6,126,919 A | 10/2000 | Stefely et al. | |

(Continued)

FOREIGN PATENT DOCUMENTS

EP 0345926 8/1991

(Continued)

OTHER PUBLICATIONS

Definition of prevent, Oxford English Dictionary, http://dictionary.oed.com/, accessed online on May 27, 2010.*
Shepp et al. J. Acquired Immune Deficiency Syndromes, 1994, 7(8), p. 823-831.*
Dropulic et al. J. Infectious Diseases, 1995, 171(4), p. 930-937.*
Anne, et al., "Antifungal and antibacterial activities of diarylamidine derivatives," *Antimicrobial Agents and Chemotherapy*, 18(2), 231-9.
Baucheron, et al., "The AcrB Multidrug Transporter Plays a Major Role in High-Level Fluoroquinolone Resistance in *Salmonella enterica* Serovar Typhimurium Phage Type DT204," *Microbial Drug Resistance*, vol. 8, 2002, 281-289.

(Continued)

*Primary Examiner* — Shaojia Anna Jiang
*Assistant Examiner* — Jonathan Lau
(74) *Attorney, Agent, or Firm* — Knobbe, Martens, Olson & Bear LLP

(57) ABSTRACT

Efflux pump inhibitors are co-administered with antimicrobial agents for the treatment of ophthalmic or otic infections. The agents may be co-administered directly to the site of infection (e.g., the eye or ear).

17 Claims, 13 Drawing Sheets

U.S. PATENT DOCUMENTS

| | | | |
|---|---|---|---|
| 6,127,554 | A | 10/2000 | Boykin et al. |
| 6,172,104 | B1 | 1/2001 | Tidwell et al. |
| 6,180,604 | B1 | 1/2001 | Fraser et al. |
| 6,204,279 | B1 | 3/2001 | Leger et al. |
| 6,214,883 | B1 | 4/2001 | Hall et al. |
| 6,245,746 | B1 | 6/2001 | Chamberland et al. |
| 6,309,623 | B1 | 10/2001 | Weers et al. |
| 6,326,395 | B1 | 12/2001 | Tidwell et al. |
| 6,346,391 | B1 | 2/2002 | Oethinger et al. |
| 6,362,229 | B1 | 3/2002 | Markham et al. |
| 6,399,629 | B1 | 6/2002 | Chamberland et al. |
| 6,416,742 | B1 | 7/2002 | Stefely et al. |
| 6,423,737 | B2 | 7/2002 | Hall et al. |
| 6,436,980 | B1 | 8/2002 | Leger et al. |
| 6,486,200 | B1 | 11/2002 | Boykin et al. |
| 6,503,881 | B2 | 1/2003 | Krieger et al. |
| 6,503,940 | B2 | 1/2003 | Boykin et al. |
| 6,538,106 | B1 | 3/2003 | Fraser et al. |
| 6,553,987 | B1 | 4/2003 | Davies |
| 6,613,787 | B2 | 9/2003 | Wilson et al. |
| 6,635,668 | B1 | 10/2003 | Tidwell et al. |
| 6,641,800 | B1 | 11/2003 | Mistry et al. |
| 6,649,652 | B2 | 11/2003 | Boykin et al. |
| 6,677,133 | B2 | 1/2004 | Oethinger et al. |
| 6,720,003 | B2 | 4/2004 | Chen et al. |
| 7,026,136 | B2 | 4/2006 | Oethinger et al. |
| 7,037,495 | B1 | 5/2006 | Burnie et al. |
| 7,056,917 | B2 | 6/2006 | Nakayama et al. |

FOREIGN PATENT DOCUMENTS

| | | |
|---|---|---|
| EP | 0309519 | 7/1992 |
| EP | 0383680 | 12/1992 |
| WO | WO 96/40117 | 12/1996 |
| WO | WO 99/37667 | 7/1999 |
| WO | WO 02/09758 A2 | 2/2002 |

OTHER PUBLICATIONS

Bichowsky-Slomnitzki L, "Inhibitory Action of Diamidines and Stimulative Effect of Polyamines on Enzymatic Activites of *Escherichia coli* and *Micrococcus aureus*," *Arch. Biochem.*, Jul. 1950, 27(2):294-303.

Bichowsky-Slomnitzki L, "The Effect of Aromatic Diamidines on Bacterial Growth," *J. Bact.* 1948, 55:27-31.

Chauhan, et al., "Synthesis of 2,7-diamidinoxanthone, thioxanthone and related compounds as potential leishmanicides," *Indian J. of Chem., Section B: Organic Chemistry Including Medicinal Chemistry*, 26B(3), 248-50.

Dave R., et al. Amino Acids, 24, 2003, 245-261.

Delia, et al., "Ring-based analogues of pentamidine versus *P. carinii* pneumonia in culture," *Bioorganic & Medicinal Chemistry Letters*, 1996, vol. 6, 2367-2370.

Donkor IO et al., "In vitro antimicrobial activity of aromatic diamidines and diimidazolines related to pentamidine," *Eur. J. Med. Chem.* 34 (1999) 639-643.

Donkor, et al., "Trypanocidal Activity of Conformationally Restricted Pentamidine Congeners," *J. Med. Chem.*, (2003) 46, 1041-1048.

Donkor, et al., "In vitro antimicrobial activity of aromatic diamidines and diimidazolines related to pentamidine," *Eur. J. Med. Chem.* (1999) 34, 639-643.

Donkor, et al., "Pentamidine Congeners. 2. 2-Butene-Bridged Aromatic Diamidines and Diimidazolines as Potential Anti-*Pneumocystis carinii* Pneumonia Agents," *J. Med. Chem.* 1994, 37, 4554-4557.

Feddersen, A., et al., "Experimental studies on the nephrotoxicity of pentamidine in rats," *Journal of Antimicrobial Chemotherapy*, 1991, 28, 437-446.

Goodman & Gilman's: The Pharmacological Basis of Therapeutics, 10th Edition, McGraw-Hill Medical Publishing Division, 2001, pp. 54-56.

Helweg-Larsen et al., "*Pneumocystic carnii* Pneumonia," *Current Treatment Options in Infectious Diseases*, (2002) 4:363-375.

Hicks, MR, "The Effect of Isoniazid, Carbutamide, Propamidine and Pentamidine on the Transaminases and Growth of *Escherichia coli*, Strain 15, Mutant M2," *Biochimica Et Biophysica Acta*, 1961, 46:143-151.

Hsieh P-C et al., "Bacteria lacking a multidrug pump: A sensitive tool for drug discovery," *Proc. Natl. Acad. Sci.*, Jun. 1998, 95:6602-6606.

International Search Report and Written Opinion from International Application No. PCT/US2005/008873, mailed Jun. 26, 2007.

Invitation to Pay Additional Fees dated Mar. 2, 2007, received in International Application No. PCT/US2005/008873.

Jennings, F.W., "Effect of Tetracycline Administration on the Efficacy of Diminazene Aceturate Therapy . . . ", *Research in Veterinary Science*, 1987, 43, pp. 173-176.

Jones, et al., "Novel Pentamidine Analogs in the Treatment of Experimental *Pneumocystis carinii* Pneumonia," *Antimicrobial Agents and Chemotherapy*, Jun. 1990, pp. 1026-1030.

Kaatz, "Inhibition of bacterial efflux pumps: a new strategy to combat increasing antimicrobial agent resistance," *Expert Opin. Emerging Drugs* 7 (2002) 223-233.

Kohn HI, "The Effect of Propamidine on Bacterial Growth," *Science*, 98(2540):224.

Levy, "Active Efflux Mechanisms for Antimicrobial Resistance," *Antimicrobial Agents and Chemotherapy*, 36(4), 695-703.

Lewis JD et al., "Cephalosporin-pentamidine isethionate incompatibilities," *Am. J. Health-Syst. Pharm.*, Jun. 15, 1996, 53:1461-1462.

Libman, "Antistaphylococcal Activity of Pentamidine," *Antimicrobial Agents and Chemotherapy*, Sep. 1990, 1795-1796.

Lomovskaya, et al., "Identification and Characterization of Inhibitors of Multidrug Resistance Efflux Pumps in *Pseudomonas aeruginosa*: Novel Agents for Combination Therapy," *Antimicrobial Agents and Chemotherapy*, 2001, p. 105-116.

Lomovskaya, et al., "Inhibition of Efflux Pumps as a Novel Approach to Combat Drug Resistance in Bacteria," *J. Mol. Microbiol. Biotechnol.*, 2001, 3(2):225-236.

Mitchell BA et al., "QacA Multidrug Efflux Pump from *Staphylococcus aureus*: Comparative Analysis of Resistance to Diamidines, Biguanidines, and Guanylhydrozones," *Antimicrobial Agents and Chemotherapy*, Feb. 1998:475-477.

Mitchell, et al. Antimicrobial Agents and Chemotherapy, 1993, 475-477.

Munoz-Bellido, et al., "Antimicrobial activity of psychotropic drugs Selective serotonin reuptake inhibitors," *International Journal of Antimicrobial Agents*, 14 (2000) 177-180.

Mustafa, "Aerosolized pentamidine for the Prevention of *Pneumocystis carinii* Pneumonia in Children with Cancer Intolerant or Allergic to Trimethoprim/Sulfamethoxazole," *Journal of Clinical Oncology*, Feb. 1994, vol. 12, No. 2, pp. 258-261.

Neyfakh, "The Mutlidrug Efflux Transporter of *Bacillus subtilis* Is a Structural and Functional Homolog of the Staphylococcus NorA Protein," *Antimicrobial Agents and Chemotherapy*, 36(2), 484-485.

Neyfakh, et al., "Fluoroquinolone Resistance Protein NorA of *Staphylococcus aureus* Is a Multidrug Efflux Transporter," *Antimicrobial Agents and Chemotherapy*, 37(1), 128-129.

Poeta, et al., "In vitro antifungal activities of a series of dication-substituted carbazoles, furans, and benzimidazoles," *Antimicrobial Agents and Chemotherapy*, 42(10), 2503-2510.

Renau, et al., "Addressing the Stability of C-Capped Dipeptide Efflux Pump Inhibitors that Potentiate the Activity of Levofloxacin in *Pseudomonas aeruginosa*," *Bioorganic & Medicinal Chemistry Letters*, 11 (2001) 663-667.

Renau, et al., "Conformationallly-Restricted Analogues of Efflux Pump Inhibitors that Potentiate the Activity of Levofloxacin in *Pseudomonas aeruginosa*," *Bioorg. Med. Chem. Lett.* 13 (2003) 2755-2758.

Sands, M et al., "Pentamidine: A Review," *Reviews of Infectious Disesases*, 1985, 7(5): 625-634.

Tidwell, et al., "Analogues of 1,5-Bis(4-amidinophenoxy)pentane (Pentamidine) in the Treatment of Experimental *Pneumocystis carinii* Pneumonia," *J. Med. Chem.* 1990, 33, 1252-1257.

Tidwell, et al., "Development of Pentamidine Analogues as New Agents for the Treatment of *Pneumocystis carinii* Pneumonia," *Annals of the New York Academy of Sciences*, 1990, vol. 616, pp. 421-441.

Webster's Collegiate Dictionary, 1993, p. 1096.

Yeh, et al., Pharmaceutical Research, vol. 13(4), 1996, 628-632.

Office Action dated Jul. 23, 2007, received in U.S. Appl. No. 11/082,745.

Fastier et al., "Circulatory Properties of iso-Thioureas, Guanidines, iso-Ureas and Amidines," *Journal of Pharmacology and Experimental Therapeutics*, (1947) 89(3): 256-270.

Southan et al. "Amidines are potent inhibitors of nitric oxide synthases: preferential inhibition of the inducible isoform," *European Journal of Pharmacology Molecular Pharmacology Section*, (1995) 291(3): 311-318.

Decker et al. "Pneumonia due to *Bordetella bronchiseptica* in a Patient with AIDS," *Review of Infectious Diseases*, (1991) 13(6): 1250-1251.

Wien et al., "Diamidines as antibacterial compounds," *Brit. J. Pharmacol.*, (1948) 3, 211-218.

Rodnick et al. "Diagnosis and antibiotic treatment of community-acquired pneumonia," *West J. Med* 1991, 154, p. 405-409.

Tumbarello et al. "Bacterial Pneumonia in HIV-Infected Patients: Analysis of Risk Factors and Prognostic Indicators," *Journal of Acquired Immune Deficiency Syndromes and Human Retrovirology*, (1998) 18(1): 39-45.

Join-Lambert et al. "Differential Selection of Multidrug Efflux Mutants by Trovafloxacin and Ciprofloxacin in an Experimental Model of *Pseudomonas aeruginosa* Acute Pneumonia in Rats," *Antimicrobial Agents and Chemotherapy*, 2001, 45(2) 571-576.

Definition of prophylaxis, WordNet, http://wordnet.princeton.edu, accessed online Feb. 12, 2009.

Definition of prevent, Wordnet, http://wordnet.princeton.edu, accessed online Nov. 14, 2007.

\* cited by examiner

BACTERIAL EFFLUX PUMP INHIBITORS FOR THE TREATMENT OF OPHTHALMIC AND OTIC INFECTIONS

RELATED APPLICATIONS

This application is a continuation-in-part of U.S. application Ser. No. 11/082,745, filed Mar. 16, 2005, which claims the benefit of U.S. Provisional Application Nos. 60/554,143, filed Mar. 17, 2005 and 60/564,916, filed Apr. 22, 2004. This application also claims the benefit of U.S. Provisional Application Nos. 60/845,749, filed Sep. 18, 2006 and 60/858,510, filed Nov. 13, 2006. All of the foregoing applications are incorporated herein by reference in their entirety.

BACKGROUND OF THE INVENTION

1. Field of the Invention

This invention relates to the field of antimicrobial agents and more specifically it relates to the use of pentamidine and analogous compositions as efflux pump inhibitors to be co-administered with antimicrobial agents for the treatment of infections caused by drug resistant pathogens. The invention also includes novel compounds useful as efflux pump inhibitors and compositions and devices comprising an efflux pump inhibitor and an antimicrobial agent.

2. Description of the Related Art

Antibiotics have been effective tools in the treatment of infectious diseases during the last half-century. From the development of antibiotic therapy to the late 1980s there was almost complete control over bacterial infections in developed countries. However, in response to the pressure of antibiotic usage, multiple resistance mechanisms have become widespread and are threatening the clinical utility of antibacterial therapy. The increase in antibiotic resistant strains has been particularly common in major hospitals and care centers. The consequences of the increase in resistant strains include higher morbidity and mortality, longer patient hospitalization, and an increase in treatment costs.

Bacteria have developed several different mechanisms to overcome the action of antibiotics. These mechanisms of resistance can be specific for a molecule or a family of antibiotics, or can be non-specific and be involved in resistance to unrelated antibiotics. Several mechanisms of resistance can exist in a single bacterial strain, and those mechanisms may act independently or they may act synergistically to overcome the action of an antibiotic or a combination of antibiotics. Specific mechanisms include degradation of the drug, inactivation of the drug by enzymatic modification, and alteration of the drug target. There are, however, more general mechanisms of drug resistance, in which access of the antibiotic to the target is prevented or reduced by decreasing the transport of the antibiotic into the cell or by increasing the efflux of the drug from the cell to the outside medium. Both mechanisms can lower the concentration of drug at the target site and allow bacterial survival in the presence of one or more antibiotics that would otherwise inhibit or kill the bacterial cells. Some bacteria utilize both mechanisms, combining a low permeability of the cell wall (including membranes) with an active efflux of antibiotics.

In recent years interest in efflux-mediated resistance in bacteria has been triggered by the growing amount of data implicating efflux pumps in clinical isolates. The phenomenon of antibiotic efflux was first discovered in 1980, in the context of the mechanism of tetracycline resistance in enterobacteria. Since then, it has been shown that efflux of antibiotics can be mediated by more than one pump in a single organism, and that almost all antibiotics are subject to resistance by this mechanism.

Some efflux pumps selectively extrude specific antibiotics. Examples of such pumps include the Tet or CmlA transporters, which can extrude tetracycline or chloramphenicol, respectively. Other efflux pumps, so-called multi-drug resistance (MDR) pumps, extrude a variety of structurally diverse compounds. In the latter case, a single efflux system may confer resistance to multiple antibiotics with different modes of action. In this respect, bacterial MDR pumps are similar to mammalian MDR transporters. In fact, one such pump, P-glycoprotein, the first discovered MDR pump, confers multiple drug resistance on cancer cells and is considered to be one of the major reasons tumor resistance to anti-cancer therapy. A typical example of bacterial MDR pump is MexAB-OprM from *Pseudomonas aeruginosa*. This pump has been shown to affect the susceptibility of the organism to almost all antibiotic classes which fluoroquinolones, β-lactams, macrolides, phenicols, tetracyclines, and oxazolidinones.

Efflux pumps in gram-positive bacteria excrete their substrates across a single cytoplasmic membrane. This is also the case for some pumps in gram-negative bacteria, and as a result their substrates are effluxed into the periplasmic space. Other efflux pumps from gram-negative bacteria efflux their substrates directly into the external medium, bypassing the periplasm and the outer membrane. These pumps are organized in complex three component structures, which traverse both inner and outer membranes. They consist of a transporter located in the cytoplasmic membrane, an outer membrane channel and a periplasmic 'linker' protein, which brings the other two components into contact. It is clearly advantageous for gram-negative bacteria to efflux drugs by bypassing the periplasm and outer membrane. In gram-negative bacteria the outer membrane significantly slows down the entry of both lipophilic and hydrophilic agents. The former, such as erythromycin and fusidic acid, are hindered by the lipopolysaccharide components of the outer leaflet of the outer membrane bilayer. Hydrophilic agents cross the outer membrane through water-filled porins whose size prevents rapid diffusion, even for small compounds such as fluoroquinolones and some β-lactams. Thus, direct efflux creates the possibility for two different mechanisms to work synergistically to provide the cell with a potent defense mechanism. Furthermore, direct efflux into the medium leads to decreased amounts of drugs not only in the cytoplasmic but also in the periplasmic space. This could explain the apparently paradoxical finding that efflux pumps protect gram-negative bacteria from β-lactam antibiotics whose target penicillin-binding proteins are found in the periplasm.

Many MDR pumps are encoded by the genes, which are normal constituents of bacterial chromosomes In this case increased antibiotic resistance is a consequence of over-expression of these genes. Thus bacteria have the potential to develop multi-drug resistance without the acquisition of multiple specific resistance determinants. In some cases, the simultaneous operation of efflux pumps and other resistance mechanisms in the same cell results in synergistic effects.

While some genes encoding efflux pumps are not expressed in wild type cells and require induction or regulatory mutations for expression to occur, other efflux genes are expressed constitutively. As a result wild type cells have basal level of efflux activity. This basal activity of multi-drug efflux pumps in wild type cells contribute to intrinsic antibiotic resistance, or more properly, decreased antibiotic susceptibility. This intrinsic resistance may be low enough for the bacteria to still be clinically susceptible to therapy. However, the bacteria might be even more susceptible if efflux pumps were rendered non-functional, allowing lower doses of antibiotics to be effective. To illustrate, *P. aeruginosa* laboratory-derived mutant strain PAM1626, which does not produce any measurable amounts of efflux pump is 8 to 10 fold more susceptible to levofloxacin and meropenem than the parent strain *P. aeruginosa* PAM1020, which produces the basal level of MexAB-OprM efflux pump. Were it not for efflux pumps, the spectrum of activity of many so-called 'gram-positive' antibiotics could be expanded to previously non-susceptible gram-negative species. This can be applied to 'narrow-spectrum' β-lactams, macrolides, lincosamides, streptogramins, rifamycins, fusidic acid, and oxazolidinones—all of which have a potent antibacterial effect against engineered mutants lacking efflux pumps.

It is clear that in many cases, a dramatic effect on the susceptibility of problematic pathogens would be greatly enhanced if efflux-mediated resistance were to be nullified. Two approaches to combat the adverse effects of efflux on the efficacy of antimicrobial agents can be envisioned: identification of derivatives of known antibiotics that are not effluxed and development of therapeutic agents that inhibit transport activity of efflux pumps and could be used in combination with existing antibiotics to increase their potency.

There are several examples when the first approach has been successfully reduced to practice. These examples include new fluoroquinolones, which are not affected by multidrug resistance pumps in *Staphylococcus aureus* or *Streptococcus pneumonia* or new tetracycline and macrolide derivatives which are not recognized by the corresponding antibiotic-specific pumps. However, this approach appears to be much less successful in the case of multidrug resistance pumps from gram-negative bacteria. In gram-negative bacteria, particular restrictions are imposed on the structure of successful drugs: they must be amphiphilic in order to cross both membranes. It is this very property that makes antibiotics good substrates of multi-drug resistance efflux pumps from gram-negative bacteria. In the case of these bacteria the efflux pump inhibitory approach becomes the major strategy in improving the clinical effectiveness of existing antibacterial therapy.

The efflux pump inhibitory approach was first validated in the case of mammalian P-glycoprotein. And the first inhibitors have been found among compounds with previously described and quite variable pharmacological activities. For example, P-glycoprotein-mediated resistance, can be reversed by calcium channel blockers such as verpamyl and azidopine, immunosuppressive agents cyclosporin A and FK506 as well as antifungal agents such as rapamycin and FK520 (Raymond et al, 1994). It is important that efflux pump inhibitory activity was by no means connected to other activities of these compounds. In fact, the most advanced inhibitor of P-glycoprotein is a structural derivative of cyclosporin A and is devoid if immunosuppressive activity.

Improved compositions and methods for controlling drug resistance in microbes, in particular in microbes that are highly resistant to drugs, would be of tremendous benefit. The present invention provides such compositions and methods.

SUMMARY OF THE INVENTION

It has been discovered that pentamidine is capable of inhibiting multidrug-resistance pumps from various gram-negative bacteria. When administered to a patient suffering from a microbial infection that employs efflux pump(s) as a resistance mechanism, pentamidine inhibits the activity of the pump(s) allowing a co-administrated antimicrobial agent to accumulate in sufficient concentration to inhibit the microbe and treat the infection. Thus, in one aspect the present invention relates to a method for inhibiting a microbial infection that employs an efflux pump resistance mechanism, comprising contacting the cell with an efflux pump inhibitor optionally in combination with an antimicrobial agent. The efflux pump inhibitor may be pentamidine or a structurally related compound.

In a further related aspect, this invention includes a method for prophylactic treatment of a mammal. In this method, an efflux pump inhibitor is administered to a mammal at risk of a microbial infection, e.g., a bacterial infection. In some embodiments, an antimicrobial agent is administered in combination with or coadministered with the efflux pump inhibitor.

This invention also features a method of enhancing the antimicrobial activity of an antimicrobial agent against a microbe, in which such a microbe is contacted with an efflux pump inhibitor, and an antibacterial agent.

In a further aspect this invention provides pharmaceutical compositions effective for treatment of an infection of an animal, e.g., a mammal, by a microbe, such as a bacterium or a fungus. The composition includes a pharmaceutically acceptable carrier and an efflux pump inhibitor as described above. The invention also provides antimicrobial formulations that include an antimicrobial agent, an efflux pump inhibitor, and a carrier. In preferred embodiments, the antimicrobial agent is an antibacterial agent.

In a further aspect the efflux pump inhibitor is administered to the lungs as an aerosol. The antimicrobial agent may be administered in conjunction with the efflux pump inhibitor by any known means. Finally, the present invention includes not only a large number of known compounds that are now disclosed as useful as efflux pump inhibitors, but also includes a large number of novel compounds with that utility, and those new compounds comprise one aspect of the present invention.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

In one embodiment, a method is provided for treating a bacterial infection in a subject, including co-administering to a subject infected with a bacteria an antimicrobial agent and a compound of formula I in such a manner as to achieve an effective efflux pump inhibitory concentration of the compound of formula I at a site of infection:

wherein $R_1$ and $R_2$ are separately selected from the group consisting of hydrogen, methyl, amine, and $C_{1-4}$ alkylamine;

linkers $L_1$ and $L_3$ are separately selected from the group consisting of amine, $C_{1-2}$ alkyl, and $C_{1-2}$ alkylamine or are separately absent;

aromatic rings $A_1$ and $A_2$ are separately selected from the group consisting of

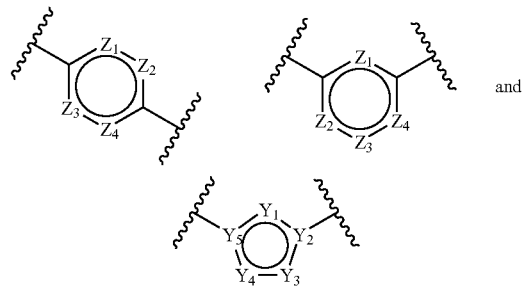

wherein $Z_1$-$Z_4$ are separately selected from the group consisting of C and N, with the proviso that aromaticity of the aromatic rings are maintained;

$Z_1$-$Z_4$ that are C are optionally substituted with $C_{1-4}$ alkyl, $CH_2NH_2$, halogen, methoxy, $CH_2C(O)NMe_2$, $C(O)NH_2$, $C(O)NMe_2$, $SO_2Me$, or $SO_2NH_2$;

$Z_1$-$Z_4$ that are N are optionally quaternized to form

$Y_1$, $Y_3$, and $Y_4$ are separately selected from the group consisting of CH, N, NH, S, and O and $Y_2$ and $Y_5$ are separately selected from the group consisting of C and N, with the proviso that aromaticity of the aromatic rings are maintained;

$Y_1$, $Y_3$, and $Y_4$ that are C are optionally substituted with halogen, methoxy, $CH_2C(O)NH_2$, $CH_2C(O)NMe_2$, $C(O)NMe_2$, $SO_2Me$, or $SO_2NH_2$;

$Y_1$, $Y_3$, and $Y_4$ that are N are optionally quaternized to form

wherein $R_3$ is $C_{1-4}$ alkyl, $CH_2C(O)NH_2$, or $CH_2C(O)NMe_2$;

linker $L_2$ is a 1 to 12 unit chain optionally containing units selected from the group consisting of $CH_2$, $C(CH_3)_2$, O, C(O), S, S(O), $S(O)_2$, NH, $NR_4$, =N—, phenyl, monocyclic 5-membered heteroaryl, monocyclic 6-membered heteroaryl, —CH=CH— cis, —CH=CH— trans, NHC(O)NH, $NR_4C(O)NH$, $NHC(O)NR_4$, $NR_4C(O)NR_4$, OC(O)NH, $NR_4C(O)O$, $OC(O)NR_4$, and NHC(O)O with the proviso that $L_2$ does not contain a C(O)NH, $C(O)NR_4$, C(O)O, or C(O)S unit;

wherein the 5-membered heteroaryls are selected from the group consisting of imidazole, furane, thiophene, thiazole, isothiazole, oxazole, isoxazole, 1,2,3-oxadiazole, 1,3,4-oxadiazole, 1,2,4-oxadiazole, 1,2,3-triazole, 1,3,4-triazole, 1,2,3-thiazole, 1,3,4-thiazole, and 1,2,4-thiazole;

the 6-membered heteroaryls are selected from the group consisting of pirydine, pirymidyne, pirydazine, 1,2,4-triazine, and 1,3,5-triazine; and $R_4$ is selected from the group consisting of H and $C_{1-4}$ alkyl.

In some embodiment, the method further includes identifying the subject as a subject infected with a bacteria that is resistant to the antimicrobial agent. In some embodiments, the method further includes identifying the subject as a subject infected with a bacteria that is capable of developing resistance to the antimicrobial agent. In some embodiments, the resistance is at least partly efflux pump-mediated. In some embodiments, the efflux pump inhibitory concentration is sufficient to overcome or suppress the emergence of efflux pump-mediated resistance in the bacteria.

In another embodiment, a method is provided for prophylactic treatment of a subject, including co-administering to a subject at risk of infection with a bacteria an antimicrobial agent and a compound of formula I in such a manner as to achieve an efflux pump inhibitory concentration of the compound of formula I as described above at a potential site of infection. In one embodiment, the method further includes identifying the subject as a subject at risk of the bacterial infection.

In another embodiment, a method is provided for treating a microbial infection in a subject, including administering to a subject infected with a microbe a compound of formula I as described above in such a manner as to achieve an efflux pump inhibitory concentration of the compound of formula I at a site of infection, with the proviso that the compound of formula I does not include pentamidine, propamindine, hexamidine, dibromopropamidine, phenamidine, amicarbalide, diaminazene, and stilbamidine. In one embodiment, the method further comprising identifying the subject as a subject infected with a microbe that is resistant to an antimicrobial agent. In one embodiment, the method further includes identifying the subject as a subject infected with a microbe that is capable of developing resistance to an antimicrobial agent. In one embodiment, the microbe is a bacteria. One embodiment further includes co-administering with the compound of formula I an antimicrobial agent. In one embodiment, the antimicrobial agent is an antibacterial agent. In one embodiment, the MIC of the compound of formula I for the microbe is greater than about 32 µg/ml.

In another embodiment, a method is provided for prophylactic treatment of a subject, comprising administering to a subject at risk of infection with a microbe a compound of formula I as described above in such a manner as to achieve an efflux pump inhibitory concentration of the compound of formula I at a site of infection, with the proviso that the compound of formula I does not include pentamidine, propamindine, hexamidine, dibromopropamidine, phenamidine, amicarbalide, diaminazene, and stilbamidine. In one embodiment, the method further includes identifying the subject as a subject at risk of the microbial infection. In one embodiment, the microbe is a bacteria. In one embodiment, the method further includes co-administering with the compound of formula I an antimicrobial agent. In one embodiment, the antimicrobial agent is an antibacterial agent. In one embodiment, the MIC of the compound of formula I for the microbe is greater than about 32 µg/ml.

In some embodiments of the methods described above, an effective efflux pump inhibitory concentration of the compound of formula I remains at the site of infection for at least about a 2 hour period. In some embodiments of the methods described above, an effective efflux pump inhibitory concentration of the compound of formula I remains at the site of infection for at least about 4 hour period. In some embodiments of the methods described above, an effective efflux pump inhibitory concentration of the compound of formula I is at the site of infection at a same time as the antimicrobial agent is present at its peak period. In some embodiments of the methods described above, an effective efflux pump inhibitory concentration of the compound of formula I is at the site of infection for at least about 25% of the time the antimicrobial agent is present at its peak period. In some embodiments of the methods described above, the effective efflux pump inhibitory concentration is sufficient to improve an AUC/MIC ratio of the antimicrobial agent by at least about 25%. In some embodiments of the methods described above, the effective efflux pump inhibitory concentration is sufficient to improve time-above-MIC for the antimicrobial agent by at least about 25%. In some embodiments of the methods described above, the effective efflux pump inhibitory concentration is sufficient to cause a therapeutic effect. In some embodiments of the methods described above, the site of infection is localized. In some embodiments of the methods described above, the bacteria is a *Pseudomonas*. In some embodiments of the methods described above, the administering step comprises administering the antimicrobial agent and the compound of formula I in a predetermined ratio. In some embodiments of the methods described above, the administering step comprises administering the antimicrobial agent and the compound of formula I by separate routes of administration. In some embodiments of the methods described above, the antimicrobial agent and the compound of formula I are administered sequentially. In some embodiments of the methods described above, the antimicrobial agent and the compound of formula I are administered simultaneously. In some embodiments of the methods described above, the antimicrobial agent and the compound of formula I are administered in a combined, fixed dosage form. In some embodiments of the methods described above, the antimicrobial agent is a substrate of an efflux pump in the bacteria. In some embodiments of the methods described above, the antimicrobial agent is an antibacterial agent. In some embodiments of the methods described above, the antimicrobial agent is a quinolone. In some embodiments of the methods described above, the antimicrobial agent is a fluoroquinolone. In some embodiments of the methods described above, the antimicrobial agent is selected from the group consisting of ciprofloxacin, enoxacin, gatifloxacin, gemifloxacin, levofloxacin, lomefloxacin, moxifloxacin, norfloxacin, ofloxacin, pefloxacin, sparfloxacin, garenoxacin, sitafloxacin, and DX-619. In some embodiments of the methods described above, the antimicrobial agent is selected from the group consisting of an aminoglycoside, beta-lactam, coumermycin, chloramphenical, daptomycin, glycopeptide, glycylcycline, ketolide, macrolide, oxazolidonone, rifamycin, stroptogramin and tetracycline. In some embodiments of the methods described above, the bacteria is a gram-negative bacteria. In some embodiments of the methods described above, the bacteria is selected from the group consisting of *Pseudomonas aeruginosa, Pseudomonas fluorescens, Pseudomonas acidovorans, Pseudomonas alcaligenes, Pseudomonas putida, Stenotrophomonas maltophilia, Burkholderia cepacia, Aeromonas hydrophilia, Escherichia coli, Citrobacter freundii, Salmonella typhimurium, Salmonella typhi, Salmonella paratyphi, Salmonella enteritidis, Shigella dysenteriae, Shigella flexneri, Shigella sonnei, Enterobacter cloacae, Enterobacter aerogenes, Klebsiella pneumoniae, Klebsiella oxytoca, Serratia marcescens, Francisella tularensis, Morganella morganii, Proteus mirabilis, Proteus vulgaris, Providencia alcalifaciens, Providencia rettgeri, Providencia stuartii, Acinetobacter calcoaceticus, Acinetobacter haemolyticus, Yersinia enterocolitica, Yersinia pestis, Yersinia pseudotuberculosis, Yersinia intermedia, Bordetella pertussis, Bordetella parapertussis, Bordetella bronchiseptica, Haemophilus influenzae, Haemophilus parainfluenzae, Haemophilus haemolyticus, Haemophilus parahaemolyticus, Haemophilus ducreyi, Pasteurella multocida, Pasteurella haemolytica, Branhamella catarrhalis, Helicobacter pylori, Campylobacter fetus, Campylobacter jejuni, Campylobacter coli, Borrelia burgdorferi, Vibrio cholerae, Vibrio parahaemolyticus, Legionella pneumophila, Listeria monocytogenes, Neisseria gonorrhoeae, Neisseria meningitidis, Kingella, Moraxella, Gardnerella vaginalis, Bacteroides fragilis, Bacteroides distasonis, Bacteroides* 3452A homology group, *Bacteroides vulgatus, Bacteroides ovalus, Bacteroides thetaiotaomicron, Bacteroides uniformis, Bacteroides eggerthii*, and *Bacteroides splanchnicus*. In some embodiments of the methods described above, the subject is a human.

In another embodiment, a pharmaceutical product is provided including a fixed combination of an antimicrobial agent and a compound of formula I as described above. In one such embodiment, the antimicrobial and the compound of formula I are physically combined. In one embodiment, the antimicrobial and the compound of formula I are packaged together in separate containers. In one embodiment, the antimicrobial agent is a substrate of an efflux pump in a bacteria. In one embodiment, the antimicrobial is an antimicrobial used to treat infections caused by a gram negative bacteria. In one embodiment, the antimicrobial is an antimicrobial used to treat infections caused by one or more bacteria selected from the group consisting of *Pseudomonas aeruginosa, Pseudomonas fluorescens, Pseudomonas acidovorans, Pseudomonas alcaligenes, Pseudomonas putida, Stenotrophomonas maltophilia, Burkholderia cepacia, Aeromonas hydrophilia, Escherichia coli, Citrobacter freundii, Salmonella typhimrium, Salmonella typhi, Salmonella paratyphi, Salmonella enteritidis, Shigella dysenteriae, Shigella flexneri, Shigella sonnei, Enterobacter cloacae, Enterobacter aerogenes, Klebsiella pneumoniae, Klebsiella oxytoca, Serratia marcescens, Francisella tularensis, Morganella morganii, Proteus mirabilis, Proteus vulgaris, Providencia alcalifaciens, Providencia rettgeri, Providencia stuartii, Acinetobacter calcoaceticus, Acinetobacter haemolyticus, Yersinia enterocolitica, Yersinia pestis, Yersinia pseudotuberculosis, Yersinia intermedia, Bordetella pertussis, Bordetella parapertussis, Bordetella bronchiseptica, Haemophilus influenzae, Haemophilus parainfluenzae, Haemophilus haemolyticus, Haemophilus parahaemolyticus, Haemophilus ducreyi, Pasteurella multocida, Pasteurella haemolytica, Branhamella catarrhalis, Helicobacter pylori, Campylobacter fetus, Campylobacter jejuni, Campylobacter coli, Borrelia burgdorferi, Vibrio cholerae, Vibrio parahaemolyticus, Legionella pneumophila, Listeria monocytogenes, Neisseria gonorrhoeae, Neisseria meningitidis, Kingella, Moraxella, Gardnerella vaginalis, Bacteroides fragilis, Bacteroides distasonis, Bacteroides* 3452A homology group, *Bacteroides vulgatus, Bacteroides ovalus, Bacteroides thetaiotaomicron, Bacteroides uniformis, Bacteroides eggerthii*, and *Bacteroides splanchnicus*. In one embodiment, the antimicrobial is an antimicrobial used to treat infections caused by a bacteria that comprises an efflux pump that is inhibited by the compound of formula I. In one embodiment, the antimicrobial and the compound of formula I have a molar ratio equal to or greater than about 1 part compound of formula I to about 1 part antimicrobial.

In another embodiment, a pharmaceutical composition is provided that includes a solution of a compound of formula I as described above having an osmolality from about 200 mOsmol/kg to about 500 mOsmol/kg. In one such embodiment, the solution has a permeant ion concentration from about 50 mM to about 250 mM.

In another embodiment, a pharmaceutical composition is provided that includes a solution of a compound of formula I having a permeant ion concentration from about 50 mM to about 250 mM. In one such embodiment, one or more permeant ions in the composition are selected from the group consisting of chloride and bromide.

In one embodiment of the methods, products, systems, and compositions described above, $R_1$ and $R_2$ in the compound of formula I are amine groups. In one embodiment of the methods, products, systems, and compositions described above, $L_2$ in the compound of formula I is a 1 to 12 unit chain containing units selected from the group consisting of —$CH_2$—, —$C(CH_3)_2$—, —O—, —C(O)—, —S—, —S(O)—, —CH=CH— cis, and —CH=CH— trans. In one embodiment of the methods, products, systems, and compositions described above, the compound of formula I is selected from the group consisting of pentamidine, propamidine, hexamidine, dibromopropamidine,

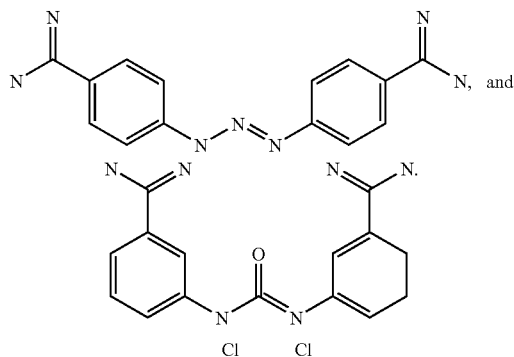

In another embodiment, a method of treating or preventing a microbial infection in an eye of a subject is provided, comprising co-administering to the eye an antimicrobial agent and a compound of formula I. In one embodiment, the compound is propamidine. One embodiment includes a kit comprising a solution of a compound of formula I, a solution of an antimicrobial agent, and an eye dropper.

In one embodiment, a pharmaceutical formulation is provided comprising propamidine and an antimicrobial agent.

In another embodiment, a method of treating or preventing a microbial infection in an ear of a subject is provided, comprising co-administering to the ear an antimicrobial agent and a compound of formula I. One embodiment includes a kit comprising a solution of a compound of formula I, a solution of an antimicrobial agent, and an ear dropper.

It is to be understood that both the foregoing general description and the following detailed description are exemplary and explanatory only and are not restrictive of the invention, as claimed.

DETAILED DESCRIPTION OF THE PREFERRED EMBODIMENT

Definitions

Figure 1A:
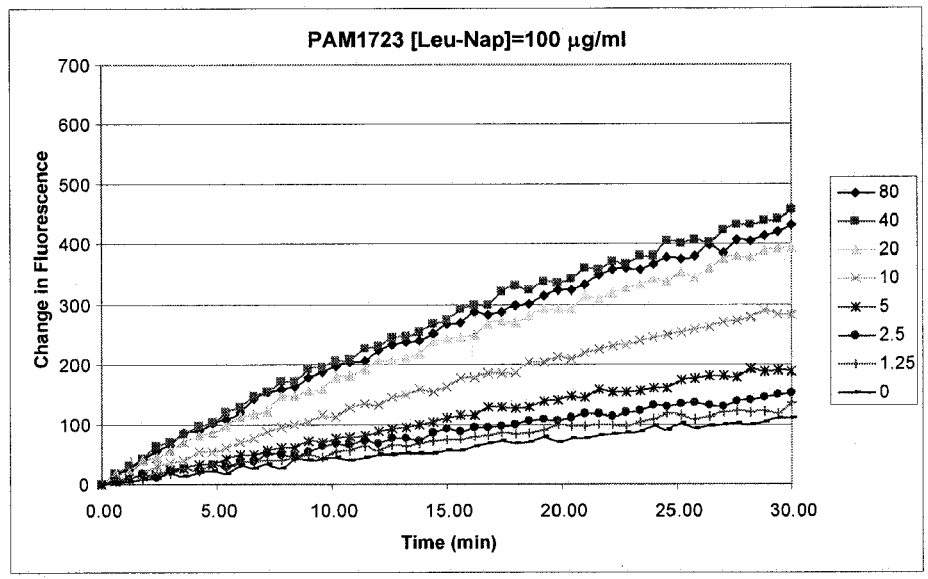
FIG. 1A illustrates the effect of pentamidine on uptake of Leu-Nap in *P. aeruginosa* PAM 1723 cells.

The term "administration" or "administering" refers to a method of giving a dosage of an antimicrobial pharmaceutical composition to a vertebrate or invertebrate, including a mammal, a bird, a fish, or an amphibian, where the method is, e.g., intrarespiratory, topical, oral, intravenous, intraperitoneal, or intramuscular. The preferred method of administration can vary depending on various factors, e.g., the components of the pharmaceutical composition, the site of the potential or actual bacterial infection, the microbe involved, and the severity of an actual microbial infection.

A "carrier" or "excipient" is a compound or material used to facilitate administration of the compound, for example, to increase the solubility of the compound. Solid carriers include, e.g., starch, lactose, dicalcium phosphate, sucrose, and kaolin. Liquid carriers include, e.g., sterile water, saline, buffers, non-ionic surfactants, and edible oils such as oil, peanut and sesame oils. In addition, various adjuvants such as are commonly used in the art may be included. These and other such compounds are described in the literature, e.g., in the Merck Index, Merck & Company, Rahway, N.J. Considerations for the inclusion of various components in pharmaceutical compositions are described, e.g., in Gilman et al. (Eds.) (1990); *Goodman and Gilman's: The Pharmacological Basis of Therapeutics,* 8th Ed., Pergamon Press.

A "diagnostic" as used herein is a compound, method, system, or device that assists in the identification and characterization of a health or disease state. The diagnostic can be used in standard assays as is known in the art.

The term "efflux pump" refers to a protein assembly that exports substrate molecules from the cytoplasm or periplasm of a cell, in an energy dependent fashion. Thus an efflux pump will typically be located in the cytoplasmic membrane of the cell (spanning the cytoplasmic membrane). In Gram-negative bacteria the pump may span the periplasmic space and there may also be portion of the efflux pump, which spans the outer membrane.

An "efflux pump inhibitor" ("EPI") is a compound that specifically interferes with the ability of an efflux pump to export its normal substrate, or other compounds such as an antibiotic. The inhibitor may have intrinsic antimicrobial (e.g., antibacterial) activity of its own, but at least a significant portion of the relevant activity is due to the efflux pump inhibiting activity.

"High throughput screening" as used herein refers to an assay that provides for multiple candidate agents or samples to be screened simultaneously. As further described below, examples of such assays may include the use of microtiter plates which are especially convenient because a large number of assays can be carried out simultaneously, using small amounts of reagents and samples.

The term "mammal" is used in its usual biological sense. Thus, it specifically includes humans, cattle, horses, dogs, and cats, but also includes many other species.

The term "microbial infection" refers to the invasion of the host organism, whether it be a vertebrate, invertebrate, fish, plant, bird, or mammal by pathogenic microbes. This includes the excessive growth of microbes that are normally present in or on the body of a mammal or other organism. More generally, a microbial infection can be any situation in which the presence of a microbial population(s) is damaging to a host mammal. Thus, a mammal is "suffering" from a microbial infection when excessive numbers of a microbial population are present in or on a mammal's body, or when the effects of the presence of a microbial population(s) is damaging the cells or other tissue of a mammal. Specifically, this description applies to a bacterial infection. Note that the present invention is also useful in treating microbial growth or contamination of cell cultures or other media, or inanimate surfaces or objects, and nothing herein should limit the present invention only to treatment of higher organisms, except when explicitly so specified in the claims.

The term "multidrug resistance pump" refers to an efflux pump that is not highly specific to a particular antibiotic. The term thus includes broad substrate pumps (efflux a number of compounds with varying structural characteristics). These pumps are different from pumps, which are highly specific individual antibiotics. Examples include tetracycline-specific efflux pumps, chloramphenicol-specific efflux pumps or macrolide-specific efflux pumps. Such efflux pumps are involved in resistance to specific antibiotics in bacteria. However, they do not confer resistance to other antibiotics. The genes for the specific pump components are found in plasmids in Gram-negative as well as in Gram-positive bacteria.

The term "pentamidine efflux pump inhibitor" refers to pentamidine, a metabolite of pentamidine, or a combination of pentamidine and one or more of its metabolites, including single steroisomers, mixtures of steroisomers and the pharmaceutically acceptable salts, and solvates thereof.

The term "pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

The term "pharmaceutically acceptable salt" refers to salts that retain the biological effectiveness and properties of the compounds of this invention and, which are not biologically or otherwise undesirable. In many cases, the compounds of this invention are capable of forming acid and/or base salts by virtue of the presence of amino and/or carboxyl groups or groups similar thereto. Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese, aluminum, and the like; particularly preferred are the ammonium, potassium, sodium, calcium and magnesium salts. Organic bases from which salts can be derived include, for example, primary, secondary, and tertiary amines, substituted amines including naturally occurring substituted amines, cyclic amines, basic ion exchange resins, and the like, specifically such as isopropylamine, trimethylamine, diethylamine, triethylamine, tripropylamine, and ethanolamine.

"Solvate" refers to the compound formed by the interaction of a solvent and pentamidine, a metabolite, or salt thereof. Suitable solvates are pharmaceutically acceptable solvates including hydrates.

"Subject" as used herein, means a human or a non-human mammal, e.g., a dog, a cat, a mouse, a rat, a cow, a sheep, a pig, a goat, a non-human primate or a bird, e.g., a chicken, as well as any other vertebrate or invertebrate.

In the context of the response of a microbe, such as a bacterium, to an antimicrobial agent, the term "susceptibility" refers to the sensitivity of the microbe for the presence of the antimicrobial agent. So, to increase the susceptibility means that the microbe will be inhibited by a lower concentration of the antimicrobial agent in the medium surrounding the microbial cells. This is equivalent to saying that the microbe is more sensitive to the antimicrobial agent. In most cases the minimum inhibitory concentration (MIC) of that antimicrobial agent will have been reduced.

By "therapeutically effective amount" or "pharmaceutically effective amount" is meant an amount of an efflux pump inhibitor, or amounts individually of an efflux pump inhibitor and an antimicrobial agent, as disclosed for this invention, which have a therapeutic effect. The doses of efflux pump inhibitor and antimicrobial agent which are useful in combination as a treatment are therapeutically effective amounts. Thus, as used herein, a therapeutically effective amount means those amounts of efflux pump inhibitor and antimicrobial agent which, when used in combination, produce the desired therapeutic effect as judged by clinical trial results and/or model animal infection studies. In particular embodiments, the efflux pump inhibitor and antimicrobial agent are combined in pre-determined proportions and thus a therapeutically effective amount would be an amount of the combination. This amount and the amount of the efflux pump inhibitor and antimicrobial agent individually can be routinely determined by one of skill in the art, and will vary, depending on several factors, such as the particular microbial strain involved and the particular efflux pump inhibitor and antimicrobial agent used. This amount can further depend upon the patient's height, weight, sex, age and medical history. For prophylactic treatments, a therapeutically effective amount is that amount which would be effective to prevent a microbial infection.

A "therapeutic effect" relieves, to some extent, one or more of the symptoms of the infection, and includes curing an infection. "Curing" means that the symptoms of active infection are eliminated, including the elimination of excessive members of viable microbe of those involved in the infection. However, certain long-term or permanent effects of the infection may exist even after a cure is obtained (such as extensive tissue damage).

"Treat," "treatment," or "treating," as used herein refers to administering a pharmaceutical composition for prophylactic and/or therapeutic purposes. The term "prophylactic treatment" refers to treating a patient who is not yet infected, but who is susceptible to, or otherwise at risk of, a particular infection. The term "therapeutic treatment" refers to administering treatment to a patient already suffering from an infection. Thus, in preferred embodiments, treating is the administration to a mammal (either for therapeutic or prophylactic purposes) of therapeutically effective amounts of a pentamidine and an antibacterial (or antimicrobial) agent in combination (either simultaneously or serially).

As used herein, an "effective efflux pump inhibitory concentration" refers to the minimal concentration of the efflux pump inhibitor sufficient to achieve at least 25% of either maximum biochemical effect (MBE) or maximum potentiating effect (MPE) in vitro. In some embodiments, an effective efflux pump inhibitory concentration sufficient to achieve at least a 25%, 40%, 50%, 60%, 70%, 80%, 90%, or 100% of either maximum biochemical effect (MBE) or maximum potentiating effect (MPE) in vitro is provided. The theoretical maximum effect that an efflux pump inhibitor can have on a microorganism is a reduction in the level of activity of the pump to a level that is equivalent to that observed in otherwise identical strains that lack all of the efflux pumps for a particular substrate. As used herein, the "MBE" is the maximum measurable biochemical effect an inhibitor can have on the efflux pump activity for a substrate. This level can be equal to or less than the theoretical maximum effect. As used herein, the "MPE" is the maximum potentiating effect that an efflux pump inhibitor can have on activity of an antimicrobial agent against the microorganism. A potentiating effect is the increase in susceptibility of a microorganism to an antimicrobial agent in the presence of an efflux pump inhibitor. The MPE can be equal to or less than the theoretical maximum potentiating effect, which is the ratio in antimicrobial susceptibility of otherwise identical strains that either possess or lack all of the efflux pumps for the antimicrobial agent.

MBE may be determined in whole-cell uptake experiments. The rate of uptake of an efflux pump substrate (antibacterial agent or non-antibiotic substrate) into intact cells of each type may be determined. To determine the rate of uptake, cells may be incubated with an efflux pump substrate, equal samples may be removed at different times and the amount of the substrate inside cells may be determined at each time point. The rate of uptake is defined as an amount of the substrate accumulated inside cells per time unit. This determination of intracellular concentration is facilitated if the substrate is fluorescent or radioactive. Otherwise, substrate can be extracted out of cells and its amount determined using HPLC. Alternatively, the rate of uptake can be monitored continuously in real time if the intracellular and extracellular substrate has different fluorescence or absorbance. One example is ethidium bromide, which upon entry inside cells binds to DNA and becomes intensely fluorescent. Another example is Leu-β-naphtylamide, which is not fluorescent in solution but upon entry into cells undergoes hydrolysis and produces highly fluorescent β-naphtylamine.

The rate of uptake is affected by both the rate of entry inside the cell and the rate of efflux. Since the rate of entry is the same for both cell types, the difference in uptake rates reflects the difference in efflux activity. The ratio between the rates of antibiotic uptake of two strains is determined and defined as a maximum biochemical effect (MBE).

The MPE may be determined in a standard checkerboard assay (e.g., Antimicrobial Combinations. In Antibiotics in Laboratory Medicine, Ed. Victor Lorian, M.D., Fourth edition, 1996, pp 333-338) using broth microdilution method as recommended by the NCCLS (National Committee for Clinical Laboratory Standards (NCCLS))). In this assay, multiple dilutions of two drugs, namely an antibiotic and efflux pump inhibitor, may be tested, alone and in combination for their ability to inhibit bacterial growth. As a result, MIC of the pump expressing strain (defined as the lowest concentration of antibiotics, within the combination, at which the visible growth of the organism is completely inhibited) is determined in the presence of each concentration of inhibitor. Increasing concentrations of inhibitor result in a reduction of MIC determined without inhibitor until the maximum antibiotic potentiating effect is achieved. Ratio of MIC without inhibitor and in the presence of inhibitor concentration, which achieves maximum reduction in MIC may be determined and is defined as MPE.

In some embodiments, an effective efflux inhibitory concentration is high enough to elicit a therapeutic effect when an efflux pump inhibitor is combined with an antimicrobial agent. As used herein, a "therapeutic effect" is defined as a statistically significant reduction in bacterial load in a host, emergence of resistance, or improvement in infection symptoms as measured by human clinical results or animal studies.

Pharmacokinetics (PK) is concerned with the time course of antimicrobial concentration in the body. Pharmacodynamics (PD) is concerned with the relationship between pharmacokinetics and the antibiotic efficacy in vivo. PK/PD parameters correlate antibiotic exposure with antibiotic activity. The rate of killing by antibiotic is dependent on antibiotic mode of action and is determined by either the length of time necessary to kill (time-dependent) or the effect of increasing concentrations (concentration-dependent). Accordingly, to predict the therapeutic efficacy of antibiotics with diverse mechanisms of action different PK/PD parameters may be used.

"AUC/MIC ratio" is one example of a PK/PD parameter. AUC is defined as the area under the plasma or site-of-infection concentration-time curve of an antimicrobial agent in vivo (in animal or human). AUC/MIC ratio is determined by dividing the 24-hour-AUC for an individual antimicrobial by the MIC for the same antimicrobial determined in vitro. Activity of antibiotics with the dose-dependent killing (such as fluoroquinolones) is well predicted by the magnitude of the AUC/MIC ratio.

"Time above MIC" (T>MIC) is another PK/PD parameter. It is expressed a percentage of a dosage interval in which the plasma or site-of-infection level exceeds the MIC. Activity of antibiotics with the time-dependent killing (such as beta-lactams or oxazolidinones) is well predicted by the magnitude of the AUC/MIC ratio.

The term "dosing interval" refers to the time between administrations of the two sequential doses of a pharmaceutical's during multiple dosing regimens. For example, in the case of ciprofloxacin, which is administered twice daily (traditional regimen of 400 mg b.i.d) and levofloxacin, which is administered once a day (500 mg or 750 mg q.d.), the dosing intervals are 12 hours and 24 hours, respectively.

As used herein, the "peak period" of a pharmaceutical's in vivo concentration is defined as that time of the pharmaceutical dosing interval when the pharmaceutical concentration is not less than 50% of its maximum plasma or site-of-infection concentration. In some embodiments, "peak period" is used to describe an interval of antimicrobial dosing.

The "respirable delivered dose" is the amount of drug inhaled during the inspiratory phase of the simulator that is equal to or less than 5 microns using a breath simulator programmed to the European Standard pattern of: 15 breaths per minute, with an inspiration to expiration ratio of 1:1.

As used herein, "co-administer" means that first and second compounds or compositions are administered to a patient such that both the first and second compound or composition may be found in the patient's bloodstream at the same time and/or at the site of infection at the same time, regardless of when the compounds are actually administered, including simultaneously or sequentially.

Methods of Efflux Pump Inhibition

In one embodiment, methods are provided for treating microbial infections by administering one or more efflux pump inhibitors disclosed herein. The efflux pump inhibitors may be administered in such a manner that an effective efflux pump inhibitory concentration of the efflux pump inhibitor is achieved at a site of infection. In some embodiments, an antimicrobial agent is co-administered with the efflux pump inhibitor. In one advantageous embodiment, the pharmacokinetics of the efflux pump inhibitor and a co-administered antimicrobial agent are substantially the same. In some advantageous embodiments, the efflux pump inhibitor concentration at a site of infection inhibits the efflux pump of the microbial to an extent such that the co-administered antimicrobial agent has an increased intracellular concentration within the microbial than it would have if the efflux pump inhibitor were not present. Thus, in some embodiments, the effective MIC of the anti-microbial is decreased by the presence of the efflux pump inhibitor.

In some embodiments, efflux pump inhibitors disclosed herein are used to prevent infection with a microbial by administering the inhibitor to a subject at risk of infection with the microbial. In such cases, the efflux pump inhibitors may be administered in such a manner that an efflux pump inhibitory concentration of the efflux pump inhibitor is achieved at a potential site of infection.

In some embodiments, an effective efflux pump inhibitory concentration is maintained at a site of infection for at least about a 1 hour period, a 2 hour period, a 3 hour period, a 4 hour period, a 5 hour period, a 6 hour period or during the entire antimicrobial agent's dosing interval. In some embodiments, an effective efflux pump inhibitor concentration is present at a site of infection at the same time that an antimicrobial agent is present at its peak period. In some embodiments, the entire period during which an effective efflux pump inhibitory concentration exists at a site of infection during an efflux pump inhibitor dosing interval is contained within an antimicrobial agent's peak period. In other embodiments, at least about 25%, 50%, or 75% of the entire period during which an effective efflux pump inhibitory concentration exists at a site of infection during an efflux pump inhibitor dosing interval is contained within an antimicrobial agent's peak period.

In some embodiments, the microbial is a bacteria and the antimicrobial agent is an antibacterial agent. In some embodiments, the patient is not otherwise in need of pentamidine therapy; i.e., is not suffering from a condition for which pentamidine therapy is approved or commonly administered. In most cases, this means that the patient is not an immunocompromised patient, or is not infected with *pneumocystis carnii* or does not have *pneumocystis carnii* pneumonia. In other embodiments, the patient is further not suffering from leishmaniasis or trypanosomiasis.

Pentamidine

Pentamidine is currently used for the treatment of *Pneumocystis carinii, Leishmania donovani, Trypanosoma brucei, T. gambiense*, and *T. rhodesiense* infections. The structure of pentamidine is

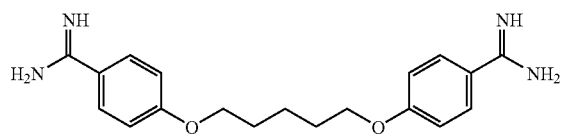

It is commercially available and formulated for injection or inhalation. For injection, pentamidine is packaged as a non-pyrogenic, lyophilized product. After reconstitution, it is administered by intramuscular or intravenous injection.

Pentamidine is formulated as the isethionate salt, which is a white, crystalline powder soluble in water and glycerin and insoluble in ether, acetone, and chloroform. It is chemically designated 4,4'-diamidino-diphenoxypentane di(β-hydroxyethanesulfonate). The molecular formula is $C_{23}H_{36}N_4O_{10}S_2$ and the molecular weight is 592.68.

The antimicrobial mode of action of pentamidine is not fully understood. In vitro studies with mammalian tissues and the protozoan *Crithidia oncopelti* indicate that the drug interferes with nuclear metabolism, producing inhibition of the synthesis of DNA, RNA, phospholipids, and proteins.

In vitro inhibitory activity of pentamidine against *Pneumocystis carini*, is 0.3 µg/ml ("Highly active anti-*Pneumocystis carinii* compounds in a library of novel piperazine-linked bisbenzamidines and related compounds", Cushion et al., *Antimicrob. Agents Chemother.*, 48(11): 4209-16, 2004; "Novel bisbenzamidines as potential drug candidates for the treatment of *Pneumocystis carinii* pneumonia", Vanden Eynde et al., *Bioorg. Med. Chem. Lett.*, 14(17): 4545-8, 2004, both of which are incorporated herein by reference in their entirety). When pentamidine is administered as a slow IV infusion (1-2 hours) at a daily dose of 3 mg/kg, the peak serum concentration ranges from 0.5 to 3.4 µg/ml ("Effect of Gender and Race on the Pharmacokinetics of Pentamidine in HIV-Infected Patients", Conte et al., *Clinical Drug Investigation*, 17 (4): 293-299, 1999, which is incorporated herein by reference in its entirety). Plasma levels decrease rapidly during the first two hours following an intravenous infusion of pentamidine isethionate to one-twentieth of peak levels, followed by a much slower decline. After 3 weeks of daily administration of 3 mg/kg dose of pentamidine, trough plasma concentration reached 61.1+/−56.0 ng/mL ("Intravenous or inhaled pentamidine for treating *Pneumocystis carinii* pneumonia in AIDS. A randomized trial", Conte et al., *Ann. Intern. Med.*, 113(3): 203-9, 1990, which is incorporated herein by reference in its entirety). In seven patients treated with daily i.m. doses of pentamidine at 4 mg/kg for 10 to 12 days, plasma concentrations were between 0.3 and 0.5 µg/mL. The patients continued to excrete decreasing amounts of pentamidine in urine up to six to eight weeks after cessation of the treatment. Systemic absorption during aerosolized therapy is minimal: peak plasma concentrations are found to be less than 5% than that observed following equivalent intravenous administration. Accumulation in the plasma does not occur with repeated inhalation as has been described with multiple intravenous dosing ("Concentrations of aerosolized pentamidine in bronchoalveolar lavage, systemic absorption, and excretion", Conte et al., *Antimicrob Agents Chemother.* 32(10): 1490-3, 1988, which is incorporated herein by reference in its entirety).

Higher pulmonary concentrations of pentamidine are observed during aerosol administration. Specifically, 24 hours after administration of 300 mg in a jet nebulizer, pentamidine concentration in bronchial alveolar lavage fluid supernatant and sediment was 23.2+/−7.75 ng/ml and 705+/−242 ng/ml, respectively ("Selective delivery of pentamidine to the lung by aerosol", Montgomery et al., *Am. Rev. Respir. Dis.*, 137(2):477-8, 1988, which is incorporated herein by reference in its entirety). The currently approved pentamidine aerosol delivery device (300 mg in a Respirgard II nebulizer) provides a mean total pulmonary deposition of nebulized pentamidine of 15.3 mg, which is 5.1% of the initial nebulizer dose ("Disposition of nebulized pentamidine measured using the direct radiolabel 123I-iodopentamidine", O'Doherty et al., *Nucl. Med. Commun.*, 14(1):8-11, 1993, which is incorporated herein by reference in its entirety). Due to the particle size created by the Respirgard II nebulizer, it is believed that the delivery of aerosolized pentamidine is mostly in the alveoli.

Surprisingly, it has been discovered that pentamidine is an efflux pump inhibitor and thus can be used in accordance with the methods described herein. Notably, it is has been discovered that the efflux pump inhibitory concentration of pentamidine is greater than the in vivo concentration of pentamidine produced by currently approved delivery methods. Specifically, concentrations of 10 μg/ml to 20 μg/ml pentamidine has been shown effective to potentiate levofloxacin against resistant bacteria in vitro. Accordingly, in one embodiment, a novel method is provided that includes co-administering pentamidine and an antimicrobial agent in such a manner as to provide an efflux pump inhibitory concentration at a site of infection in order to enhance the efficacy of the antimicrobial agent.

In some embodiments, pentamidine metabolites are provided for use as efflux pump inhibitors. Pentamidine is rapidly metabolized in the body to at least seven primary metabolites. Some of these metabolites share one or more activities with pentamidine.

Seven pentamidine metabolites are shown below.

Pentamidine Analogs

Compounds that are structurally related to pentamidine may also be used as described herein. In some embodiments, these compounds have the structure of formula (I):

$$R_1 \underset{NH}{\overset{NH}{\bigvee}} L_1 - A_1 - L_2 - A_2 - L_3 \underset{}{\overset{NH}{\bigvee}} R_2 \quad (I)$$

wherein $R_1$ and $R_2$ are separately selected from the group consisting of hydrogen, methyl, amine, and $C_{1-4}$ alkylamine; linkers $L_1$ and $L_3$ are separately selected from the group consisting of amine, $C_{1-2}$ alkyl, and $C_{1-2}$ alkylamine or are separately absent; aromatic rings $A_1$ and $A_2$ are separately selected from the group consisting of $Z_1$-$Z_4$ are separately selected from the group consisting of C and N, with the proviso that aromaticity of the aromatic rings are maintained; $Z_1$-$Z_4$ that are C are optionally substituted with $C_{1-4}$ alkyl, $CH_2NH_2$, halogen, methoxy, $CH_2C(O)NMe_2$, $C(O)NH_2$, $C(O)NMe_2$, $SO_2Me$, or $SO_2NH_2$; $Z_1$-$Z_4$ that are N are optionally quaternized to form

$Y_1$, $Y_3$, and $Y_4$ are separately selected from the group consisting of CH, N, NH, S, and O and $Y_2$ and $Y_5$ are separately selected from the group consisting of C and N, with the proviso that aromaticity of the aromatic rings are maintained; $Y_1$, $Y_3$, and $Y_4$ that are C are optionally substituted with halogen, methoxy, $CH_2C(O)NH_2$, $CH_2C(O)NMe_2$, $C(O)NMe_2$, $SO_2Me$, or $SO_2NH_2$; $Y_1$, $Y_3$, and $Y_4$ that are N are optionally quaternized to form

$R_3$ is $C_{1-4}$ alkyl, $CH_2C(O)NH_2$, or $CH_2C(O)NMe_2$; linker $L_2$ is a 1 to 12 unit chain optionally containing units selected from the group consisting of $CH_2$, $C(CH_3)_2$, O, C(O), S, S(O), $S(O)_2$, NH, $NR_4$, phenyl, monocyclic 5-membered heteroaryl, monocyclic 6-membered heteroaryl, —CH═CH— cis, —CH═CH— trans, NHC(O)NH, $NR_4$C(O)NH, NHC(O)$NR_4$, $NR_4$C(O)$NR_4$, OC(O)NH, $NR_4$C(O)O, OC(O)$NR_4$, and NHC(O)O with the proviso that $L_2$ does not contain a C(O)NH, C(O)$NR_4$, C(O)O, or C(O)S unit; the 5-membered heteroaryls are selected from the group consisting of imidazole, furane, thiophene, thiazole, isothiazole, oxazole, isoxazole, 1,2,3-oxadiazole, 1,3,4-oxadiazole, 1,2,4-oxadiazole, 1,2,3-triazole, 1,3,4-triazole, 1,2,3-thiazole, 1,3,4-thiazole, and 1,2,4-thiazole; the 6-membered heteroaryls are selected from the group consisting of pirydine, pirymidyne, pirydazine, 1,2,4-triazine, and 1,3,5-triazine; and $R_4$ is selected from the group consisting of H and $C_{1-4}$ alkyl.

In some embodiments, the compounds of formula (I) are used in various salt forms, including but not limited to the hydrochloride, hydrobromide, methanosulfonate, isethionate, tosylate, benzenesulfonate, lactate, citrate, formate, and acetate salts.

In various embodiments, the compounds of formula (I) have the following structures:

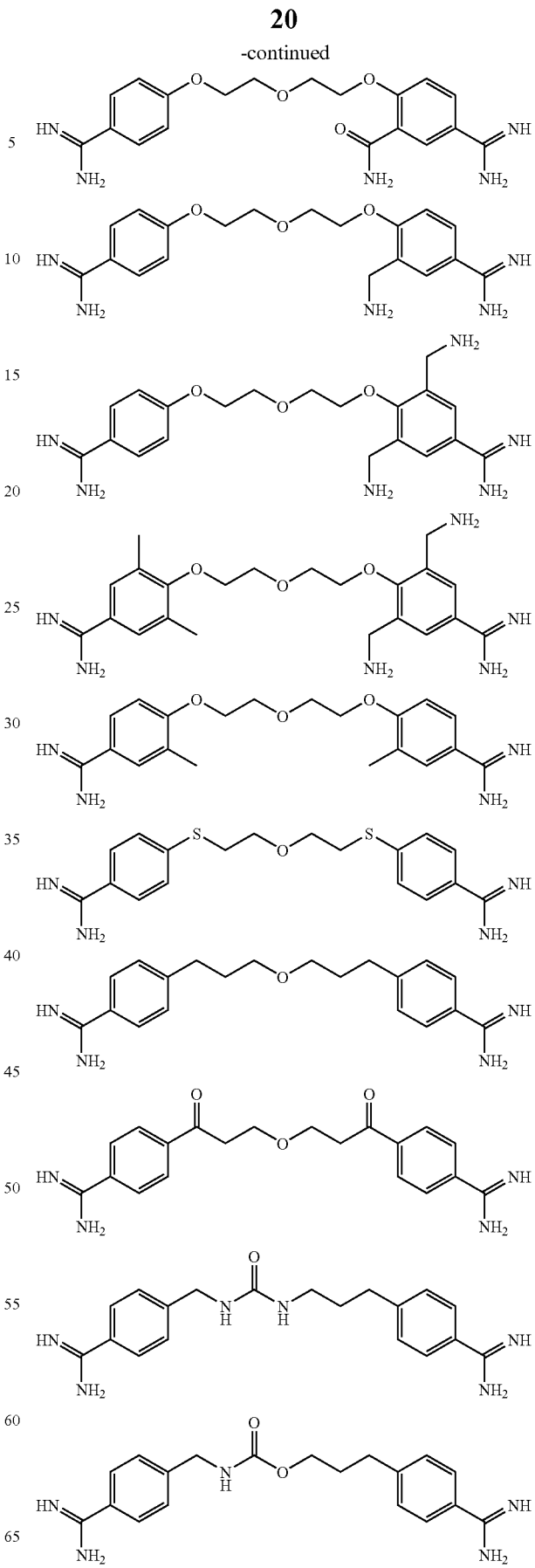

-continued
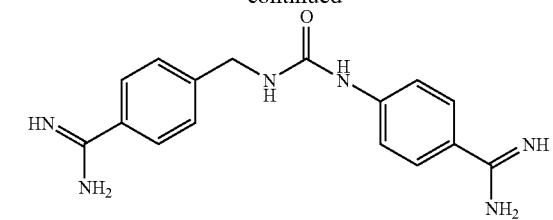
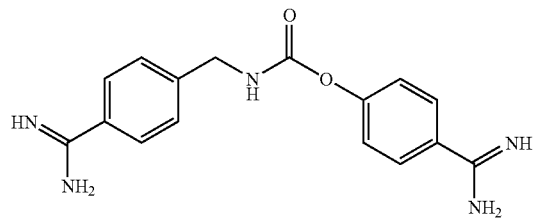
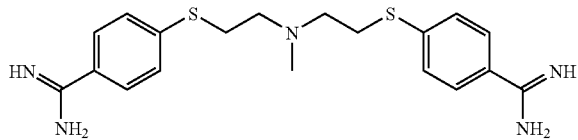
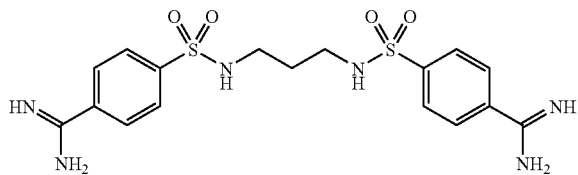
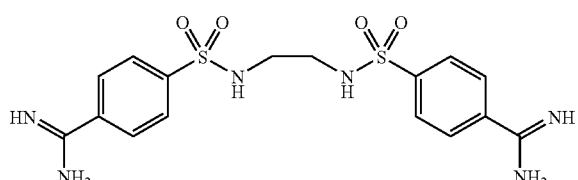
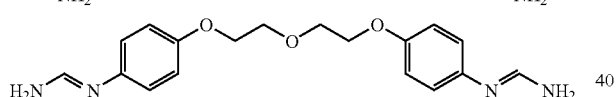
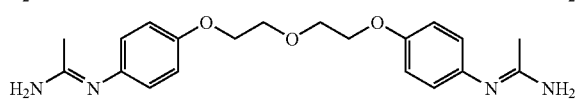
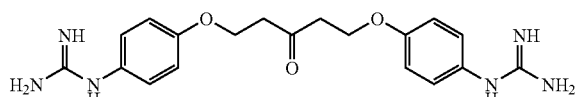
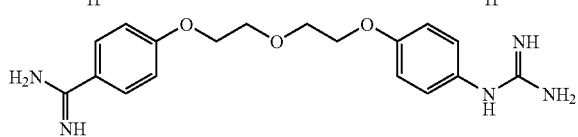
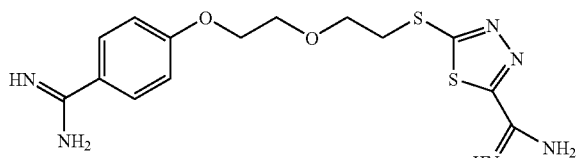
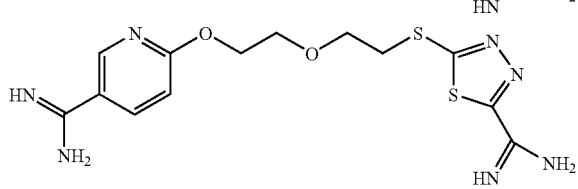
-continued
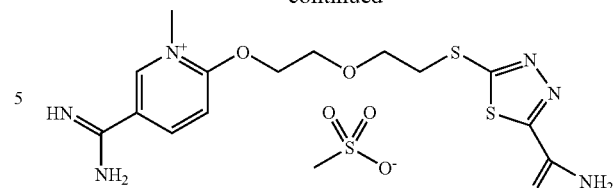
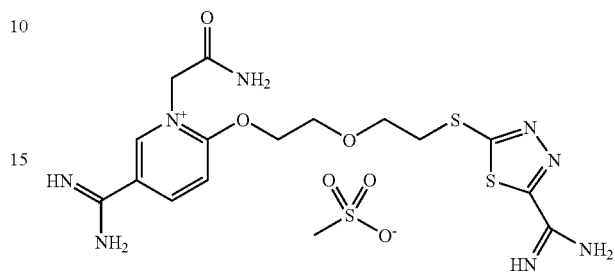
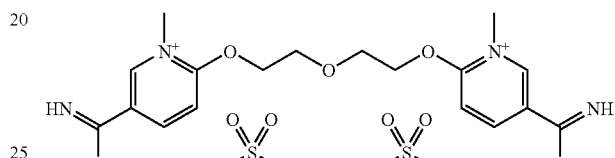
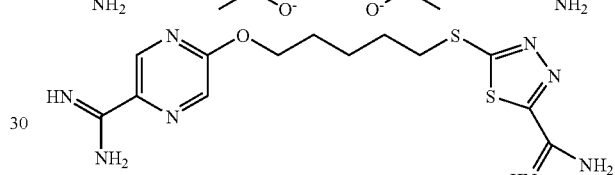
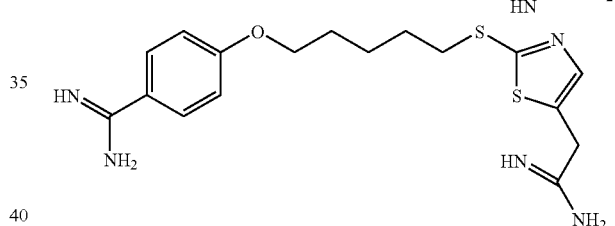
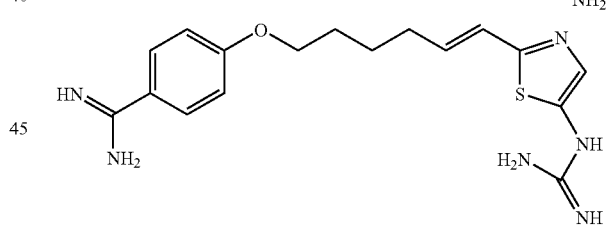
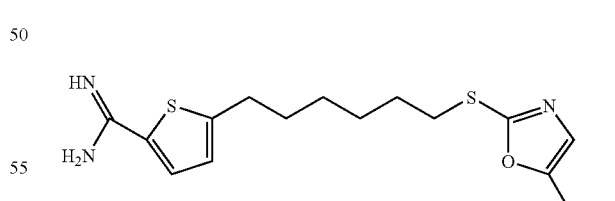
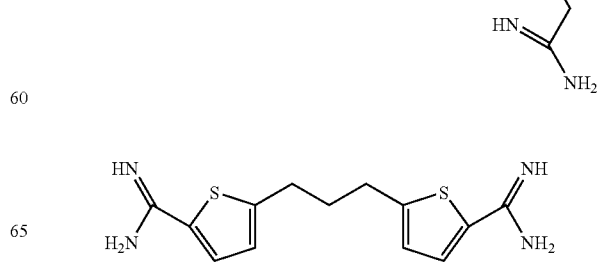

-continued

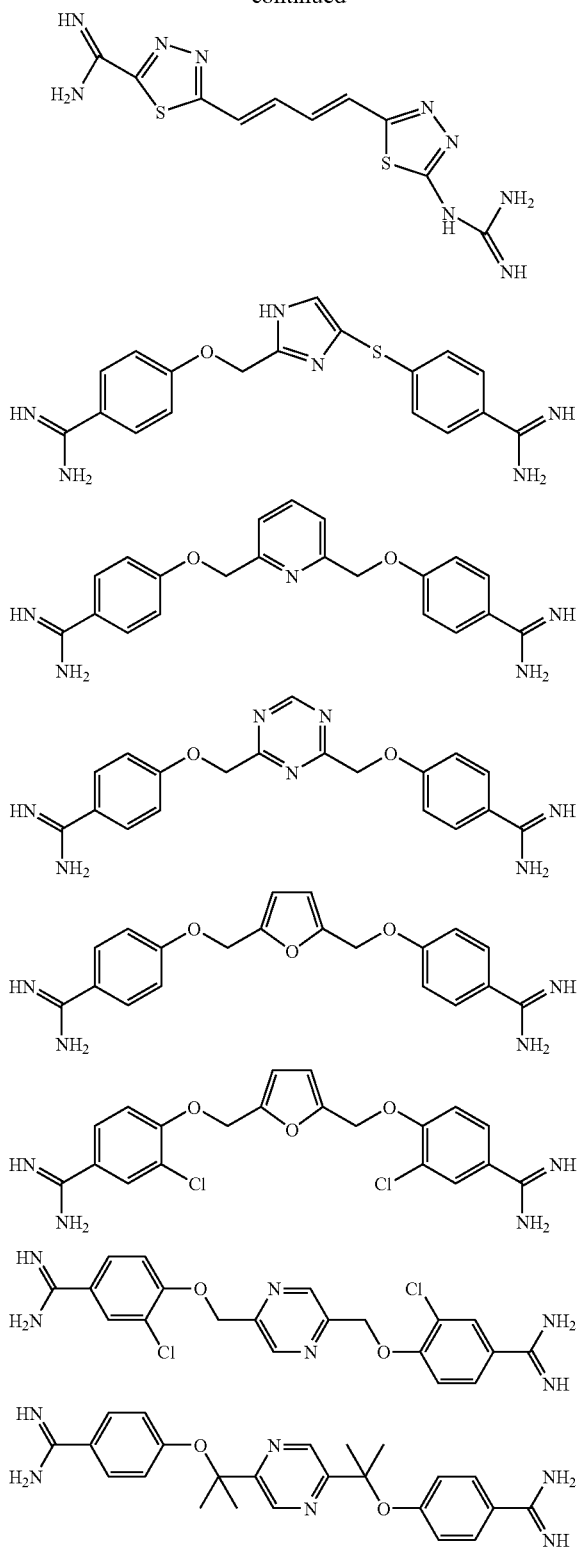

In other embodiments, compounds for use as described herein include compounds having the following structures:

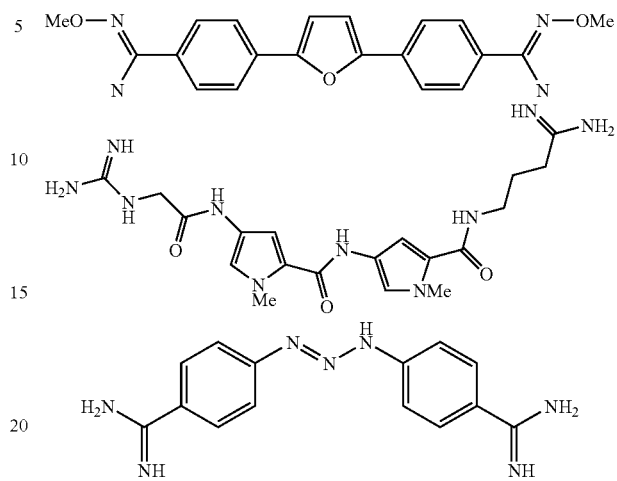

In one embodiment, compounds for use as described herein include the compounds having the formula:

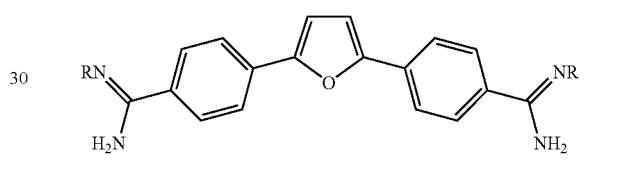

wherein R is selected from the group consisting of H, OH, OMe, and

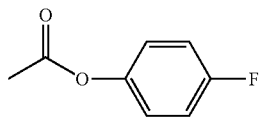

In another embodiment, compounds for use as described herein include the compounds having the formula:

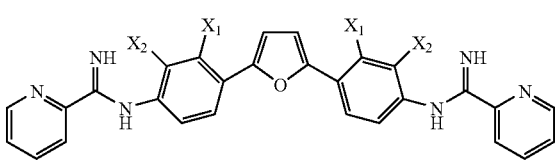

wherein $X_1$ is selected from the group consisting of H, Me, OMe, and Cl; and $X_2$ is selected from the group consisting of H, Me, and OMe.

In another embodiment, compounds for use as described herein include the compounds having the formula:

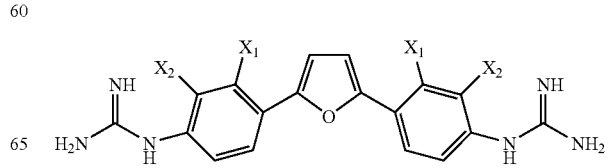

wherein $X_1$ is selected from the group consisting of H, Me, OMe, Cl, and $CF_3$; and $X_2$ is selected from the group consisting of H and Me.

In other embodiments, compounds for use as described herein include the compounds set forth below as described in the following U.S. patents:

U.S. Pat. No. 4,933,347

The above-named patent describes compounds having the following formula:

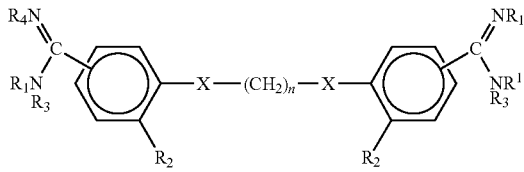

wherein each $R_1$ is H or two $R_1$ groups on the same amidine group together represent —$(CH_2)_m$—, wherein m=2, 3, or 4; $R_2$ is H, $OCH_3$, $NO_2$ or $NH_2$; $R_3$ is H, $CH_3$, or $CH_2CH_3$; n=2, 3, 4 or 5; and X is O, N or S; provided that when both $R_1$ and $R_2$ are H and X is O, then n cannot equal 5.

Particularly preferred are those compounds that have the para-amidine structure, as shown below:

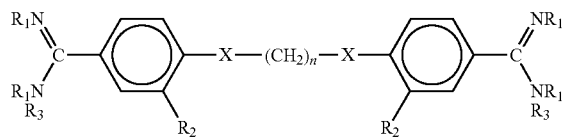

wherein $R_1$, $R_2$, $R_3$, X, m and n have the same meanings as above.

Other compounds described have the formula:

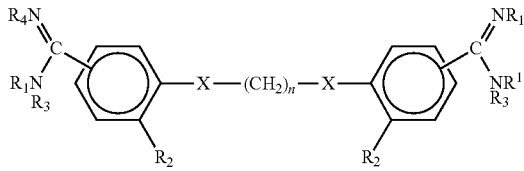

wherein each $R_1$ is H or two $R_1$ groups on the same amidine group together represent —$(CH_2)_m$—, wherein m=2, 3 or 4; $R_2$ is H $OCH_3$, $NO_2$ or $NH_2$; $R_3$ is H, $CH_3$, or $CH_2CH_3$; n=2, 3, 4 or 5; and X is O, N or S; with the provisos that when both $R_1$ and $R_2$ are H, then X is N or S, and when $R_2$ is H and X is O, then two $R_1$ groups together represent —$(CH_2)_m$—, and n=3 or 4.

Particularly preferred of these compounds are those that have the para-amidine structure, as shown below:

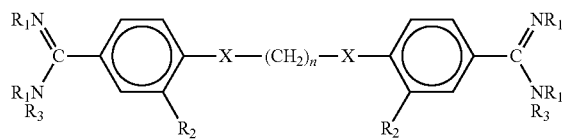

wherein $R_1$, $R_2$, $R_3$, X, m and n and have the same meanings as above. Additionally, new compounds wherein n=6 are contemplated.

Methods for synthesizing the compounds above are described in U.S. Pat. No. 4,933,347. U.S. Pat. No. 4,933,347 is hereby incorporated by reference in its entirety.

U.S. Pat. No. 5,206,236

The above-named patent describes compounds having the structure:

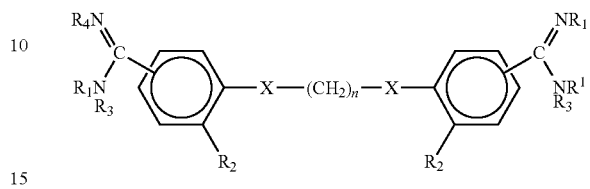

wherein X is O, N or S; $R_1$ is H or two $R_1$ groups on the same amidine group together represent —$(CH_2)_m$—, wherein m=2, 3 or 4; $R_2$ is H, $NH_2$, $OCH_3$, Cl, or $NO_2$; $R_3$ is H, $CH_3$ or $CH_2CH_3$ and n=2-6, or pharmaceutically acceptable salts thereof, or more preferably a compound of formula:

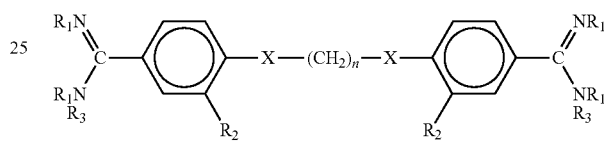

wherein X, $R_1$, $R_2$, $R_3$, m and n have the foregoing meanings, or a pharmaceutically acceptable salt thereof.

U.S. Pat. No. 5,206,236 is hereby incorporated by reference in its entirety.

U.S. Pat. No. 5,578,631

The above-named patent describes compounds having the formula:

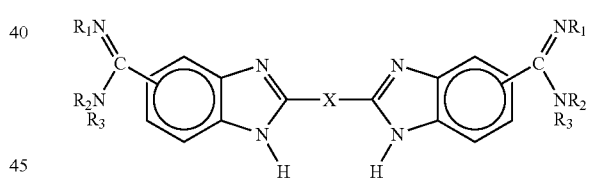

wherein $R_1$ and $R_2$ are each independently selected from the group consisting of H or lower alkyl, or $R_1$ and $R_2$ together represent —$(CH_2)_m$— wherein m is from two to four; $R_3$ is H or lower alkyl; and X is $C_{1-12}$ linear or branched, saturated or unsaturated alkyl containing up to four double bonds (e.g., —$(CH_2)_n$— wherein n is from 1-8, which is unsubstituted or substituted from 1 to 2 times with loweralkyl, and which is saturated or unsaturated and contains up to two double bonds); or a pharmaceutically acceptable salt thereof. Currently preferred are bis[5-(2-imidazolyl-2-benzimidazolyl] methane and 1,4-bis[5-(2-imidazolyl)-2-benzimidazolyl]butane, or pharmaceutically acceptable salts thereof.

Also described are compounds having the above formula wherein $R_1$ and $R_2$ together represent —$(CH_2)_m$— wherein m is from two to four; $R_3$ is H or loweralkyl; and X is selected from the group consisting of —$CH_2$—$CH_2$—$CH_2$—$CH_2$—, —CH=CH—$CH_2$—$CH_2$—, —$CH_2$—$CH_2$—CH=CH—$CH_2$—, —CH=CH—CH=CH—, and any of the foregoing substituted from 1 to 2 times with loweralkyl; and the pharmaceutically acceptable salts thereof.

U.S. Pat. No. 5,578,631 is hereby incorporated by reference in its entirety.

U.S. Pat. No. 5,602,172

The above-named patent describes compounds having the formula:

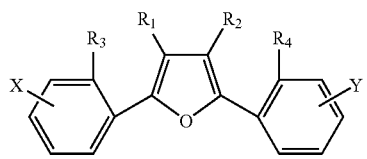

wherein $R_1$ and $R_2$ are each independently selected from the group consisting of H, loweralkyl, aryl, alkylaryl, aminoalkyl, aminoaryl, halogen, oxyalkyl, oxyaryl, or oxyarylalkyl; $R_3$ and $R_4$ are each independently selected from the group consisting of H, lower alkyl, oxyalkyl, alkylaryl, aryl, oxyaryl, aminoalkyl, aminoaryl, or halogen; and X and Y are located in the para or meta positions and are selected from the group consisting of H, loweralkyl, oxyalkyl, and

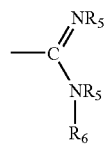

wherein each $R_5$ is independently selected from the group consisting of H, lower alkyl, alkoxyalkyl, hydroxyalkyl, aminoalkyl, alkylaminoalkyl, cycloalkyl, aryl, or alkylaryl or two $R_5$ groups together represent $C_2$-$C_{10}$ alkyl, hydroxyalkyl, or alkylene; and $R_6$ is H, hydroxy, loweralkyl, alkoxyalkyl, hydroxyalkyl, aminoalkyl, alkylamino, alkylaminoalkyl, cycloalkyl, hydroxycycloalkyl, alkoxycycloalkyl, aryl, or alkylaryl.

In some embodiments, two $R_5$ groups together represent

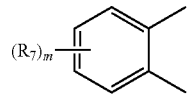

wherein m is from 1-3 and $R_7$ is H or —CONHR$_8$NR$_9$R$_{10}$, wherein $R_8$ is lower alkyl, and $R_9$ and $R_{10}$ are each independently selected from the group consisting of H and lower alkyl, although these compounds are not currently preferred.

In some embodiments, the compounds described has the structure formula above and include compounds wherein X and Y are located in the para position and are each

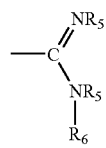

and wherein:

(a) $R_1$ is H, $R_2$ is H or loweralkyl, $R_3$ is H, $R_4$ is H, $R_5$ is H, and $R_6$ is isoalkyl, such as isopropyl, isobutyl, isopentyl, and the like;

(b) $R_1$ is H, $R_2$ is H, $R_3$ is H, $R_4$ is H, $R_5$ is H, and $R_6$ is $C_3$-$C_8$ alkoxyalkyl;

(c) $R_1$ is H, $R_2$ is H or loweralkyl, $R_3$ is H, $R_4$ is H, $R_5$ is H, and $R_6$ is alkylhydroxy, such as ethylhydroxy, propylhydroxy, butylhydroxy, pentylhydroxy, and hexylhydroxy;

(d) $R_1$ is H, $R_2$ is H or loweralkyl, $R_3$ is H, $R_4$ is H, $R_5$ is H, and $R_6$ is propoxyethyl;

(e) $R_1$ is H, $R_2$ is H or loweralkyl, $R_3$ is H, $R_4$ is H, $R_5$ is H, and $R_6$ is propoxyisopropyl;

(f) $R_1$ is H, $R_2$ is H or loweralkyl, $R_3$ is H, $R_4$ is H, $R_5$ is H, and $R_6$ is aryl or alkylaryl; and (g) $R_1$ is H, $R_2$ is H or loweralkyl, $R_3$ is H, $R_4$ is H, $R_5$ is H, and $R_6$ is alkylcycloalkyl; and pharmaceutically acceptable salts thereof.

Methods of synthesizing the compounds described above are disclosed in U.S. Pat. No. 5,602,172. U.S. Pat. No. 5,602,172 is hereby incorporated by reference in its entirety.

U.S. Pat. No. 5,668,167

The above-named patent describes compounds having the following formula:

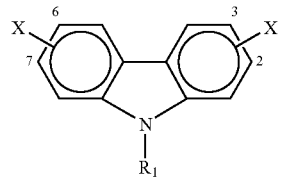

wherein X is located in the para or meta positions and is loweralkyl, loweralkoxy, alkoxyalkyl, hydroxyalkyl, aminoalkyl, alkylaminoalkyl, cycloalkyl, aryl, alkylaryl, halogen, or

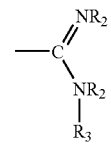

wherein each $R_2$ is independently selected from the group consisting of H, loweralkyl, alkoxyalkyl, hydroxyalkyl, aminoalkyl, alkylaminoalkyl, cycloalkyl, aryl, or alkylaryl or two $R_2$ groups together represent $C_2$-$C_{10}$ alkylene, or two $R_2$ groups together represent

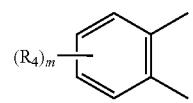

wherein m is from 1-3 and $R_4$ is H,

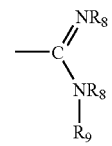

or —CONHR$_5$NR$_6$R$_7$, wherein $R_5$ is loweralkyl, $R_6$ and $R_7$ are each independently selected from the group consisting of H and lower alkyl; each $R_8$ is independently selected from the group consisting of H, loweralkyl, alkoxyalkyl, hydroxyalkyl, aminoalkyl, alkylaminoalkyl, cycloalkyl, aryl, or alkylaryl, or two $R_8$ groups together represent $C_2$-$C_{10}$ alkylene; $R_9$ is H, hydroxy, loweralkyl, alkoxyalkyl, hydroxyalkyl, aminoalkyl, alkylaminoalkyl, cycloalkyl, aryl, or alkylaryl; $R_3$ is H, hydroxy, loweralkyl, alkoxyalkyl, hydroxyalkyl, aminoalkyl, alkylaminoalkyl, cycloalkyl, aryl, or alkylaryl; $R_1$ is H, loweralkyl, alkoxyalkyl, hydroxyalkyl, aminoalkyl, alkylaminoalkyl, cycloalkyl, aryl, alkylaryl, or halogen; or a pharmaceutically acceptable salt thereof.

Methods of synthesizing the compounds described above are described in U.S. Pat. No. 5,668,167, which is hereby incorporated by reference in its entirety.

U.S. Pat. No. 5,686,456

The above-named patent describes compounds have the formula:

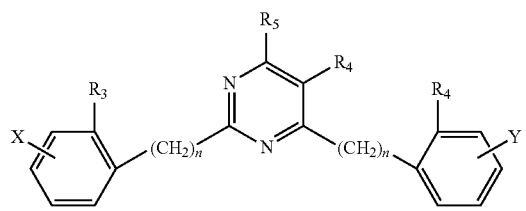

wherein X and Y are located in the para or meta positions and are selected from the group consisting of H, loweralkyl, loweralkoxy, and

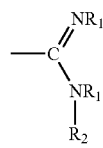

wherein each $R_1$ is independently selected from the group consisting of H, loweralkyl, alkoxyalkyl, hydroxyalkyl, aminoalkyl, alkylaminoalkyl, cycloalkyl, aryl, or alkylaryl or two $R_1$ groups together represent $C_2$-$C_{10}$ alkyl, hydroxyalkyl, or alkylene, or two $R_1$ groups together represent

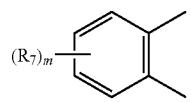

wherein m is from 1-3 and $R_7$ is H or —$CONHR_8NR_9R_{10}$, wherein $R_8$ is loweralkyl, and $R_9$ and $R_{10}$ are each independently selected from the group consisting of H and lower alkyl; $R_2$ is H, hydroxy, loweralkyl, alkoxyalkyl, hydroxyalkyl, aminoalkyl, alkylaminoalkyl, cycloalkyl, aryl, or alkylaryl; n is a number from 0 to 2 (where n is 0, the bond is direct covalent linkage between the rings); $R_3$ and $R_4$ are each independently selected from the group consisting of H, loweralkyl, loweralkoxy, alkylaryl, aryl, oxyaryl, aminoalkyl, aminoaryl, or halogen; and $R_5$ and $R_6$ are each independently selected from the group consisting of H, loweralkyl, aryl, alkylaryl, aminoalkyl, aminoaryl, halogen, oxyalkyl, oxyaryl, or oxyarylalkyl; or a pharmaceutically acceptable salt thereof.

Methods of synthesizing the compounds described above are described in U.S. Pat. No. 5,686,456, which is hereby incorporated by reference in its entirety.

U.S. Pat. No. 5,723,495

The above-named patent describes patents have the formula:

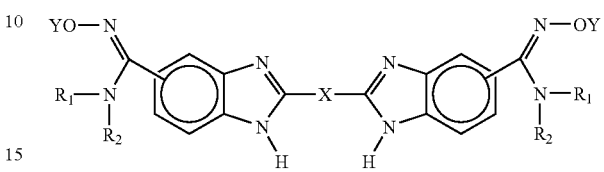

wherein $R_1$ and $R_2$ are each independently selected from the group consisting of H, loweralkyl, oxyalkyl, alkoxyalkyl, cycloalkyl, aryl, hydroxyalkyl, aminoalkyl or alkylaminoalkyl; and X is $C_{1-12}$ linear or branched, saturated or unsaturated alkyl containing up to four double bonds; and Y is H or loweralkyl; or pharmaceutically acceptable salts thereof.

In another embodiment, the above-named patent describes compounds having the formula:

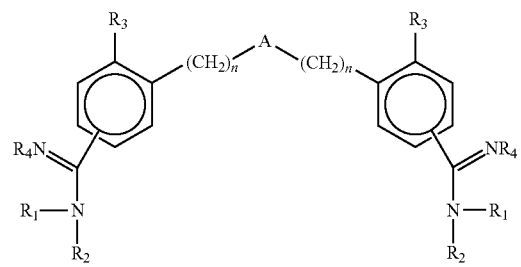

wherein $R_1$ and $R_2$ are each independently selected from the group consisting of H, loweralkyl, oxyalkyl, alkoxyalkyl, cycloalkyl, aryl, hydroxyalkyl, aminoalkyl or alkylaminoalkyl; $R_3$ is H, loweralkyl, oxyalkyl, alkoxyalkyl, hydroxyalkyl, cycloalkyl, aryl, aminoalkyl, alkylaminoalkyl or halogen; $R_4$ is —OH, or $R_1$ and $R_4$ together represent

wherein $R_5$ is

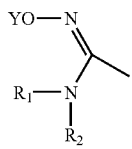

Y is H or loweralkyl; n is an integer from 0 to 2; and A is a heterocyclic aromatic group selected from the group consisting of:

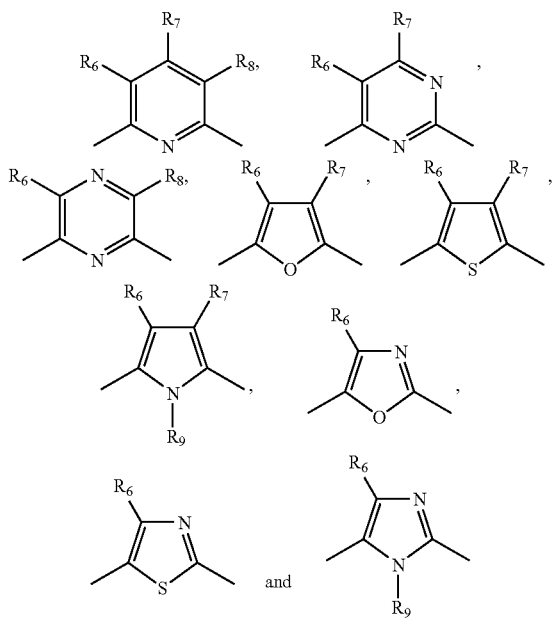

wherein $R_6$, $R_7$ and $R_8$ are each independently selected from the group consisting of H, loweralkyl, halogen, oxyalkyl, oxyaryl, or oxyarylalkyl; $R_9$ is hydrogen, loweralkyl, hydroxy, aminoalkyl or alkylaminoalkyl; or pharmaceutically acceptable salts thereof.

In another embodiment, the above-named patent describes compounds having the formula:

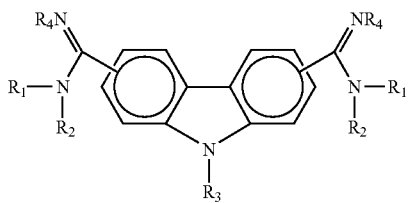

wherein $R_1$ and $R_2$ are each independently selected from the group consisting of H, loweralkyl, oxyalkyl, alkoxyalkyl, cycloalkyl, aryl, hydroxyalkyl, aminoalkyl or alkylaminoalkyl; $R_3$ is H, loweralkyl, oxyalkyl, alkoxyalkyl, hydroxyalkyl, cycloalkyl, aryl, aminoalkyl, alkylaminoalkyl or halogen; $R_4$ is —OH, or $R_1$ and $R_4$ together represent

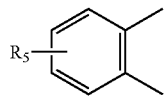

wherein $R_5$ is

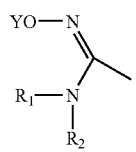

Y is H or loweralkyl; n is an integer from 0 to 2; or pharmaceutically acceptable salts thereof.

Methods of synthesizing the compounds described above are described in U.S. Pat. No. 5,723,495, which is hereby incorporated by reference in its entirety.

U.S. Pat. No. 6,127,554

The above-named patent describes compounds having the formula:

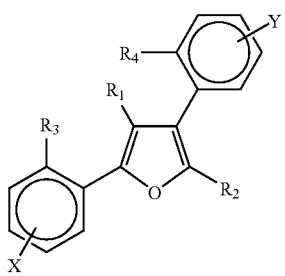

wherein $R_1$ and $R_2$ are each independently selected from the group consisting of H, loweralkyl, aryl, alkylaryl, aminoalkyl, aminoaryl, halogen, oxyalkyl, oxyaryl, or oxyarylalkyl; $R_3$ and $R_4$ are each independently selected from the group consisting of H, loweralkyl, oxyalkyl, alkylaryl, aryl, oxyaryl, aminoalkyl, aminoaryl, or halogen; and X and Y are located in the para or meta positions and are each selected from the group consisting of H, loweralkyl, oxyalkyl, and

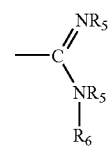

wherein each $R_5$ is independently selected from the group consisting of H, loweralkyl, alkoxyalkyl, hydroxyalkyl, aminoalkyl, alkylaminoalkyl, cycloalkyl, aryl, or alkylaryl or two $R_5$ groups together represent $C_2$ to $C_{10}$ alkyl, hydroxyalkyl, or alkylene; and $R_6$ is H, hydroxy, loweralkyl, alkoxyalkyl, hydroxyalkyl, aminoalkyl, alkylamino, alkylaminoalkyl, cycloalkyl, hydroxycycloalkyl, alkoxycycloalkyl, aryl, or alkylaryl; or a pharmaceutically acceptable salt thereof.

Methods of synthesizing the compounds described above are described in U.S. Pat. No. 6,127,554, which is hereby incorporated by reference in its entirety.

U.S. Pat. No. 6,172,104

The above-named patent describes compounds having the formula:

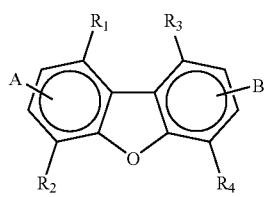

wherein $R_1$, $R_2$, $R_3$, and $R_4$ are each independently selected from the group consisting of H, loweralkyl, oxyalkyl, aryl, alkylaryl, aminoalkyl, aminoaryl, oxyaryl, oxyarylalkyl, or halogen; A and B are each selected from the group consisting of H, loweralkyl, oxyalkyl, and

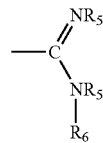

wherein each $R_5$ is independently selected from the group consisting of H, loweralkyl, alkoxyalkyl, hydroxyalkyl, aminoalkyl, alkylaminoalkyl, cycloalkyl, aryl, or alkylaryl or two $R_5$ groups together represent $C_2$ to $C_{10}$ alkyl, hydroxyalkyl, or alkylene; and $R_6$ is H, hydroxy, loweralkyl, alkoxyalkyl, hydroxyalkyl, aminoalkyl, alkylamino, alkylaminoalkyl, cycloalkyl, hydroxycycloalkyl, alkoxycycloalkyl, aryl, or alkylaryl; or a pharmaceutically acceptable salt thereof.

In another embodiment, this patent describes compounds having the formula:

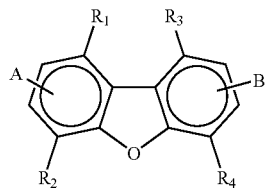

wherein $R_1$, $R_2$, $R_3$, and $R_4$ are each independently selected from the group consisting of H, loweralkyl, oxyalkyl, aryl, alkylaryl, aminoalkyl, aminoaryl, oxyaryl, oxyarylalkyl, or halogen; A and B are each selected from the group consisting of H, loweralkyl, oxyalkyl, and

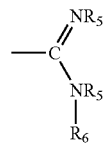

wherein each $R_5$ is independently selected from the group consisting of H, loweralkyl, alkoxyalkyl, hydroxyalkyl, aminoalkyl, alkylaminoalkyl, cycloalkyl, aryl, or alkylaryl or two $R_5$ groups together represent $C_2$ to $C_{10}$ alkyl, hydroxyalkyl, or alkylene; and $R_6$ is H, hydroxy, loweralkyl, alkoxyalkyl, hydroxyalkyl, aminoalkyl, alkylamino, alkylaminoalkyl, cycloalkyl, hydroxycycloalkyl, alkoxycycloalkyl, aryl, or alkylaryl; or a pharmaceutically acceptable salt thereof.

In another embodiment, this patent describes compounds having the formula:

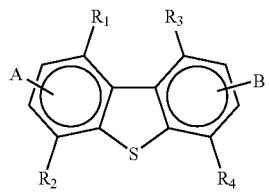

wherein $R_1$, $R_2$, $R_3$, and $R_4$ are each independently selected from the group consisting of H, loweralkyl, oxyalkyl, aryl, alkylaryl, aminoalkyl, aminoaryl, oxyaryl, oxyarylalkyl, or halogen; A and B are each selected from the group consisting of H, loweralkyl, oxyalkyl, and

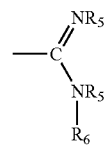

wherein: each $R_5$ is independently selected from the group consisting of H, loweralkyl, alkoxyalkyl, hydroxyalkyl, aminoalkyl, alkylaminoalkyl, cycloalkyl, aryl, or alkylaryl or two $R_5$ groups together represent $C_2$ to $C_{10}$ alkyl, hydroxyalkyl, or alkylene; and $R_6$ is H, hydroxy, loweralkyl, alkoxyalkyl, hydroxyalkyl, aminoalkyl, alkylamino, alkylaminoalkyl, cycloalkyl, hydroxycycloalkyl, alkoxycycloalkyl, aryl, or alkylaryl; or a pharmaceutically acceptable salt thereof.

In another embodiment, the above-named patent describes a compound having the formula:

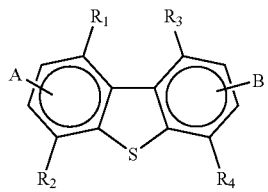

wherein $R_1$, $R_2$, $R_3$, and $R_4$ are each independently selected from the group consisting of H, loweralkyl, oxyalkyl, aryl, alkylaryl, aminoalkyl, aminoaryl, oxyaryl, oxyarylalkyl, or halogen; A and B are each selected from the group consisting of H, loweralkyl, oxyalkyl, and

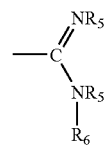

wherein: each $R_5$ is independently selected from the group consisting of H, loweralkyl, alkoxyalkyl, hydroxyalkyl, aminoalkyl, alkylaminoalkyl, cycloalkyl, aryl, or alkylaryl or two $R_5$ groups together represent $C_2$ to $C_{10}$ alkyl, hydroxyalkyl, or alkylene; and $R_6$ is H, hydroxy, loweralkyl, alkoxyalkyl, hydroxyalkyl, aminoalkyl, alkylamino, alkylaminoalkyl, cycloalkyl, hydroxycycloalkyl, alkoxycycloalkyl, aryl, or alkylaryl; or a pharmaceutically acceptable salt thereof.

Methods of synthesizing the compounds described above are described in U.S. Pat. No. 6,172,104, which is hereby incorporated by reference in its entirety.

U.S. Pat. No. 6,326,395

The above-entitled patent describes compounds having the formula:

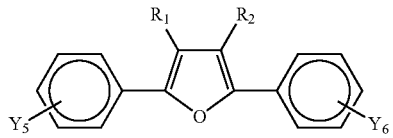

wherein $R_1$ and $R_2$ may be the same or different and selected from the group consisting of H, loweralkyl, aryl, alkylaryl, aminoalkyl, aminoaryl, halogen, oxyalkyl, oxyaryl, and oxyarylalkyl; and wherein $Y_5$ and $Y_6$ are present in the meta or para positions and may the same or different and are represented by the formula (a) or (b) selected from the group consisting of:

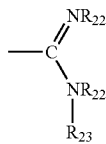

wherein each $R_{22}$ is independently selected from the group consisting of H, loweralkyl, alkoxyalkyl, hydroxyalkyl, aminoalkyl, alkylaminoalkyl, cycloalkyl, aryl, or alkylaryl or two $R_{22}$ groups together represent $C_2$-$C_{10}$ alkyl, hydroxyalkyl, or alkylene; and $R_{23}$ is H, hydroxy, loweralkyl, alkoxyalkyl, aminoalkyl, alkylamino, alkylaminoalkyl, cycloalkyl, hydroxycycloalkyl, alkoxycycloalkyl, aryl, or alkylaryl; and

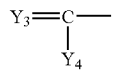

wherein $Y_3$ is selected from the group consisting of NR''' and O; wherein R''' is selected from the group consisting of H and loweralkyl; and wherein $Y_4$ is represented by the formula:

wherein $R_{20}$ is selected from the group consisting of H, loweralkyl, alkoxyalkyl, hydroxyalkyl, aminoalkyl, alkylaminoalkyl, cycloalkyl, aryl, or alkylaryl; wherein $R_{21}$ is selected from the group consisting of hydroxy, loweralkyl, alkoxyalkyl, hydroxyalkyl, aminoalkyl, alkylamino, alkylaminoalkyl, cycloalkyl, hydroxycycloalkyl, alkoxycycloalkyl, aryl, and alkylaryl.

In another embodiment, the above-named patent discloses compounds having the formula:

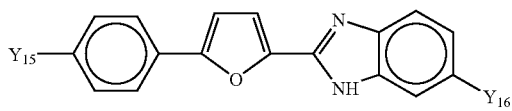

wherein $Y_{15}$ and $Y_{16}$ may be the same or different and represented by the formula:

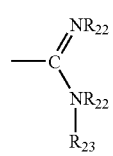

wherein: each $R_{22}$ is independently selected from the group consisting of H, loweralkyl, alkoxyalkyl, hydroxyalkyl, aminoalkyl, alkylaminoalkyl, alkylamino, cycloalkyl, aryl, or alkylaryl or two $R_{22}$ groups together represent $C_2$-$C_{10}$ alkyl, hydroxyalkyl, or alkylene; and $R_{23}$ is H, hydroxy, loweralkyl, alkoxyalkyl, aminoalkyl, alkylamino, alkylaminoalkyl, cycloalkyl, hydroxycycloalkyl, alkoxycycloalkyl, aryl, or alkylaryl.

In another embodiment, the above-named patent describes compounds having the formula:

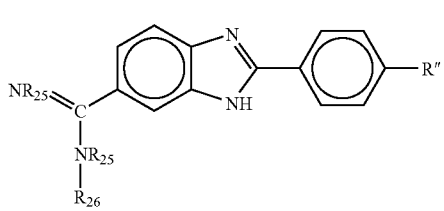

wherein each $R_{25}$ is independently selected from the group consisting of H, loweralkyl, alkoxyalkyl, hydroxyalkyl, aminoalkyl, alkylaminoalkyl, cycloalkyl, aryl, or alkylaryl or two $R_{25}$ groups together represent substituted or unsubstituted $C_2$-$C_{10}$ alkyl, hydroxyalkyl, or alkylene; and $R_{26}$ is H, hydroxy, loweralkyl, alkoxyalkyl, aminoalkyl, alkylamino, alkylaminoalkyl, cycloalkyl, hydroxycycloalkyl, alkoxycycloalkyl, aryl, or alkylaryl; R'' is hydroxy, alkoxyalkyl, hydroxyalkyl, alkoxyaryl, aryl, or the substituent selected from the formula (I) and (ii) consisting of:

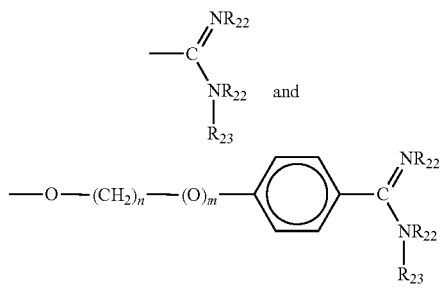

wherein n and m may be independently selected and each range from 0 to 6; each $R_{22}$ is independently selected from the group consisting of H, loweralkyl, alkoxyalkyl, hydroxyalkyl, aminoalkyl, alkylaminoalkyl, cycloalkyl, aryl, or alkylaryl or two $R_{22}$ groups together represent $C_2$-$C_{10}$ alkyl, hydroxyalkyl, or alkylene; and $R_{23}$ is H, hydroxy, loweralkyl, alkoxyalkyl, aminoalkyl, alkylamino, alkylaminoalkyl, cycloalkyl, hydroxycycloalkyl, alkoxycycloalkyl, aryl, or alkylaryl.

In another embodiment, the above-named patent describes compounds having the formula:

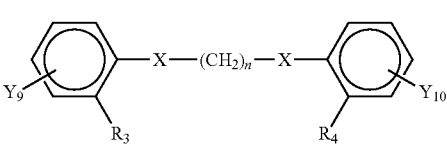

wherein n is from 2 to 6; X is selected from the group consisting of O, NH, and S; $Y_9$ and $Y_{10}$ may be in the meta or para position, are independently selected and are each represented by the formula:

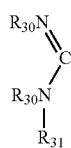

wherein each $R_{30}$ is selected from the group consisting of H, hydroxy, loweralkyl, oxyalkyl, alkoxyalkyl, cycloalkyl, aryl, hydroxyalkyl, aminoalkyl, and alkylaminoalkyl; and wherein each of the two $R_{30}$ groups together may represent $C_2$-$C_{10}$ alkyl, hydroxyalkyl, or alkylene; wherein $R_{31}$ is selected from the group consisting of H, hydroxy, loweralkyl, alkoxyalkyl, aminoalkyl, alkylamino, alkylaminoalkyl, cycloalkyl, hydroxycycloalkyl, alkoxycycloalkyl, aryl, or alkylaryl; wherein $R_3$ and $R_4$ may be the same or different and are selected from the group consisting of H, amino nitro, loweralkyl, alkoxyalkyl, hydroxyalkyl, aminoalkyl, alkylaminoalkyl, cycloalkyl, aryl, or alkylaryl.

In another embodiment, the above-named patent describes compounds having the formula:

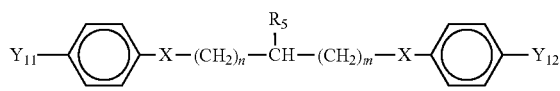

wherein X may be O, NH, or S; n and m may be the same or different and range from 2 to 6; wherein $Y_{11}$ and $Y_{12}$ may be the same or different and represented by the formula:

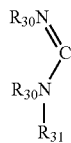

wherein each $R_{30}$ is selected from the group consisting of H, loweralkyl, oxyalkyl, alkoxyalkyl, cycloalkyl, aryl, hydroxyalkyl, aminoalkyl, and alkylaminoalkyl; and wherein each of the two $R_{30}$ groups together may represent $C_2$-$C_{10}$ alkyl, hydroxyalkyl, or alkylene; wherein $R_{31}$ is selected from the group consisting of H, hydroxy, loweralkyl, alkoxyalkyl, aminoalkyl, alkylamino, alkylaminoalkyl, cycloalkyl, hydroxycycloalkyl, alkoxycycloalkyl, aryl, or alkylaryl; wherein $R_5$ is selected from the group consisting of H, hydroxy, and

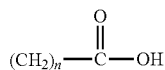

wherein n ranges from 0 to 3.

In another embodiment, the above-named patent describes compounds having the formula:

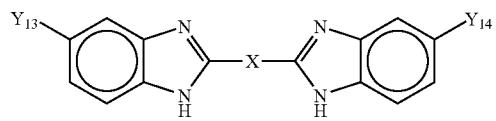

wherein X is $C_1$ to $C_{12}$ linear or branched, saturated or unsaturated alkyl containing up to four double bonds, or is substituted or unsubstituted aryl; wherein $Y_{13}$ and $Y_{14}$ may be the same or different and are represented by the formula:

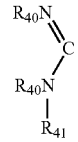

wherein $R_{40}$ and $R_{42}$ are each independently selected from the group consisting of H, loweralkyl, cycloalkyl, substituted aryl, and unsubstituted aryl, or wherein $R_{40}$ and $R_{42}$ together may represent $C_2$-$C_{10}$ alkyl, hydroxyalkyl, alkylene, substituted aryl, or unsubstituted aryl; and wherein $R_{41}$ may be H, hydroxy, loweralkyl, alkoxyalkyl, aminoalkyl, alkylamino, alkylaminoalkyl, cycloalkyl, hydroxycycloalkyl, alkoxycycloalkyl, aryl, or alkylaryl.

Methods of synthesizing the compounds described above are described in U.S. Pat. No. 6,326,395, which is hereby incorporated by reference in its entirety.

U.S. Pat. No. 6,423,737 B2

The above-named patent describes compounds having the formula:

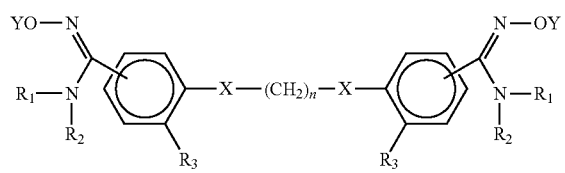

wherein $R_2$ and $R_2$ are each independently selected from the group consisting of H, loweralkyl, oxyalkyl, alkoxyalkyl, cycloalkyl, aryl, hydroxyalkyl, aminoalkyl or alkylaminoalkyl; $R_3$ is H, loweralkyl, oxyalkyl, alkoxyalkyl, hydroxyalkyl, cycloalkyl, aryl, aminoalkyl, alkylaminoalkyl or halogen; n is from 2 to 6; X is O or S; and Y is H or loweralkyl; or pharmaceutically acceptable salts thereof.

In another embodiment the above-named patent describes compounds having the formula:

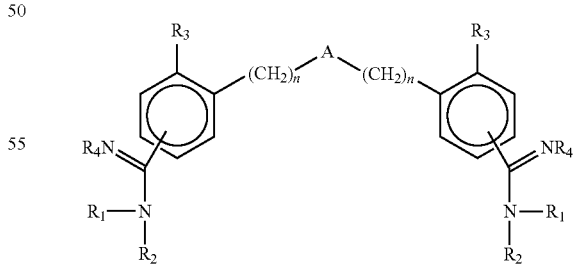

wherein $R_1$ and $R_2$ are each independently selected from the group consisting of H, loweralkyl, oxyalkyl, alkoxyalkyl, cycloalkyl, aryl, hydroxyalkyl, aminoalkyl or alkylaminoalkyl; $R_3$ is H, loweralkyl, oxyalkyl, alkoxyalkyl, hydroxyalkyl, cycloalkyl, aryl, aminoalkyl, alkylaminoalkyl or halogen; $R_4$ is —OY, or $R_1$ and $R_4$ together represent

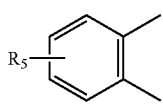

wherein $R_5$ is

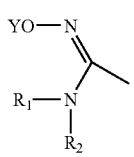

Y is H or loweralkyl; n is an integer from 0 to 2; and A is a heterocyclic aromatic group selected from the group consisting of:

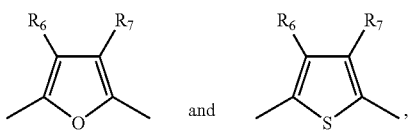

wherein $R_6$ and $R_7$ are each independently selected from the group consisting of H, loweralkyl, halogen, oxyalkyl, oxyaryl, or oxyarylalkyl; or pharmaceutically acceptable salts thereof.

Methods of synthesizing the compounds described above are described in U.S. Pat. No. 6,423,737, which is hereby incorporated by reference in its entirety.

U.S. Pat. No. 6,649,652

The above-named patent describes compounds having the formula:

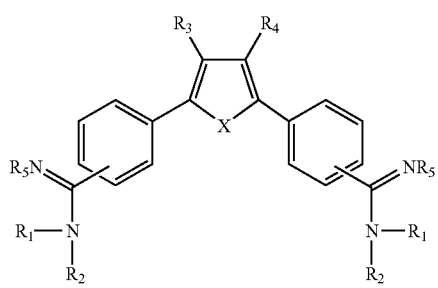

wherein X may be O, S, or NR' wherein R' is H or loweralkyl; $R_1$ and $R_2$ may be independently selected from the group consisting of H, loweralkyl, oxyalkyl, alkoxyalkyl, cycloalkyl, aryl, hydroxyalkyl, aminoalkyl, and alkylaminoalkyl; $R_3$ and $R_4$ are each independently selected from the group consisting of H, loweralkyl, halogen, oxyalkyl, oxyaryl, and oxyarylalkyl; $R_5$ is represented by a formula selected from the group consisting of:

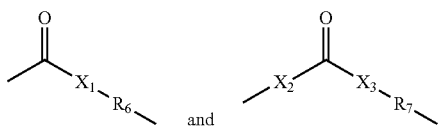

wherein: $X_1$, $X_2$, and $X_3$ are independently selected from O and S; and $R_6$ and $R_7$ are independently selected from the group consisting of loweralkyl, aryl, alkylaryl, oxyaryl, an ester-containing substituent, and oxyalkyl; or a pharmaceutically acceptable salt thereof. Preferably, $R_6$ and $R_7$ are independently selected from the group consisting of $CH_3$, $CH_2CCl_3$, $CH_2CH_3$,

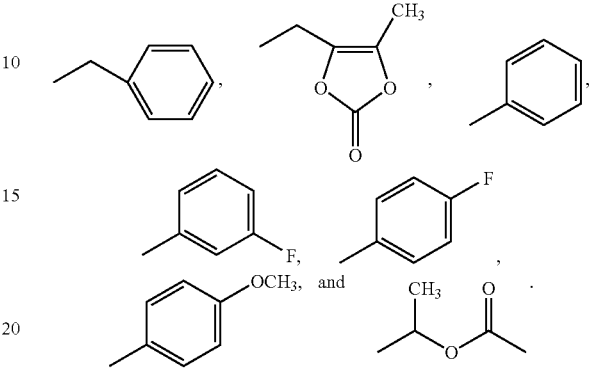

In one preferred embodiment, each of the substituents present on the compound represented by the formula:

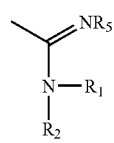

are present on the para positions of the aromatic groups, although these substituents may be present in the meta positions.

Methods of synthesizing the compounds described above are described in U.S. Pat. No. 6,649,652, which is hereby incorporated by reference in its entirety.

U.S. Pat. No. 6,635,668

The above-named patent describes compounds having the formula:

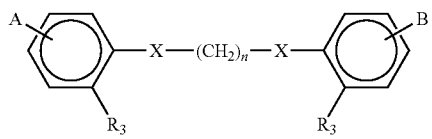

wherein A and B are each independently selected from the group consisting of H, loweralkyl, oxyalkyl, nitro, amino, aminoalkyl, halo, hydroxy, carboxy, and compounds of formula:

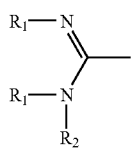

subject to the proviso that at least one of A and B is such compound; $R_1$ and $R_2$ are each independently selected from the group consisting of H, loweralkyl, oxyalkyl, alkoxyalkyl, cycloalkyl, aryl, hydroxyalkyl, aminoalkyl and alkylaminoalkyl; or two $R_1$ group on the same amidine group together represent —$(CH_2)_m$— wherein m is 2, 3, or 4; $R_3$ is H, loweralkyl, oxyalkyl, alkoxyalkyl, hydroxyalkyl, cycloalkyl, aryl, aminoalkyl, alkylaminoalkyl or halogen; n is from 2 to 6; and X is O, NH, or S; or a pharmaceutically acceptable salt thereof. In one embodiment, $R_1$, $R_2$ and $R_3$ are H; X is O; and n is 5.

In another embodiment, the above-named patent describes compounds having the formula:

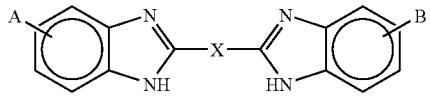

wherein: A and B are each independently selected from the group consisting of H, loweralkyl, oxyalkyl, nitro, amino, aminoalkyl, halo, hydroxy, carboxy, and compounds of formula:

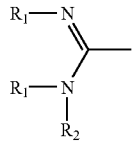

subject to the proviso that at least one of A and B is such compound; $R_1$ and $R_2$ are each independently selected from the group consisting of H, loweralkyl, oxyalkyl, alkoxyalkyl, cycloalkyl, aryl, hydroxyalkyl, aminoalkyl and alkylaminoalkyl; or two $R_1$ group on the same amidine group together represent —$(CH_2)_m$— wherein m is 2, 3, or 4; $R_3$ is H, loweralkyl, oxyalkyl, alkoxyalkyl, hydroxyalkyl, cycloalkyl, aryl, aminoalkyl, alkylaminoalkyl or halogen; X is linear or branched, saturated or unsaturated C1-C12 alkyl containing up to 4 double bonds; or X is a heterocyclic aromatic group selected from the group consisting of:

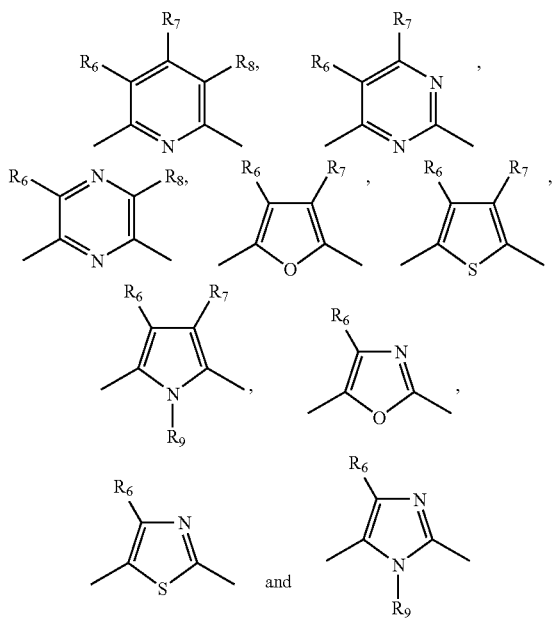

wherein $R_6$, $R_7$, and $R_8$ are each independently selected from the group consisting of H, loweralkyl, halogen, oxyalkyl, oxyaryl, or oxyarylalkyl; $R_9$ is hydrogen, loweralkyl, hydroxy, aminoalkyl or alkylaminoalkyl; or the pharmaceutically acceptable salts thereof.

In another embodiment, the above-named patent describes compounds having the formula:

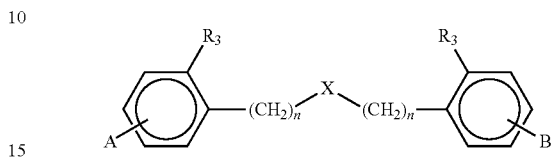

wherein: A and B are each independently selected from the group consisting of H, loweralkyl, oxyalkyl, nitro, amino, aminoalkyl, halo, hydroxy, carboxy, and substituents of formula:

subject to the proviso that at least one of A and B is such substituent; $R_1$ and $R_2$ are each independently selected from the group consisting of H, loweralkyl, oxyalkyl, alkoxyalkyl, cycloalkyl, aryl, hydroxyalkyl, aminoalkyl and alkylaminoalkyl; or two $R_1$ groups on the same amidine group together represent —$(CH_2)_m$— wherein m is 2, 3, or 4; $R_3$ is H, loweralkyl, oxyalkyl, alkoxyalkyl, hydroxyalkyl, cycloalkyl, aryl, aminoalkyl, alkylaminoalkyl or halogen; or two $R_1$ groups on the same amidine group together represent

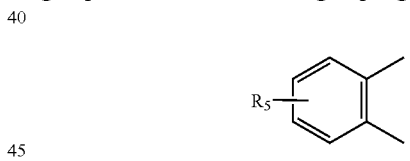

wherein $R_5$ is

n is an integer from 0 to 2; and A is a heterocyclic aromatic group selected from the group consisting of:

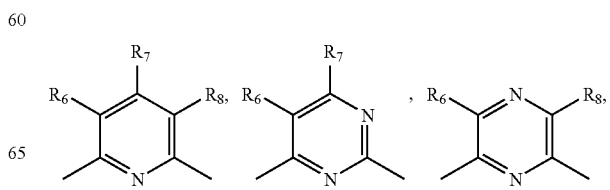

-continued

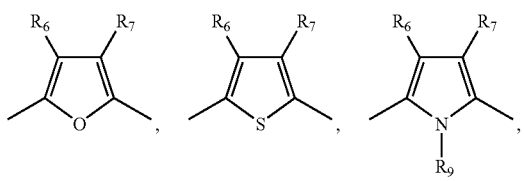

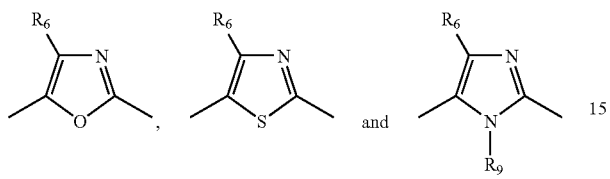

wherein $R_6$, $R_7$, and $R_8$ are each independently selected from the group consisting of H, loweralkyl, halogen, oxyalkyl, oxyaryl, or oxyarylalkyl; $R_9$ is hydrogen, loweralkyl, hydroxy, aminoalkyl or alkylaminoalkyl; and the pharmaceutically acceptable salts thereof.

In another embodiment, the above-named patent describes compounds having the formula:

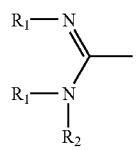

wherein A and B are each independently selected from the group consisting of H, loweralkyl, oxyalkyl, nitro, amino, aminoalkyl, halo, hydroxy, carboxy, and substituents of formula:

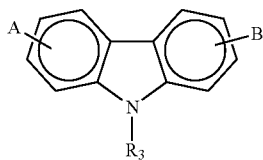

subject to the proviso that at least one of A and B is such a substituent; $R_1$ and $R_2$ are each independently selected from the group consisting of H, loweralkyl, oxyalkyl, alkoxyalkyl, cycloalkyl, aryl, hydroxyalkyl, aminoalkyl and alkylaminoalkyl; or two $R_1$ group on the same amidine group together represent —$(CH_2)_m$— wherein m is 2, 3, or 4; $R_3$ is H, loweralkyl, oxyalkyl, alkoxyalkyl, hydroxyalkyl, cycloalkyl, aryl, aminoalkyl, alkylaminoalkyl or halogen; or two $R_1$ groups on the same amidine group together represent

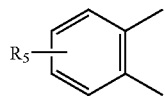

wherein $R_5$ is

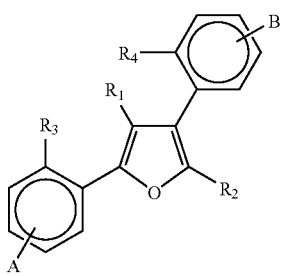

and the pharmaceutically acceptable salts thereof.

In another embodiment, the above-named patent describes compounds having the formula:

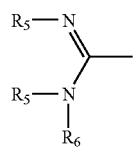

wherein A and B are each independently selected from the group consisting of H, loweralkyl, oxyalkyl, nitro, amino, aminoalkyl, halo, hydroxy, carboxy, and substituents of formula:

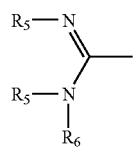

subject to the proviso that at least one of A and B is such a substituent; $R_1$ and $R_2$ are each independently selected from the group consisting of H, loweralkyl, aryl, alkylaryl, aminoalkyl, aminoaryl, halogen, oxyalkyl, oxyaryl, or oxyarylalkyl; $R_3$ and $R_4$ are each independently selected from the group consisting of H, loweralkyl, oxyalkyl, alkylaryl, aryl, oxyaryl, aminoalkyl, aminoaryl, or halogen; and each $R_5$ is independently selected from the group consisting of H, loweralkyl, alkoxyalkyl, hydroxyalkyl, aminoalkyl, alkylaminoalkyl, cycloalkyl, aryl, or alkylaryl or two $R_5$ groups together represent $C_2$ to $C_{10}$ alkyl, hydroxyalkyl, or alkylene; and $R_6$ is H, hydroxy, loweralkyl, alkoxyalkyl, hydroxyalkyl, aminoalkyl, alkylamino, alkylaminoalkyl, cycloalkyl, hydroxycycloalkyl, alkoxycycloalkyl, aryl, or alkylaryl; or a pharmaceutically acceptable salt thereof.

In another embodiment, the above-named patent describes compounds having the formula:

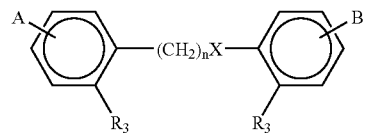

wherein A and B are each independently selected from the group consisting of H, loweralkyl, oxyalkyl, nitro, amino, aminoalkyl, halo, hydroxy, carboxy, and substituents of formula:

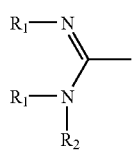

subject to the proviso that at least one of A and B is such a substituent; $R_1$ and $R_2$ are each independently selected from the group consisting of H, loweralkyl, oxyalkyl, alkoxyalkyl, cycloalkyl, aryl, hydroxyalkyl, aminoalkyl and alkylaminoalkyl; or two $R_1$ group on the same amidine group together represent —$(CH_2)_m$— wherein m is 2, 3, or 4; $R_3$ is H, loweralkyl, oxyalkyl, alkoxyalkyl, hydroxyalkyl, cycloalkyl, aryl, aminoalkyl, alkylaminoalkyl or halogen; or two $R_1$ groups on the same amidine group together represent

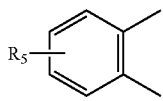

wherein $R_5$ is

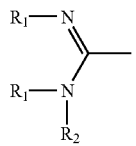

X is O, S or NH; n is an integer from 1 to 8; and the pharmaceutically acceptable salts thereof.

U.S. Pat. No. 5,668,167 is hereby incorporated by reference in its entirety.

U.S. Pat. No. 6,613,787

The above-named patent describes compounds having the formula:

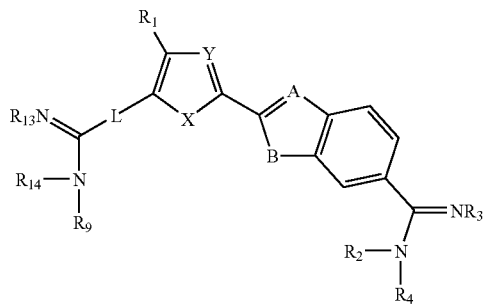

wherein X is selected from the group consisting of O, S, and NH; Y is CH or N; A is CH or N; B is selected from the group consisting of NH, O or S; $R_1$ is selected from the group consisting of H, loweralkyl, halogen, oxyalkyl, oxyaryl, and oxyarylalkyl; $R_2$ and $R_9$ are each independently selected from the group consisting of H, H2, hydroxy, lower alkyl, cycloalkyl, aryl, alkylaryl, alkoxyalkyl, hydroxycycloalkyl, alkoxycycloalkoxy, hydroxyalkyl, aminoalkyl and alkylaminoalkyl; and $R_3$, $R_4$, $R_{13}$ and $R_{14}$ are each independently selected from the group consisting of H, lower alkyl, alkoxyalkyl, cycloalkyl, aryl, alkylaryl, hydroxyalkyl, aminoalkyl, and alkylaminoalkyl, or $R_3$ and $R_4$ together or $R_{13}$ and $R_{14}$ together represent a $C_2$ to $C_{10}$ alkyl, hydroxyalkyl, or alkylene, or $R_3$ and $R_4$ together or $R_{13}$ and $R_{14}$ together are:

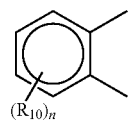

wherein n is a number from 1 to 3, and $R_{10}$ is H or —$CONHR_{11}NR_{15}R_{16}$, wherein $R_{11}$ is lower alkyl and $R_{15}$ and $R_{16}$ are each independently selected from the group consisting of H and lower alkyl; L is selected from the group consisting of:

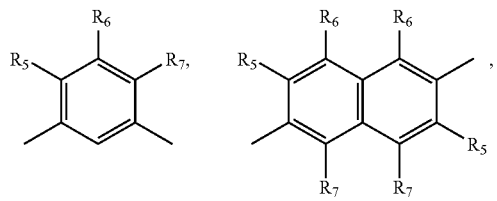

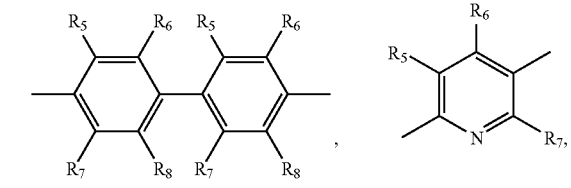

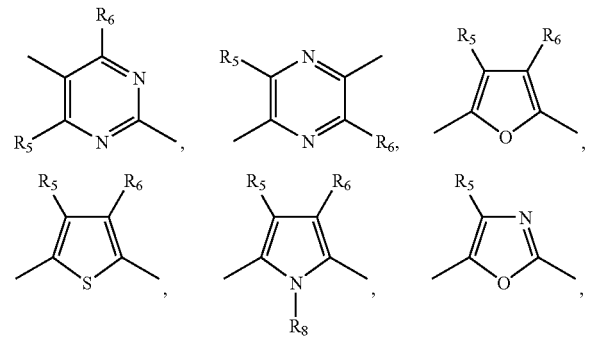

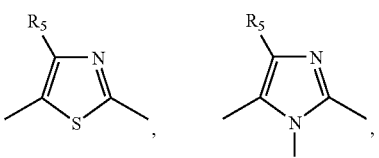

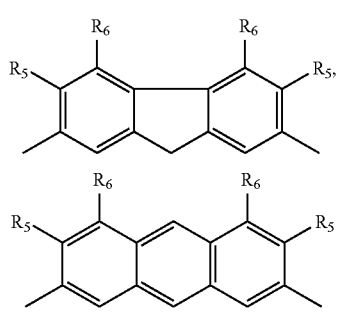

-continued

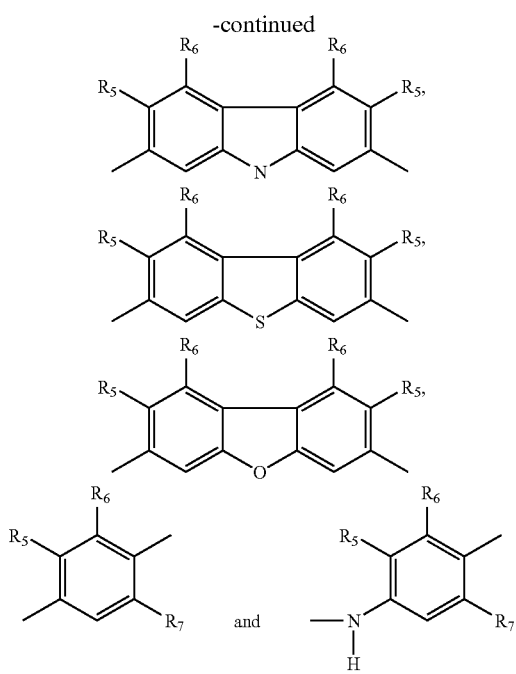

wherein $R_5$, $R_6$, $R_7$, and $R_8$ are each individually selected from the group consisting of H, alkyl, halo, aryl, arylalkyl, aminoalkyl, aminoaryl, oxoalkyl, oxoaryl, and oxoarylalkyl; and wherein the compound of Formula I binds mixed-sequence DNA in the minor groove in a dimer formation.

In a preferred embodiment the compound described above is a dication, L is:

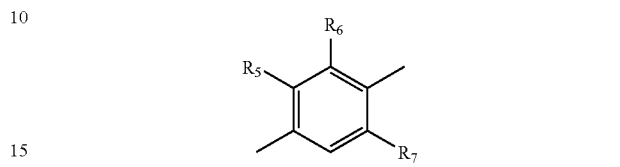

A is N; B is NH; X is O; Y is CH; $R_1$, $R_2$, $R_4$, $R_5$, $R_6$, $R_7$, $R_8$, $R_9$ and $R_{14}$ are each H; and $R_3$ and $R_{13}$ are each $H_2$.

Methods of synthesizing the compounds described above are described in U.S. Pat. No. 6,613,787, which is hereby incorporated by reference in its entirety.

U.S. Pat. No. 4,619,942

The above named patent describes the following compounds:

| | | |
|---|---|---|
| 1 | Benzamidine | 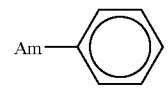 |
| 2 | Pentamidine | 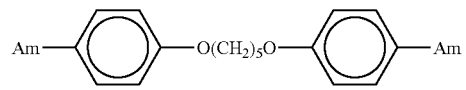 |
| 3 | 1-(4-Amidinophenoxy-6-phenoxyhexane | 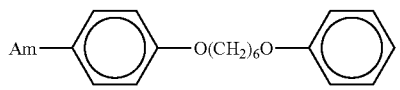 |
| 4 | 1-(4-Amidinophenoxy)-8-phenoxyoctane | 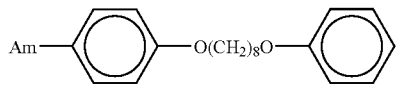 |
| 5 | 1,4-Di(4-amidinophenoxy)-2-butanol | 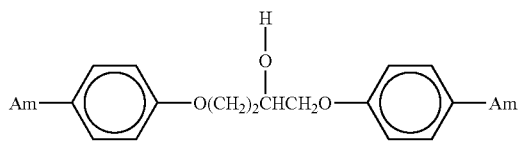 |
| 6 | α,α'-Bis(4-amidino-2-iodophenoxy)-m-xylene | 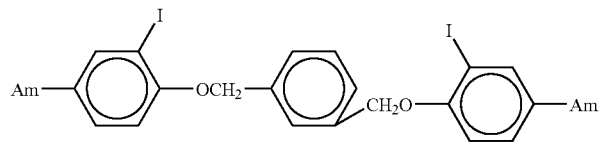 |
| 7 | Bis(5-amidino-2-benzimidazolyl)methane | 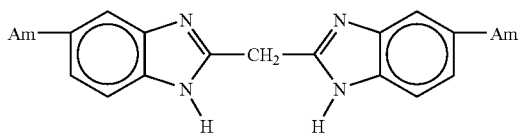 |

-continued

| 8 | 1,2-Bis(5-amidino-2-benzimidazolyl)ethane | 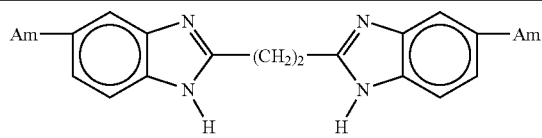 |
| 9 | 5-Amidinoindole | 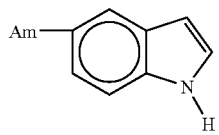 |
| 10 | 5-Amidinobenzofuran | 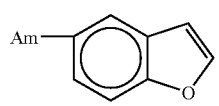 |
| 11 | 5-Amidinobenzimidazole | 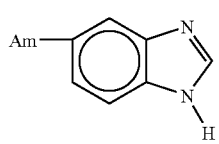 |
| 12 | 5-Amidino-1-methylindole | 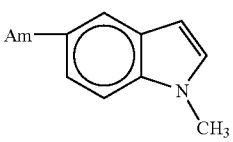 |
| 13 | 5-Amidino-1-(4-amidinobenzyl)indole | 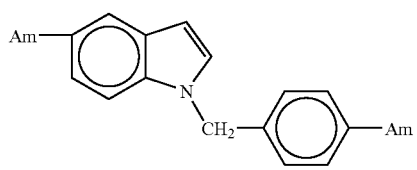 |

U.S. Pat. No. 4,619,942 is hereby incorporated by reference in its entirety.

U.S. Pat. No. 4,324,794

The above-named patent describes compounds having the formula:

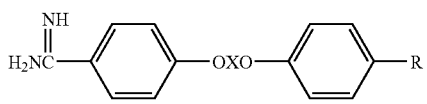

wherein R=H or C(NH)NH$_2$ and X=alkane-1, ω-diyl, or 2-hydroxybutane-1,4-diyl.

In another embodiment, the above-named patent describes compounds having the formula:

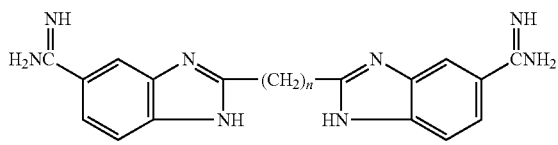

wherein n=1 or 2.

In another embodiment, the above-named patent describes compounds having the formula:

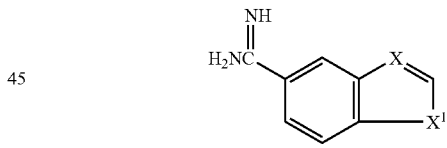

wherein X=CH or N; X$^1$=O, NH, NMe, or NCH$_2$C$_6$H$_4$C(NH)NH$_{2\text{-}4}$).

Methods for synthesizing the compounds disclosed above are described in U.S. Pat. No. 4,324,794, which is hereby incorporated by reference in its entirety.

U.S. Pat. No. 6,699,862

The above-named patent describes compounds having the formula:

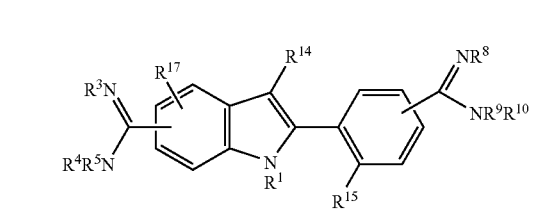

wherein $R^1$=H or alkyl; $R^3$, $R^4$, $R^5$, $R^8$, $R^9$, and $R^{10}$=H or alkyl; alternatively, $R^3R^4$ and $R^8R^9$ form an imidazolinyl group; $R^{14}$=H, $NHCO(CH_2)_mR^{20}$, $(CH_2)_mR^{20}$, $CHMeR^{20}$, $(CH_2)_m(C_6H_3)R^7$, $(CH_2)_m(C_6H_3)R^2$, $(CH_2)_m$(heterocyclyl)$R^7$, $(CH_2)_n$(heterocyclyl)$R^{20}$, $CH_2CH{:}CHR^{20}$, $(CH_2)_m$ $CONHCHR^{20}R^{21}$, $(CH_2)_m CONHCH_2 CONHCHRR^{21}$; $R^{17}$=H, halo, alkyl, $CF_3$, CN, $NO_2$, $N(R^1)_2$, OH, alkylalkoxy; $R^{20}$=$CO_2R^1$, $CH(OH)CH_2OH$, $CONH_2$, CHO; $R^{21}$=H, alkyl, $(CH_2)_nR^{22}$, $CHMeCH_2CO_2R^1$, $CH_2Ph$; $R^{22}$=H, $NH_2$, $OR^1$, $SR^1$, CN $OCH_2Ph$, $O(CH_2)_mOR^1$, $CO_2R^1$, thienyl, tetrahydropyranyl, $CH(OH)CH_2OH$, COC-Me${:}CH_2$, $NHCO_2CH_2Ph$, $SO_2R^1$; m=1-3; and n=1-5.

Methods for synthesizing the compounds disclosed above are described in U.S. Pat. No. 6,699,862, which is hereby incorporated by reference in its entirety.

U.S. Pat. No. 5,248,673

The above-named patent discloses the compound having the formula:

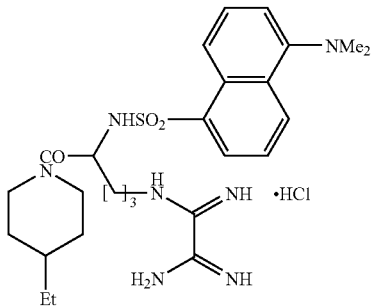

U.S. Pat. No. 5,248,673 is hereby incorporated by reference in its entirety.

U.S. Pat. No. 6,106,866

The above-named patent describes the compound of formula:

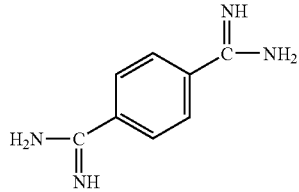

U.S. Pat. No. 6,106,866 is hereby incorporated by reference in its entirety.

U.S. Pat. No. 5,597,573

The above-named patent describes compounds having the formula:

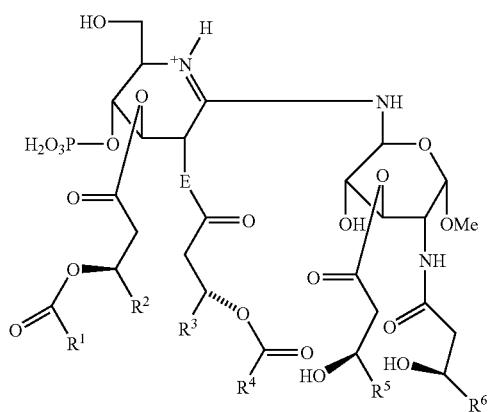

wherein $R^1$-$R^6$=(un)substituted alkyl, alkene, or alkyne and E=O or NH. U.S. Pat. No. 5,597,573 is hereby incorporated by reference in its entirety.

Other U.S. patents also disclose compounds useful in the present invention, some of which are addressed above. The patents include U.S. Pat. Nos. 6,503,940; 6,486,200; 6,025,398; 6,008,247; 5,843,980; 6,214,883; 5,668,166; 5,627,184; 5,622,955; 5,606,058; 5,521,189; 5,428,051; 5,202,320; 4,963,589; 4,397,863; 4,324,794; 6,204,279; and 6,245,746, all of which are hereby incorporated by reference in their entirety.

In other embodiments, compounds for use as described herein include the compounds set forth below as described in the following published international PCT applications, published foreign patent applications, and published articles:

PCT International Application No. WO 2004/006849 A2

The above-named PCT application describes compounds having the following formulae:

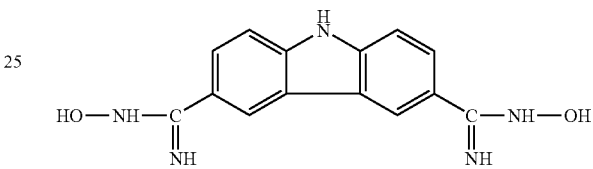

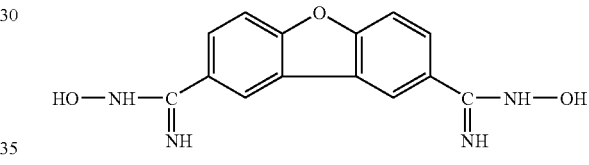

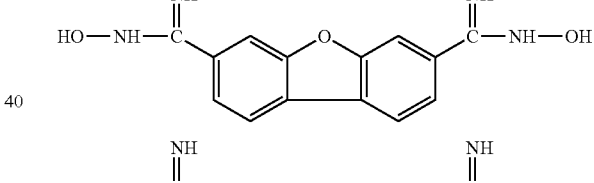

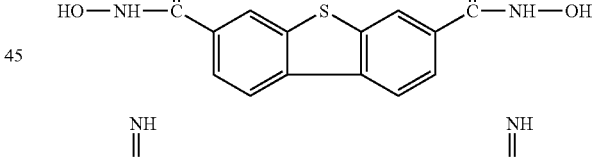

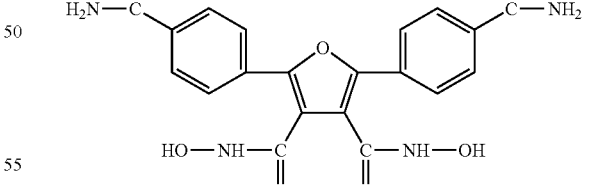

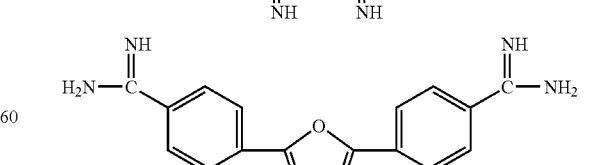

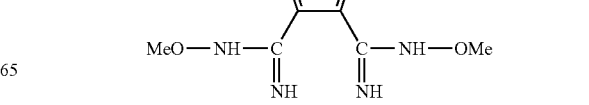

-continued

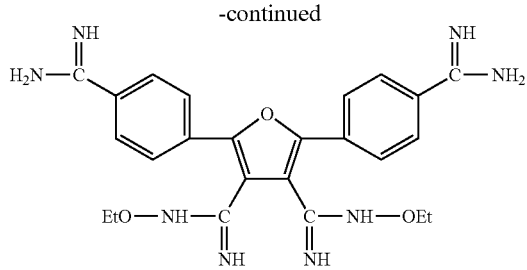

PCT Application No. WO 2004/006849 is hereby incorporated by reference in its entirety.

"Antileishmanial Activities of Several Classes of Aromatic Dications," Brendle, James J., et al., *Antimicrobial agents and Chemotherapy* (2002), 46(3), 797-807

The above-named article describes compounds having the formulae:

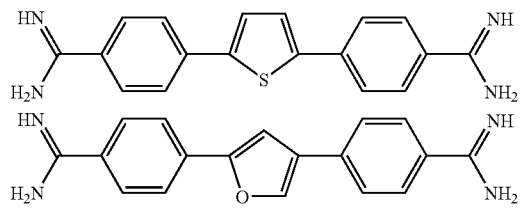

This article is hereby incorporated by reference in its entirety.
PCT International Application No. WO 2001/021585 A2
The above-named PCT application describes the compound having the formula:

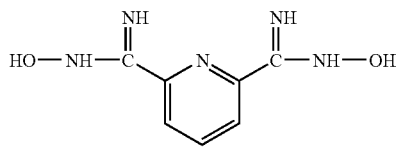

This application is hereby incorporated by reference in its entirety.
PCT International Patent Application WO 2000/010990 A2
The above-named application discloses compounds having the formula:

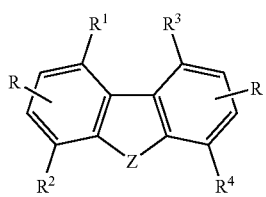

wherein each R independently is H, alkyl, oalkoxy, C(NR$^5$) NR$^5$R$^6$; R$^1$-R$^4$=H, halo, alkyl, alkoxy, etc.; R$^5$=H, alkyl, alkoxy, aryl, etc.; R$^5$=alkylene, etc.; R$^6$=H, OH, alkyl, alkoxy, etc.; and Z=O or S.

In one embodiment, the compound has the formula:

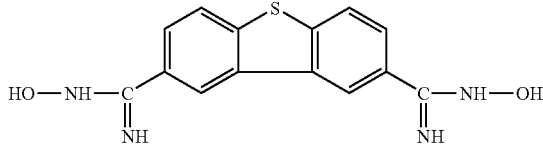

PCT Application No. WO 2000/010990 A2 is hereby incorporated by reference in its entirety.

"Reactions of 1,2,5-Thiadiazole-3,4-Dicarbonitrile," Moerkved, Eva H., et al., *Acta chemica Scandinavica* (1994), 48(4), 372-6

The above-named article discloses compounds having the formulas:

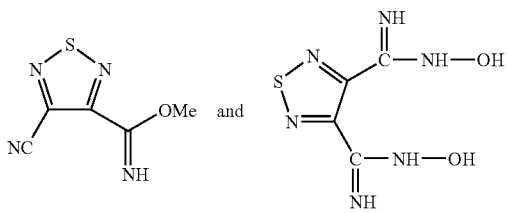

This article is hereby incorporated by reference in its entirety.

"Model Studies on the Structure of Poly(Amide Oximes) and their Cyclodehydration Reactions Leading to Poly(1,2,4-Oxadiazoles)," Jung, Jin Chul, et al., *Journal of Polymer Science, Part a: Polymer Chemistry* (1993), 31(13), 3351-9

The above-named article discloses compounds having the following structures:

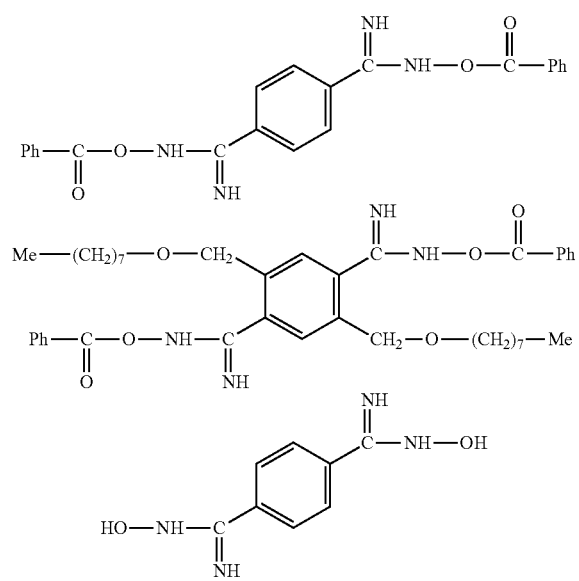

-continued

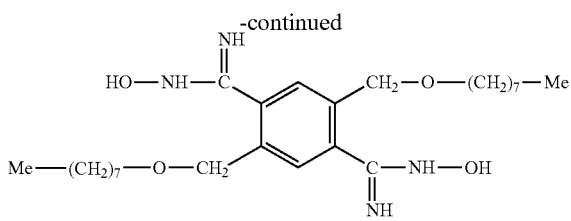

This article is hereby incorporated by reference in its entirety.

"Synthesis of Mixed 1,2,4-Oxadiazoles by Reaction of Perfluorinated Nitriles with benz- and terephthalamidoximes," kabakchi, e. v., et al., *Izvestiya Akademi Nauk, Seriya Khimicheskaya* (1992), (8), 1863-70

The above-named article discloses compounds having the following formulae:

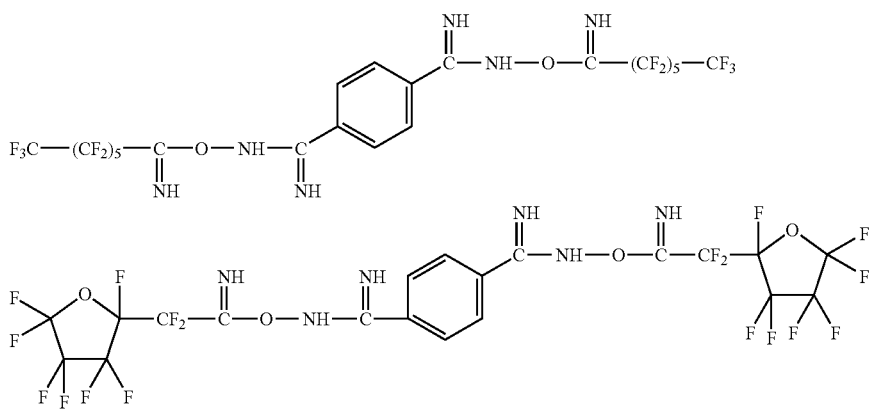

This article is hereby incorporated by reference in its entirety.

"Growth Inhibition and Induction of Cellular Differentiation of Human Myeloid Leukemia Cells in Culture by Carbamoyl Congeners of Ribavirin," Sanghvi, Yogesh S., et al., *Journal of Medicinal Chemistry* (1990), 33(1), 336-44

The above-named article discloses compounds having the following formula:

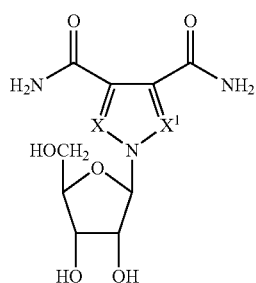

wherein either X=X1=N; X=N and X1=CH; X=X1=CH; or X=CNH2 and X1=N. In some embodiments, the compounds have one of the following formulae:

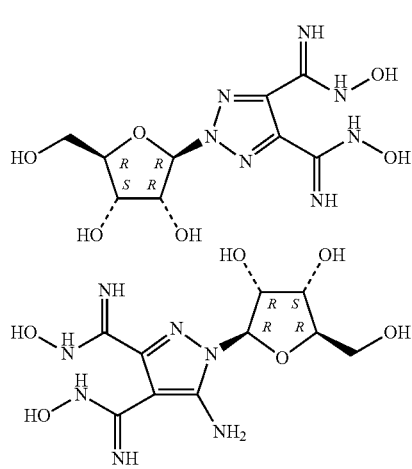

The above-named article is hereby incorporated by reference in its entirety.

French Patent No. 2601010 A1

The above-named French patent discloses compounds having the following formula:

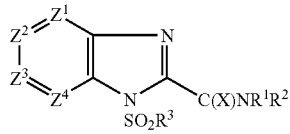

wherein $R^1$ and $R^2$ are separately selected from the group consisting of H, (un)substituted alkyl, cycloalkyl, aryl, aralkyl, alkoxy, alkanoyl, and aroyl; or $NR^1R^2$ may be an (un)substituted heterocyclyl; $R^3$ is selected from the group consisting of (un)substituted alkyl, cycloalkyl, $NH_2$; X=SO, $NOR^4$; $R^4$=H, alkyl, cycloalkyl, etc.; $Z^1$-$Z^4$=CH, CR, N; R=H, halo, alkyl, alkoxy, etc.

The above-named patent also describes compounds having the formula:

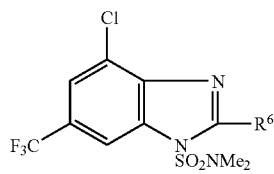

wherein $R^6$ is selected from the group consisting of cyano, $C(S)NH_2$, and $C(SO)NH_2$.

In some embodiments, the above-named patent describes compounds having the formula:

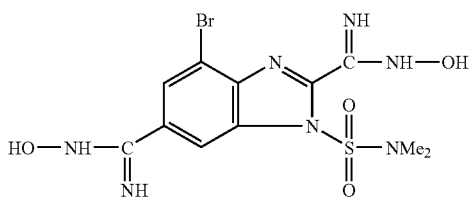

Methods for synthesizing the compounds disclosed above are described in French Patent No. 2601010 μl, which is hereby incorporated by reference in its entirety.

"Direct Synthesis of Pyrrole Nucleosides by the Stereospecific Sodium salt glycosylation procedure," Ramasamy, Kandasamy, *Journal of Heterocyclic Chemistry* (1987), 24(3), 863-8

The above-named article describes compounds have the formula:

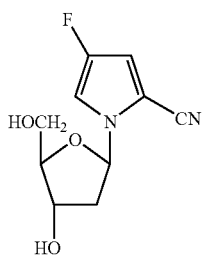

wherein R is H or cyano.

In another embodiment, the above-named article describes compounds having the formula:

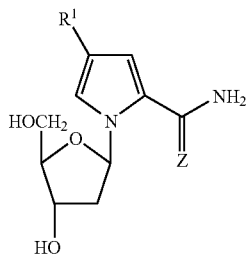

wherein $R^1$=H and Z=O, S, or NOH; or $R^1$=CONH$_2$ and Z=O; or $R^1$=CSNH$_2$ and Z=S; or $R^1$=C(NOH)NH$_2$ and Z=NOH.

In some embodiments, the above-named article discloses compounds having the structure:

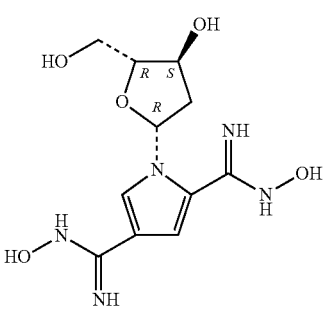

Methods for synthesizing the compounds disclosed above are described in the above-named article, which is hereby incorporated by reference in its entirety.

"Synthesis of Pyridyloxadiazoles, 2,2-(Oxadiazolyl) Pyridines and 2,6-Bis(Oxadiazolyl)Pyridines as Analogs of Pyridinolcarbamate," Suarez, cecilia, et al., *Journal of Heterocyclic Chemistry* (1978), 15(7), 1093-6

The above-named article discloses compounds having the following formulae:

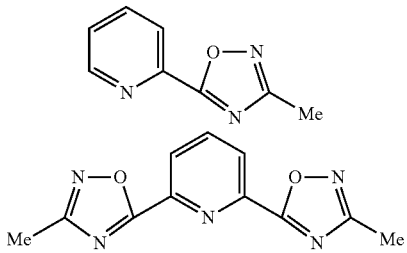

The above-named article is hereby incorporated by reference in its entirety.

"Hydroxylamine Derivatives as Potential Antimalarial Agents. 3. 1,2,4-Oxadiazoles," Hynes, John B., et al. *Journal of Medicinal Chemistry* (1972), 15(11), 1198-1200

The above-named article discloses the compound having the formula:

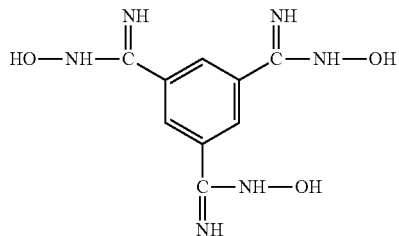

The above-named article is hereby incorporated by reference in its entirety.

"Picrylamino-Substituted Heterocycles. II. Furazans," Coburn, Michael D. *Journal of Heterocyclic Chemistry* (1968) 5(1), 83-7

The above-named article discloses the compound having the formula:

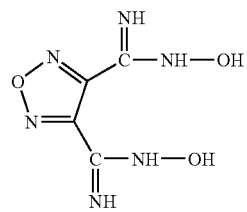

The above-named article is hereby incorporated by reference in its entirety.

"Structure-Activity Relationships of Analogs of Pentamidine Against *Plasmodium falciparum* and *Leishmania Mexicana Amazonensis*," Bell, Constance A., et al., *Antimicrobial Agents and Chemotherapy*, July 1990, pp. 1381-1386

The above-named article discloses compounds having the formula:

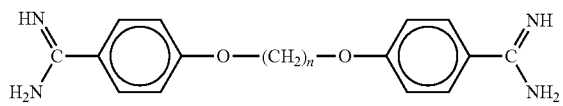

wherein n is from 2 to 6.

In another embodiment, the above-named article discloses compounds having the formula:
wherein n is from 3 to 6.

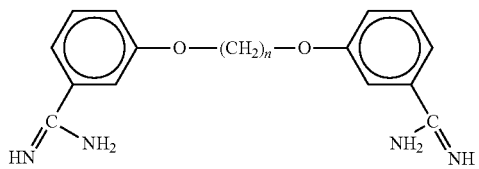

In another embodiment, the above-named article discloses compounds having the formula:

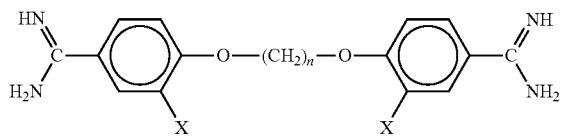

wherein n is from 2 to 5 and X may be $NO_2$ when n is 2, 4, or 5; X may be $NH_2$ when n is 2, 3, or 4; X may be $OCH_3$ when n is 3, 4, or 5; X may be Cl when n is 4 or 5; and X may be Br when n is 5.

In another embodiment, the above-named article discloses compounds having the formula:

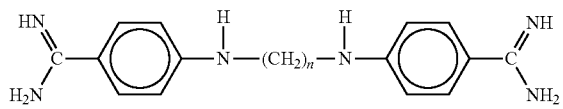

wherein n is from 3 to 6.

In another embodiment, the above-named article discloses compounds having the formula:

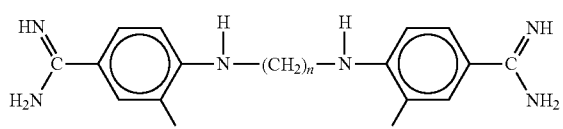

wherein n is from 2 to 6 and when n is 2, 4, 5 or 6, X is $NH_2$ and when n is 3 or 5, X1 $NO_2$.

In another embodiment, the above-named article discloses compounds having the formula:

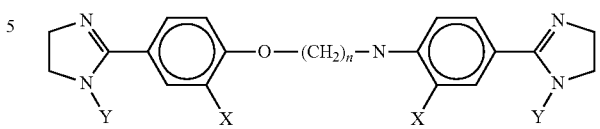

wherein n is from 3 to 5, X is H or $OCH_3$, and Y is H.

The above-named article is hereby incorporated by reference in its entirety.

PCT International Application No. WO 01/30757

The above-named PCT application discloses efflux pump inhibitors having the formula:

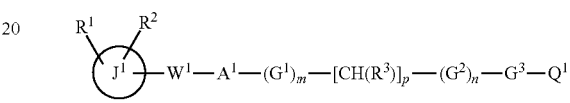

wherein $R^1$ and $R^2$ independently represent each hydrogen, halogeno, carboxy, etc.; $J^1$ represents 5- or 6-membered heteroaryl; $W^1$ represents —CH=CH—, —CH≡CH—, —$CH_2CH_2$—, etc.; $A^1$ represents phenylene, pyridinedyl, furandyl, etc.; $G^1$ represents oxygen, carbonyl, ethynyl, etc.; p is an integer of from 0 to 3; $G^2$ represents phenylene, furandyl, tetrahydrofurandyl, etc.; $G^3$ represents —$CH_2$— or a single bond; m and n represent each an integer of 0 or 1; and $Q^1$ represents an acidic group. PCT Application No. WO 01/30757 is hereby incorporated by reference in its entirety.

PCT International Patent Application No. WO 02/087589

The above-named PCT application describes efflux pump inhibitors having the formula:

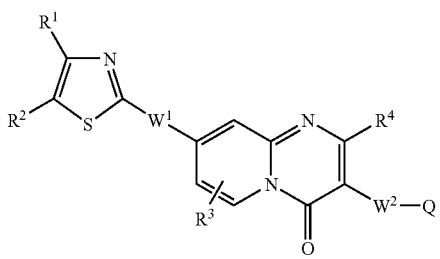

wherein $R^1$ and $R^2$ each represent hydrogen, a halogen atom, a hydroxyl group or the like; $W^1$ represents —CH=CH—, —$CH_2O$—, —$CH_2CH_2$— or the like; $R^3$ represents hydrogen, a halogen atom, a hydroxyl group or an amino group; $R^4$ represents hydrogen, a group of —$OZ_{0-4}R^5$ (where $Z_{0-4}$ represents an alkylene group or a fluorine-substituted alkylene group or a single bond and $R^5$ represents a cyclic alkyl group, an aryl group or the like) or the like; $W^2$ represents a single bond or —$C(R^8)$=$C(R^9)$— (where $R^8$ and $R^9$ each represent hydrogen, a halogen atom, a lower alkyl group or the like) and Q represents an acidic group, with the proviso that $W^2$ and Q may together form a heterocyclic ring of vinylidene thiazolidinedione or an equivalent thereof; m and n each represent an integer of 0 to 2 and q represents an integer of 0 to 3.

PCT Application No. WO 02/087589 is hereby incorporated by reference in its entirety.

"Synthesis and Anti-*Pneumocystis carinii* Activity of Conformationally Restricted Analogues of Pentamidine," Tao, Bin, et al., *European Journal of Medicinal Chemistry* (1999), 34(6), 531-538

The above-named article discloses compounds having the following structures:

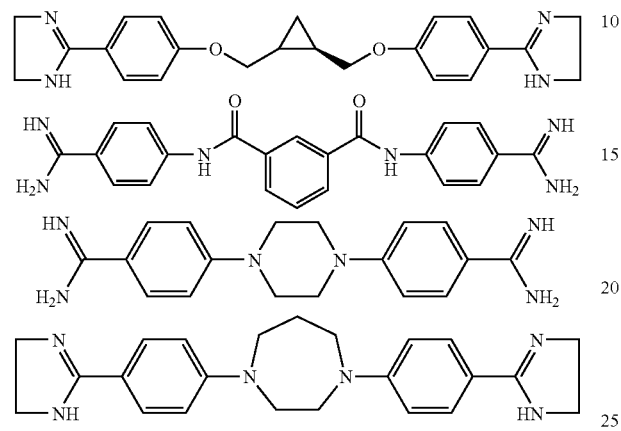

The article is hereby incorporated by reference in its entirety.

"Structure-In Vitro Activity Relationships of Pentamidine Analogs and Dication-Substituted Bis-Benzimidazoles as New Antifungal Agents," Del Poeta, Maurizio, et al., *Antimicrobioal Agents and Chemotherapy* (1998), 42(10), 2495-2502

The above-named article discloses compounds having the following structures:

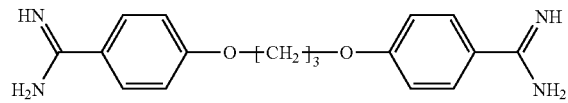

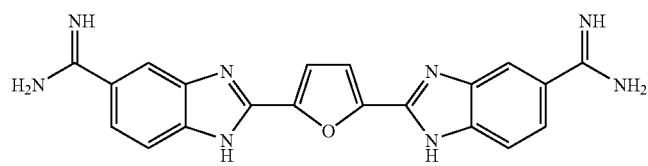

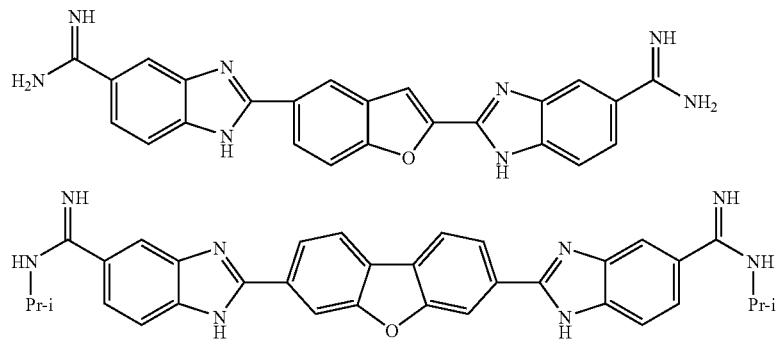

"Synthesis, Characterization, and Structure-Activity Relationships of Amidine-Substituted (Bis) Benzylidene-Cycloketone Olefin Isomers As Potent and Selective Factor XA Inhibitors," Guilford, William J., et al., *Journal of Medicinal Chemistry* (1999), 42(26), 5415-5425

The above-named article discloses compounds having the following structures:

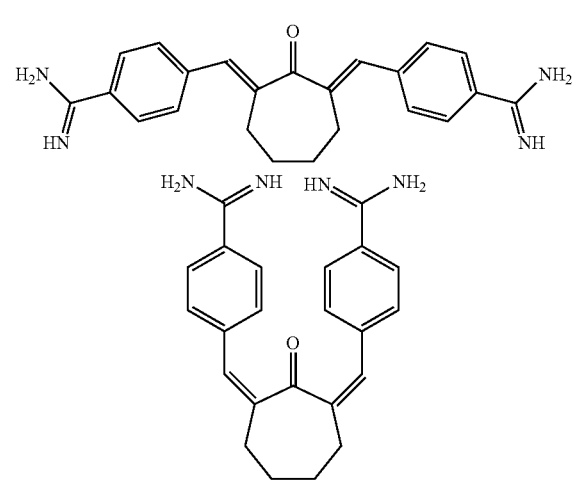

The article is hereby incorporated by reference in its entirety.

"Derivatives of 5-Amidine Indole as Inhibitors of Thrombin Catalytic Activity," Iwanowicz, Edwin J., et al., *Bioorganic & Medicinal Chemistry Letters* (1996), 6(12), 1339-1344

The above-named article discloses compounds having the structure:

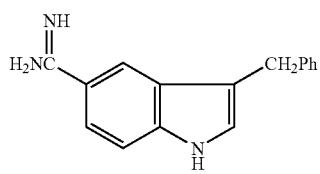

The article is hereby incorporated by reference in its entirety.

"On the Structure-Activity Relationship of Histamine H2-Receptor Antagonists Based on the X-Ray Crystal Structures and 1H-NMR Spectra of Amidine Derivatives," Ishida, Toshimasa, et al., *Molecular Pharmacology* (1987), 31(4), 410-16

The above-named article discloses compounds having the structure:

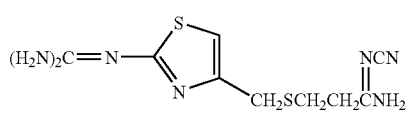

The article is hereby incorporated by reference in its entirety.

"Structure-Activity Relationships in Distamycin a Analogs: Effect of Alkyl Groups on the Pyrrole Nitrogen at the Non-Amidine End of the Molecule Combined with Methyl Elimination in the Following Ring," Grehn, Leif, et al., *Acta Chemica Scandinavica, Series B: Organic Chemistry and Biochemistry* (1986), B40(2), 145-51

The above-named article discloses compounds having the structure:

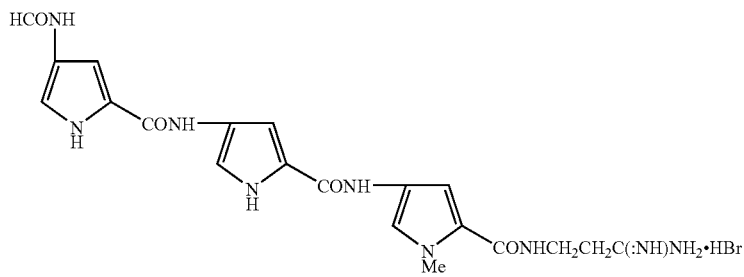

The article is hereby incorporated by reference in its entirety.

"Inhibitory Activity of Diarylamidine Derivatives on Murine Leukemia L1210 Cell Growth," Balzarini, Jan, et al., *Investigational New Drugs* (1983), 1(2), 103-15

The above-named article describes compounds having the following formula:

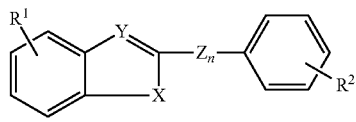

wherein X=NH, O S, $SO_2$, or $CH_2$; Y=CH, $CNH_2$, N, etc.; $R^1$ and $R^2$ separately are amidino, imidazolino, etc.; Z=CH: CH, PhO, CONH, NH, etc; and n=0 or 1.

In another embodiment, the above-named article describes compounds having the formula:

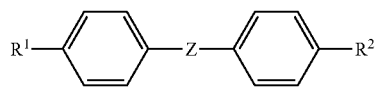

wherein $R^1$ and $R^2$=amidino or imidazolino and Z=CH:CH, NHN:N, etc.

In another embodiment, the above-named article describes compounds having the formula:

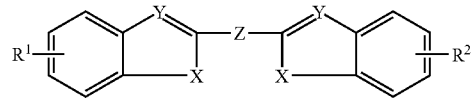

wherein X=O, S or NH; Y=CH, CMe, or N; and $R^1$ and $R^2$=amidino or imidazolino.

In another embodiment, the above-named article describes compounds having the formula:

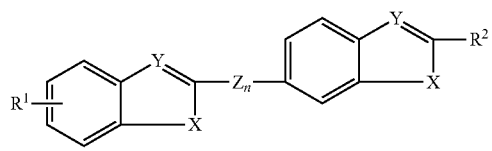

wherein X=NH; Y=CH; Z=CH:CH; $R^1$ and $R^2$=imidazolino; and n=0 or 1.

The above-named article is hereby incorporated by reference in its entirety.

"Structure-Activity Relationships of Pyrrole Amidine Antiviral Antibiotics. III: Preparation of Distamycin and Congocidine Derivatives Based on 2,5-Disubstituted Pyrroles," Bialer, Meir, et al., *Journal of Pharmaceutical Sciences* (1980), 69(11), 1334-8

The above-named article discloses compounds having the formula:

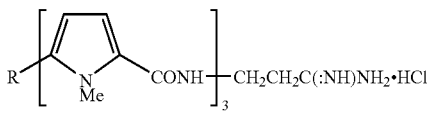

wherein R=NO$_2$ or HCONH.

In another embodiment, the above-named article discloses compounds having the formula:

wherein R$^1$=NO$_2$, H$_2$NC(:NH)NHCH$_2$CONH.

"Structure-Activity Relationships of Pyrrole Amidine Antiviral Antibiotics. 2. Preparation of Mono- and Tripyrrole Derivatives of Congocidine," Bialer, Meir, et al., *Journal of Medicinal Chemistry* (1980), 23(10), 1144-8

The above-named article discloses the compound having the following formula:

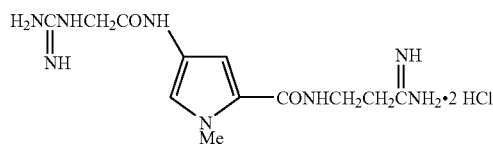

In another embodiment, the above-named article discloses compounds having the formula:

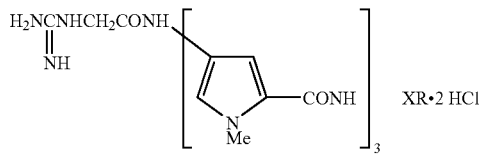

wherein R is C(:NH)NH$_2$ or CN and X is CH$_2$, CH$_2$CH$_2$, or CHMeCH$_2$.

Methods for synthesizing the compounds disclosed above are described in the above-named article, which is hereby incorporated by reference in its entirety.

"Synthesis of Bis-Substituted Amidinobenzothiazoles as Potential Anti-Hiv Agents," Racane, Livio, et al., *Heterocycles* (2001), 55(11), 2085-2098

The above-named article describes compounds have the formula:

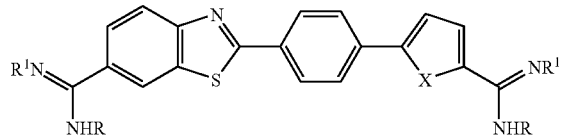

wherein X=O, S; R=Me$_2$CH; R$^1$=H or RR$^1$=CH$_2$CH$_2$.

In another embodiment, the above-named article describes compounds having the formula:

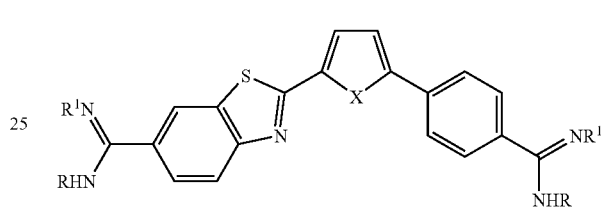

wherein X=O, S; R=Me$_2$CH; R$^1$=H or RR$^1$=CH$_2$CH$_2$.

In another embodiment, the above-named article describes compounds having the formula:

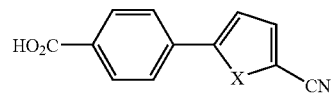

wherein X=O or S.

In another embodiment, the above-named article describes compounds having the formula:

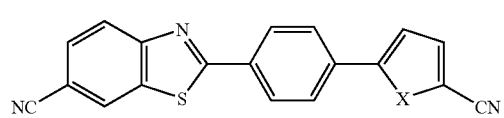

wherein X=O or S.

In another embodiment, the above-named article describes compounds having the formula:

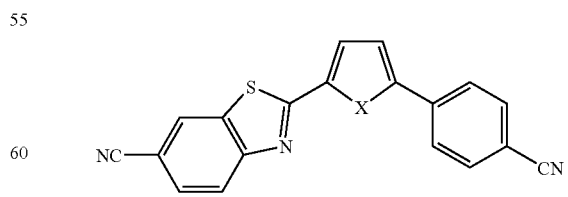

wherein X=O or S.

Methods for synthesizing the compounds disclosed above are described in the above-named article, which is hereby incorporated by reference in its entirety.

"Noncovalent Interactions Between Tetrazole and an N,N'-Diethyl-Substituted Benzamidine," Peters, Lars, et al., *Journal of Organic Chemistry* (2001), 66(10), 3291-3298

The above-name article discloses compounds having the following formulas:

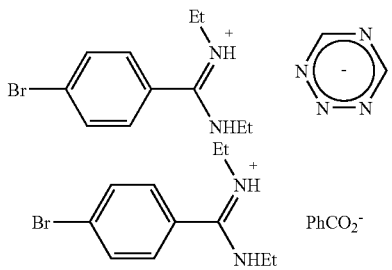

The article is hereby incorporated by reference in its entirety.
PCT International Application No. WO 98/07420 A1
The above-named PCT application describes compounds having the formula:

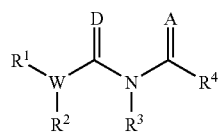

wherein A=O, S, or NR; R=$C_{1-8}$ alkyl; D=O, S, or $NR^7$; W=N, CH, or $CR^8$; $R^1$ and $R^3$ are independently H, (un)substituted, straight or branched, cyclic or acyclic satd., or unsatd. $C_{1-14}$ alkyl; $R^2$=Q($X^3$)—$NR^5$—$W^2$—$R^6$; $W^2$=CO, $SO_2$, CONH, S(O), or single bond; Q=(un) substituted $(CH_2)_z$, $(CH_2)_m$-$Q^1$-$(CH_2)_l$, z=1-12; when z>1, one or more $CH_2$ groups may be replaced by O, S, or substituted N; l and m are independently 0-5; $Q^1$=$C_{3-12}$ (un)satd. carbocyclic or heterocyclic ring; $X^3$=H, $C_{1-8}$ alkyl, aryl, $C_{1-8}$ alkoxy, OH, $CF_3$, etc; $R^4$=$NR^9R^{10}$, or $NR^{11}$—C(:$A^1$)-$NR^9R^{10}$; $A^1$=O, S, NH, or $R^{12}$; $R^{12}$=H, $C_{1-8}$ alkyl, or aryl; $R^5$-$R^9$, $R^{11}$, and $R^{12}$ are independently any group $R^1$, aryl, or heteroaryl; $R^{10}$=H, straight or branched, cyclic or acyclic, satd. or unsatd. $C_1$-$C_{12}$ alkyl, (un)substituted aryl, arloxyalkyl, 2- or 3-tetrahydrofurfuryl, $(CH_2)_{2-12}$—OH, amidoalkyl; $NR^9R^{10}$=3-10-membered ring; pure or partially separated stereoisomers or racemic mixtures thereof, and free bases or pharmaceutically acceptable derivatives thereof.
PCT Application No. WO 98/07420 A1 is hereby incorporated by reference in its entirety.

"Synthesis of Diphenyl Bisamidines as Potential Amebicides," Venugopalan, B., *European Journal of Medicinal Chemistry* (1996), 31(6), 485-488

The above-named article describes the compound of formula:

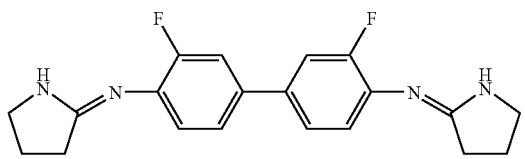

The article is hereby incorporated by reference in its entirety.

"Pentamidine Congeners. 2,2-Butene-Bridged Aromatic Diamidines and Diimidazolines as Potential Anti-*Pneumocystis carinii* Pneumonia Agents," Donkor, Isaac o., et al., *Journal of Medicinal Chemistry* (1994), 37(26), 4554-7

The above-named article describes compounds having the formula:

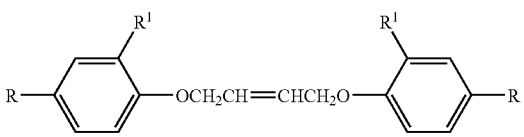

wherein R=C(:NH)$NH_2$ or 2-imidazolin-2-yl and $R^1$=H or OMe. The article is hereby incorporated by reference in its entirety.

"Synthesis of 1-Aryl-2-Arylamino-6-Aryliminotetrahydro-1,3,5-Triazine-4-Thiones from 6Asiv-2,5-Bisarylamino[1,2,4]Dithiazolo[2,3-B][1,2,4]Dithiazoles by Reaction with Amines," Joshua, C. P., et al. *Organic Chemistry Including Medicinal Chemistry* (1993), 32B(8), 879-81

The above-named article describes compounds having the following formulae:

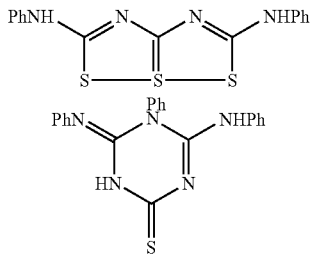

The article is hereby incorporated by reference in its entirety.

"Pentamidine Congeners. 1. Synthesis of Cis- and Trans-Butamidine Analogs as anti-*Pneumocystis carinii* Pneumonia Agents," Donkor, Isaac O., *Bioorganic & Medicinal Chemistry Letters* (1993), 3(6), 1137-40

The above-named article describes compounds having the formula:

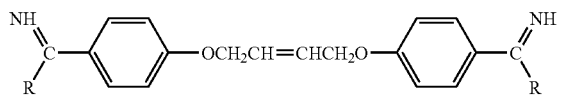

wherein R=$NH_2$. Also disclosed are compounds having the formula:

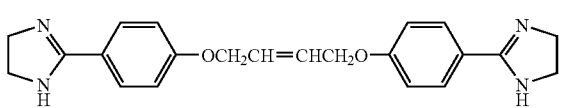

The article is hereby incorporated by reference in its entirety.

"Structure, DNA Minor Groove Binding, and Base Pair Specificity of Alkyl- and Aryl-Linked Bis(Amidinobenzimidazoles) and Bis(Amidinoindoles)," Fairley, Terri A., *Journal of Medicinal Chemistry* (1993), 36(12), 1746-53

The above-named article describes compounds having the formula:

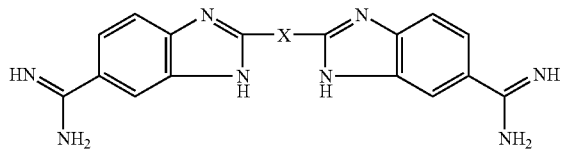

wherein $X=(CH_2)_n$ or phenylene and n=1-6.

In another embodiment, the above-named article describes compounds having the formula:

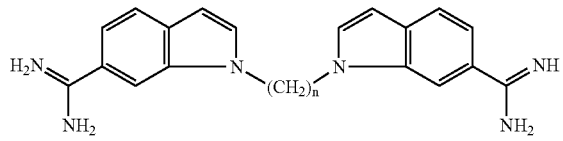

wherein n=3-6.

The above named article is hereby incorporated by reference in its entirety.

European Application No. 89-810491

The above-named European application describes compounds having the formula:

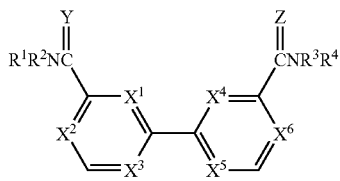

wherein one of $X_1$-$X_3$ and one of $X_4$-$X_6$ is CH and the others are CH or N; Y=O, S or $NR^5$; Z=O, S, or $NR^6$; $R^1$ and $R^3$ are H, alkyl, aryl, etc.; and $R^2$ and $R^4$-$R^6$ are H or alkyl. Alternatively, $NR^1R^2$ and $NR^3R^4$ are heterocyclyls.

The above-named application is hereby incorporated by reference in its entirety.

Indian Patent Application No. 157285 A

The above-named Indian patent application describes compounds having the formula:

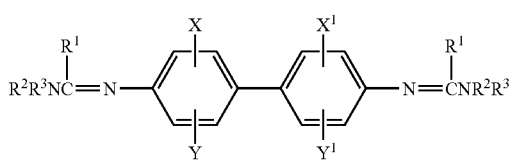

wherein X and $X^1$ are alkyl, alkoxy, halo, $CF_3$, $SO_3H$, $SO_2Me$, etc.; Y and $Y^1$ are halo, alkyl, etc.; $R^1$=H or (un)substituted alkyl; and $R^2$ and $R^3$=H, (un)substituted alkyl, or substituted acyl. Alternatively, $NR^2R^3$ may form a heterocycle and $R^1R^2$ may form an (un)substituted N-containing heterocycle.

Indian Patent Application No. 157285 A is hereby incorporated by reference in its entirety.

Indian Patent Application No. 155439 A

The above-named Indian patent application describes compounds having the formula:

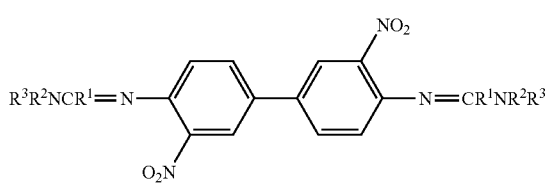

wherein $R^1$=H or alkyl; $R^2$ and $R^3$=H or alkyl. Alternatively, $R^2R^3N$ may form a heterocycle.

In another embodiment, the above-named application describes the compound having the formula:

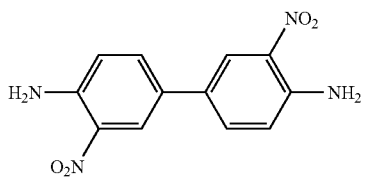

Indian Patent Application No. 155439 A is hereby incorporated by reference in its entirety.

German Patent Application No. DE 3343815 A1.

The above-named German patent application describes compounds having the formula:

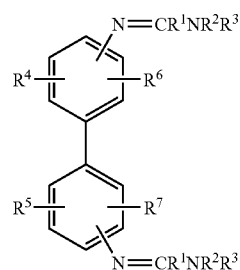

wherein $R^1$=H or (un)substituted $C_{1-5}$ alkyl; $R^2$ and $R^3$=H, (un)substituted $C_{1-5}$ alkyl, or $C_{1-5}$ alkanoyl; alternatively, $R^2R^3N$=heterocyclyl; alternatively, $R^1CNR^2$=heterocyclyl; alternatively, $R^3=R^2$ or $C_{2-5}$ carbalkoxy; $R^4$ and $R^5=C_{1-5}$ alkyl, alkoxy, halo, or $SO_2Me$; and $R^6$ and $R^7$=H or halo.

German Patent Application No. DE 3343815 A1 is hereby incorporated by reference in its entirety.

Indian Patent Application No. 153442

The above-named Indian patent application describes compounds having the formula:

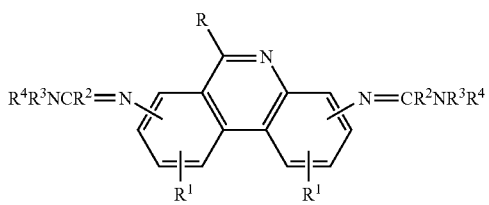

wherein R=H, halo, alkoxy, NH$_2$, monoalkylamino, dialkylamino, or N heterocyclyl optionally containing O, S, or N; R$^1$=H, alkyl, alkoxy, halo, NO$_2$, or NH$_2$; R$^2$=H, (un)substituted alkyl; R$^3$ and R$^4$=H or alkyl; alternatively, C(R$^2$)R$^3$N=heterocyclyl; alternatively, NR$^3$R$^4$=heterocyclyl.

Methods for synthesizing the above compounds are described in Indian Patent Application No. 153442, which is hereby incorporated by reference in its entirety.

German Patent Application No. DE 3305329 A1

The above-named German application describes compounds having the formula:

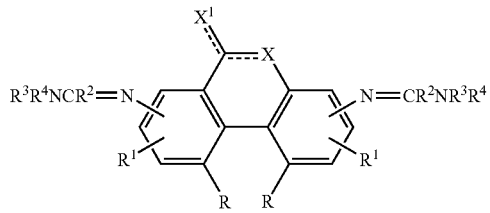

wherein R=H; R$^2$=OC(O); R$^1$=H, alkyl, alkoxy, halo, NO$_2$, or amino; R$^2$=H or (un)substituted alkyl; R$^3$ and R$^4$=alkyl; alternatively, R$^3$R$^4$N=heterocyclyl; X=O, N, NH; X$^1$=O. H, halo, alkoxy, amino heterocyclyl; and dotted lines represent optional double bonds.

German Patent Application No. DE 3305329 A1 is hereby incorporated by reference in its entirety.

"Synthesis of Bisamidine Derivatives of Diphenylamine as Potential Anthelmintic Agents," Shukla, J. S., et al., *Indian Journal of Chemistry, Section B: Organic Chemistry Including Medicinal Chemistry* (1981), 20B(12), 1072-4

The above-named article describes the compound of formula:

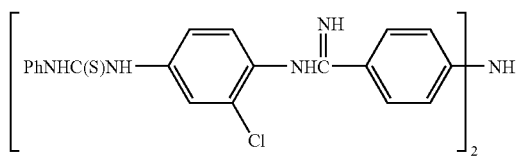

The article is hereby incorporated by reference in its entirety.

"Effect of Aromatic Bisamidines on Blood Coagulation and Fibrinolysis," Hauptmann, J., et al., *Acta Biologica Etmedica Germanica* (1976) 35(5), 635-44

The above-named article describes the compound of formula:

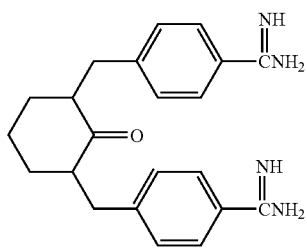

The article is hereby incorporated by reference in its entirety.

"Application of Molecular Topology to the Prediction of Antifungal Activity for a Set of Dication-Substituted Carbazoles, Furans and Benzimidazoles," Garcia-Domenech, et al. *Theochem* (2003), 624 97-107

The above-named article discloses compounds having the following formulae:

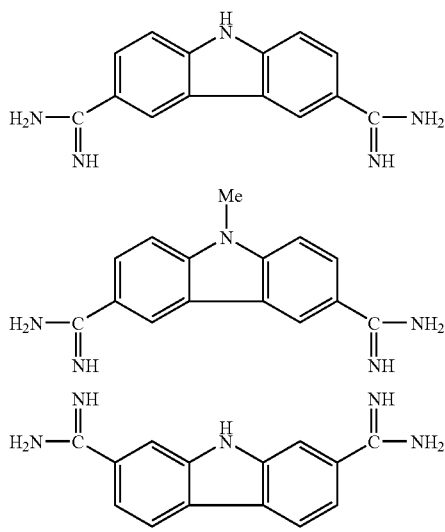

The article is hereby incorporated by reference in its entirety.

"Antileishmanial Activities of Several Classes of Aromatic Dications," Brendle, James J., et al., *Antimicrobial Agents and Chemotherapy* (2002), 46(3), 797-807

The above-named article discloses compounds having the following formulae:

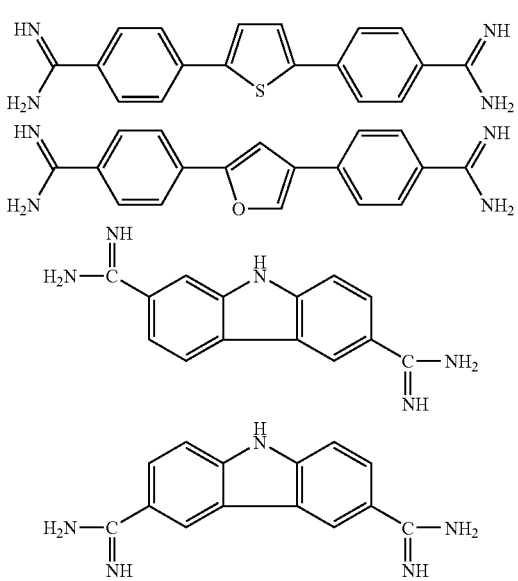

-continued

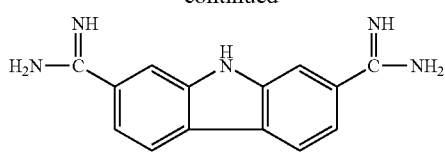

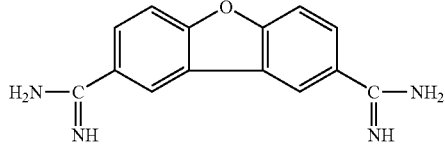

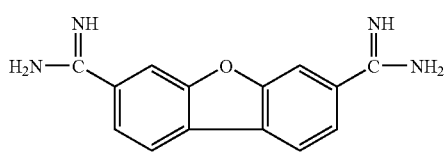

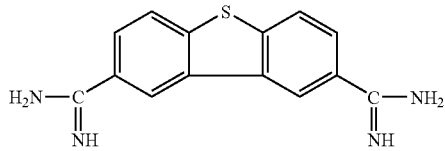

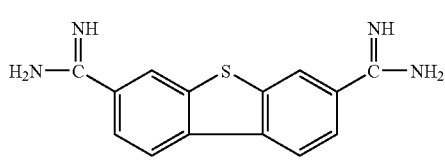

The article is hereby incorporated by reference in its entirety.

PCT International Application No. WO 2000/010990 A2

The above-named PCT application describes compounds having the formula:

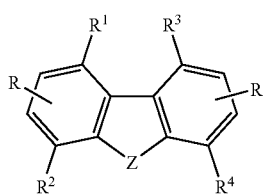

wherein each R is independently H, alkyl, alkoxy, or C(:NR$^5$)NR$^5$R$^6$; R$^1$-R$^4$=H, halo, alkyl, alkoxy, etc.; R$^5$=H, alkyl, alkoxy, aryl, etc.; alternatively, R$^5$R$^5$=alkylene, etc.; R$^6$=H, OH, alkyl, alkoxy, etc.; and Z=O or S.

PCT Application No. WO 2000/010990 A2 is hereby incorporated by reference in its entirety.

"Heterogeneity in the Actions of Drugs that Bind in the DNA Minor Groove," Albert, Fred G., et al., *Biochemistry* (1999), 38(31), 10135-10146

The above-named article describes the compound of formula:

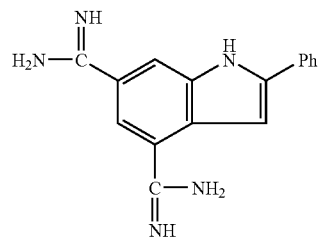

The article is hereby incorporated by reference in its entirety.

"In Vitro Antifungal Activities of a Series of Dication-Substituted Carbazoles, Furans, and Benzimidazoles," Del Poeta, Maurizio, et al., *Antimicrobial Agents and Chemotherapy* (1998), 42(10), 2503-2510

The above-named articled describes the compounds having the following formulae:

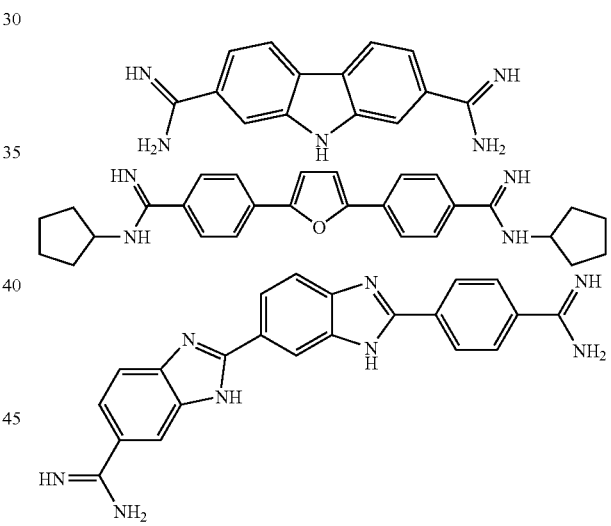

The article is hereby incorporated by reference in its entirety.

PCT International Application No. WO 96/40117 A1

The above-named PCT application describes compounds having the formula:

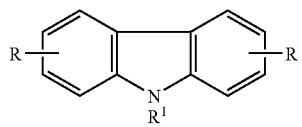

Wherein R=halo, alkyl, alkoxy, aryl, or C(:NR$^2$)NR$^2$R$^3$; R$^1$=halo, alkyl, aryl, etc.; R$^2$=H, alkyl, aryl, etc.; and R$^3$=H, OH, alkyl, aryl, etc.

PCT Application No. WO 96/40117 A1 is hereby incorporated by reference in its entirety.

"Effect of New Diamidines Against Leishmania Donovani Infection," Chauhan, P. M. S., et al., *Indian Journal of Experimental Biology* (1993), 31(2), 196-8

The above-named article describes the compounds having the following formulae:

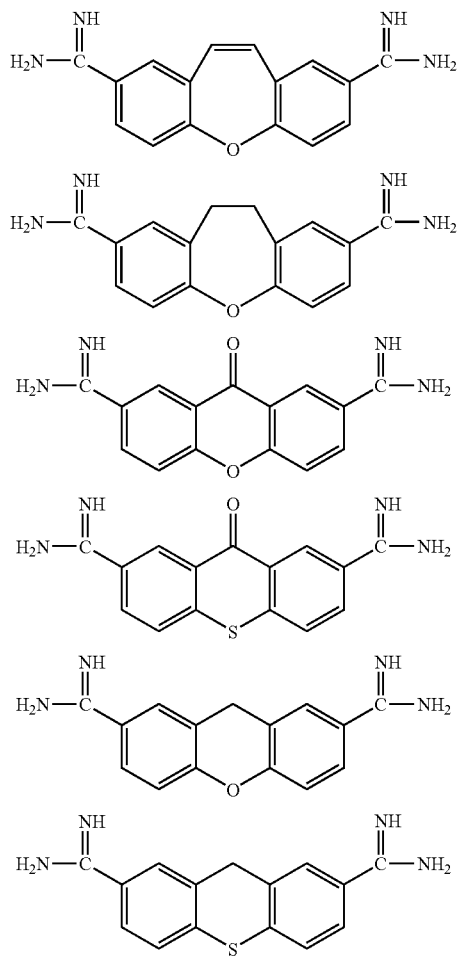

The article is hereby incorporated by reference in its entirety.

"Investigations on Mutagenicity and Genotoxicity of Pentamidine and Some Related Trypanocidal Diamidines," Stauffert, I., et al., *Mutation Research* (1990), 245(2), 93-8

The above-named article describes the compounds having the following formulae:

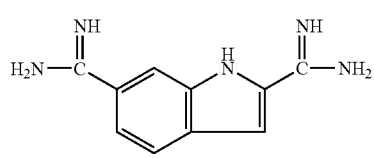

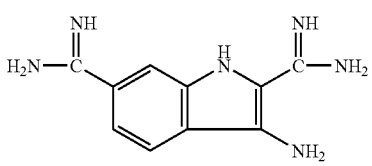

The article is hereby incorporated by reference in its entirety.

"Synthesis of 2,7-Diamidinoxanthone, Thioxanthone and Related Compounds as Potential Leishmanicides," Chauhan, P. M. S., et al., *Organic Chemistry Including Medicinal Chemistry* (1987), 26B(3), 248-50

The above-named article describes compounds having the formula:

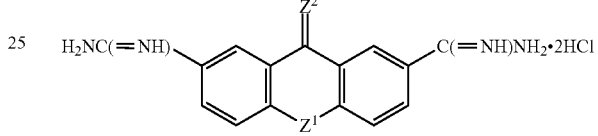

wherein $Z^1$=S or O and $Z^2$=O or is absent. The article is hereby incorporated by reference in its entirety.

"Inhibitory Activity of Diarylamidine Derivatives on Murine Leukemia L1210 Cell Growth," Balzarini, Jan, et al., *Investigational New Drugs* (1983), 1(2), 103-15

The above-named article describes compounds having the formula:

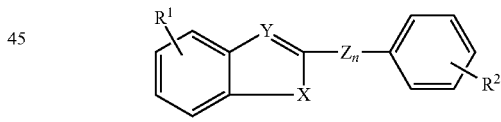

wherein X=NH, O, S $SO_2$, or $CH_2$; Y=CH, $CNH_2$, N, etc.; $R^1$ and $R^2$=amidino, imidazolino, etc.; Z=CH:CH, PhO, CONH, NH, etc.; and n=0 or 1.

In other embodiments, the above-named article describes compounds having the formula:

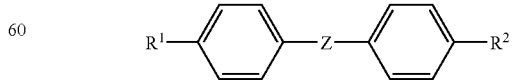

wherein $R^1$ and $R^2$=amidino or imidazolino and Z=CH:CH, NHN:N, etc.

In other embodiments, the above-named article describes compounds having the formula:

wherein X=O, S or NH; Y=CH, CMe, N; and R¹ and R²=amidino or imidazolino.

In other embodiments, the above-named article describes compounds having the formula:

wherein X=NH; Y=CH; Z=CH:CH; R1 and R2=imidazolino; and n=0 or 1.

The above-named article is hereby incorporated by reference in its entirety.

"Amino Derivatives of 9H-Fluorene," Ferranti, a., et al., *Farmaco, Edizione Scientifica* (1982), 37(3), 199-204

The above-named article describes compounds having the formula:

wherein X=O or is absent and R=R¹=amidino; alternatively, X=O, R=amidino, $CONH(CH_2)_nC(:NH)NH_2$, R¹=H, and n=2 or 3. The article is hereby incorporated by reference in its entirety.

"Antifungal and Antibacterial Activities of Diarylamidine Derivatives," Anne, Jozef, et al., *Antimicrobial Agents and Chemotherapy* (1980), 18(2), 231-9

The above-named article describes compounds having the following formulae:

wherein R¹ and R²=C(:NH)NH₂, imidazolino, etc.; X, X¹, and X²=NH, O, S, etc.; Y=CH, CNH₂, CMe, or N; Z=CH: CH, NHN:N, $C_6H_4O$, $NHCOC_6H_4CONH$, etc. The article is hereby incorporated by reference in its entirety.

"Diaryl Amidine Derivatives as Oncornaviral DNA Polymerase Inhibitors," De Clercq, e., et al., *Journal of Medicinal Chemistry* (1980), 23(7), 787-95

The above-named article describes the compounds having the following formulae:

The article is hereby incorporated by reference in its entirety.

Boykin, et al., *J. Med. Chem.* 41, 124-129 (1998)

The above-named article describes compounds having the formula:

wherein R is selected from the group consisting of H, Pr, i-Pr, c-Pr, c-pentyl, and i-amyl. The article is hereby incorporated by reference in its entirety.

*Biochemistry,* 40, 2511 (2001)

The above-named article describes the compound having the formula:

The article is hereby incorporated by reference in its entirety.
Other publications describing pentamidine analogs suitable for use as disclosed herein include: "2,4-Diphenyl Furan Diamidines as Novel Anti-*Pneumocystis carinii* Pneumonia Agents," Francesconi, et al., *J. Med. Chem.* 42:2260-2265, 1999; "Trypanocidal Activity of Conformationally Restricted Pentamidine Congeners," Donkor, et al., *J. Med. Chem.* 46:1041-1048 2003; "Antimicrobial Activity of the DNA Minor Groove Binders Furamidine and Analogs," Boykin, *J. Braz. Chem. Soc.*, 13(6):763-771, 2002; "Antileishmanial Activities of Several Classes of Aromatic Dications," Brendle, et al., *Antimicrobial Agents and Chemotherapy*, 46(3):797-807, March 2002; "Comparative Efficacy Evaluation of Dicationic Carbazole Compounds, Nitazoxanide, and Paromomycin against *Cryptosporidium parvum* Infections in a Neonatal Mouse Model," Blagburn, et al, *Antimocrobial Agents and Chemotherapy*, 42(11):2877-2882, November 1998; "Inhibitory effects of pentamidine analogues on protein biosynthesis in vitro," Bielawski, et al., 47(1):113-120, 2000; "Amoebicidal Efficiencies of Various Diamidines against Two Strains of *Acanthamoeba polyphaga*," Perrine, et al., *Antimicrobial Agents and Chemotherapy*, 39(2):339-342, February 1995; "Synthesis, and biological evaluation of new 1,3,4-thiadiazolium-2-phenylamine derivatives against *Leishmania amazonensis* promastigotes and amastigotes," da Silva, et al., *European Journal of Medicinal Chemistry*, 37:979-984, 2002; "Effect of amidine derivatives on nitric oxide production by *Leishmania amazonensis* promastigotes and axenic amastigotes," Genestra, et al., *Nitric Oxide*, 8:1-6, 2003; "Synthesis of Analogues of Pentamidine as Potential Anti-*Pneumocystis Carinii* Agents," Huang, et al., *Electronic Conference on Synthetic Organic Chemistry (ECSOC-5)*, http://www.mdpi.org/ecsoc-5.htm, September 2001; "Coordination chemistry of two-tricyclic bisamidines," Widlicka, et al., *Abstracts of Papers*, 224th ACS National Meeting, Boston, Mass., USA, Publisher: American Chemical Society, Washington D.C., Aug. 18-22, 2002; "Elongation factor 2 as a target for selective inhibition of protein synthesis in vitro by the novel aromatic bisamidine," Gajko-Galicka, et al., *Molecular and Cellular Biochemistry*, 223(1&2):159-164, 2002; "Bisamidino benzofuran compounds as sodium/proton exchanger subtype 3 (NHE-3) inhibitors," Gericke, et al., PCT International Application No. WO 2001/072742 A1, Oct. 4, 2001; DNA-binding properties and cytotoxicity of extended aromatic bisamidines in breast cancer MCF-7 cells," Bielawski, et al., *Polish Journal of Pharmacology*, 53(2):143-147, 2001; "Aromatic extended bisamidines: synthesis, inhibition of topoisomerases, and anticancer cytotoxicity in vitro," *Archiv der Pharmazie* (Weinheim, Germany), 334(7):235-240, 2001; "DNA-binding activity and cytotoxicity of the extended diphenylfuran bisamidines in breast cancer MCF-7 cells," Bielawski, et al., *Biological & Pharmaceutical Bulletin*, 24(6):704-706, 2001; "Preparation of bis(aminoalkyl- or amidinophenoxy)arylene- and heteroatom-interrupted alkanes and analogs as tryptase inhibitors," Anderskewitz, et al., German Patent Application No. DE 99-19955476, Nov. 18, 1999; "A COMFA study on antileishmaniasis bisamidines," Montanari, et al., *Molecular Modeling and Prediction of Bioactivity*, Proceedings of the European Symposium on Quantitative Structure-Activity Relationships: Molecular Modeling and Prediction of Bioactivity, 12th, Copenhagen, Denmark, Aug. 23-28, 1998 (2000); "Bis-Cationic heteroaromatics as macrofilaricides: synthesis of bis-amidine and bis-guanylhydrazone derivatives of substituted Imidazo[1,2-a]pyridines," Sundberg, et al., *Journal of Medicinal Chemistry*, 41(22):4317-4328, 1998; "Discovery of N-[2[5-[Amino(imino)methyl]-2-hydroxyphenoxy]-3,5-difluoro-6-[3-(4,5-dihydro-1-methyl-1H-imidazol-2-yl) phenoxy]pyridine-4-yl]-N-methylglycine (ZK-807834): A Potent, Selective, and Orally Active Inhibitor of the Blood Coagulation Enzyme Factor Xal," Phillips, et al., *Journal of Medicinal Chemistry*, 41(19):3557-3562, 1998; "Active site-directed thrombin inhibitors. II. Studies related to arginine/guanidine bioisosteres," St. Laurent, et al., *Biooganic & Medicinal Chemistry*, 3(8):1145-56, 1995; "Bis(5-amidino-2-benzimidazolyl)methane and related amidines are potent, reversible inhibitors of mast cell tryptases," Caughey, et al., *Journal of Pharmacology and Experimental Therapeutics*, 264(2):676-82, 1993; "Antiparasitic agents. Part VI. Synthesis of 1,2-, 1,3-, and 1,4-bis[4-substituted (aryloxy)]benzenes and their biological activities," Schauhan, P. M., et al., *Indian Journal of Chemistry*, Section B: Organic Chemistry Including Medicinal Chemistry, 27B(1):38-42, 1988; "Synthesis and study of the antileukemic activity of N,N'-substituted amidines and bisamidines," Dumont, et al., *Journal de Pharmacie de Belgique*, 40(6):373-86, 1985; "Antiprotozoal diamidines," Edward A. Glazer, U.S. Pat. No. 4,546,113, Oct. 8, 1985; "Aromatic extended bisamidines: synthesis, inhibition of topoisomerases, and anticancer cytotoxicity in vitro," Bielawski, K., et al., *Archiv der Pharmazie*, 334(7):235-40, July 2001; "Synthesis of antiproteolytically active 3,5-bis(4-amidinobenzyl)- and 3,5-bis(4-amidinobenzylidene)piperidone-(4) derivatives (author's transl.)," Richter, P., et al., *Die Pharmazie*, 35(2):75-77, February 1980; "Bisamidines of 2,6-diaminoanthraquinone as antiamebic agents," Fabio, P. F., et al., *Journal of Medicinal Chemistry*, 21(3):273-6, March 1978; "Synthetic inhibitors of serine proteinases. 11. Report: The inhibition of trypsin, plasmin and thrombin by new bisamidino compounds," Walsmann, P., et al., *Acta biologica et medica Germanica*, 35(2):K1-8, 1976; "Effects of compound Structure on Carbazole Dication-DNA Complexes: Tests of the Minor-Groove Complex Models," Tanious, et al., *Biochemistry*, 39(39):12091-12101, 2000; "Synthesis and anti-*Pneumocystis carinii* pneumonia activity of novel dicationic dibenzothiophenes and orally active prodrugs," Patrick, D. A., et al., *European Journal of Medicinal Chemistry*, 34(7&8):575-583, 1999; "Dicationic dibenzofuran derivatives as anti-*Pneumocystis carinii* pneumonia agents: synthesis, DNA binding affinity, and anti-*P. carinii* activity in an immunosuppressed rat model," Wang, S., et al., *European Journal of Medicinal Chemistry*, 34(3):215-224, 1999; "Anti-Pneumocystis activities of aromatic diamidoxime prodrugs," Hall, J. E., et al., *Antimicrobial Agents and Chemotherapy*, 42(3):666-674, 1998; "Anti-*Pneumocystis carinii* pneumonia activity of dicationic carbazoles," Patrick, D. A., et al., European Journal of Medicinal Chemistry, 32(10):781-793, 1997; "Pharmacokinetic properties of antileukemic and trypanocidal compounds with amidino and imidazolinyl groups," Gluth, W. P., et al., *arzneimittel-Forschung*, 34(11):1542-51, 1984; "Reduction of N-hydroxylated compounds: amidoximes (N-hydroxyamidines) as pro-drugs of amidines," Clement Bernd Pharmaceutical Institute, Univ. of Kiel, Germany, *Drug metabolism reviews*, 34(3):565-79, August 2002; "Trypanocidal Activity of Conformationally Restricted Pentamidine Congeners," Donkor, I. O., et al., *Journal of Medicinal Chemistry*, 46(6):1041-1048, 2003; "Trypanocidal activity of dicationic compounds related to pentamidine," Donkor, I. O., et al., *European Journal of Medicinal Chemistry*, 36(6): 531-538, 2001; "In vitro antimicrobial activity of aromatic diamidines and diimidazolines related to pentamidine," Donkor, I. O., et al., *European Journal of Medicinal Chemistry*, 34(7&8):639-643, 1999; "Diarylamidines and -imidazolines as NMDA receptor antagonists," Tao, B., et al., *Book of Abstracts, 216th ACS National Meeting, Boston*, MEDI-111, Aug. 23-27, 1998; "Inhibitory effects of pentamidine analogs on spermine stimulated ligand binding to the NMDA receptor complex," Donkor, I. O., et al., *Bioorganic &

*Medicinal Chemistry Letters,* 7(11):1455-1460, 1997; "Pentamidine congeners. 4. DNA binding affinity and anti-*Pneumocystis carinii* activity of butamidine analogs," Donkor, I. O., et al., *Bioorganic & Medicinal Chemistry Letters,* 6(16): 1967-70, 1996; "Structure-activity relationships of pentamidine analogs against *Giardia lamblia* and correlation of antigiardial activity with DNA-binding affinity," Bell, C. A., et al., *Antimicrobial Agents and Chemotherapy,* 35(6):1099-107, 1991; "Structure-activity relationships of analogs of pentamidine against *Plasmodium falciparum* and *Leishmania mexicana* amazonensis," Bell, C. A., et al., *Antimicrobial Agents and Chemotherapy,* 34(7):1381-6, 1990; "Analogs of 1,5-bis(4-amidinophenoxy)pentane (pentamidine) in the treatment of experimental *Pneumocystis carinii* pneumonia," Tidwell, R. R., et al., *Journal of Medicinal Chemistry,* 33(4): 1252-7, 1990; "Structure-activity relationships of pentamidine analogs against *Giardia lamblia* and correlation of antigiardial activity with DNA-binding affinity," Bell, C. A., et al., *Antimicrobial agents and chemotherapy,* 35(6):1099-107, June 1991; "Structure-activity relationships of analogs of pentamidine against *Plasmodium falciparum* and *Leishmania* mexicana amazonensis," Bell, C. A., et al., *Antimicrobial agents and chemotherapy,* 34(7):1381-6, July 1990; "Structure-activity studies of novel amidine analogues of chlorambucil: Correlation of cytotoxic activity with DNA-binding affinity and topoisomerase II inhibition," Bielawska, A., et al., *Archiv der Pharmazie* (Weinheim, Germany), 336(6-7):293-299, 2003; "Synthesis and structure-activity relationships of novel parenteral carbapenems, CS-023 (R-115685) and related compounds containing an amidine moiety," Kawamoto, I., et al., *Journal of Antibiotics,* 56(6):565-579, 2003; "Noncovalent tripeptidic thrombin inhibitors incorporating amidrazone, amine and amidine functions at P1," Lee, K., et al., *Bioorganic & Medicinal Chemistry Letters,* 12(7):1017-1022, 2002; "Benzoyl and cinnamoyl nitrogen mustard derivatives of benzoheterocyclic analogues of the tallimustine: synthesis and antitumor activity," Baraldi, P. G., et al., *Biooragnic & Medicinal Chemistry* 10(5):1611-1618, 2002; "Selective heterocyclic amidine inhibitors of human inducible nitric oxide synthase," Moormann, A. E., et al., *Bioorganic & Medicinal Chemistry Letters,* 11(19):2651-2653, 2001; "Preparation of carbohydrate amidine derivatives as glycosidase inhibitors," Sakata, K., et al., *Japanese Patent No. JP* 2001247589 A2, Sep. 11, 2001; "Development of serine protease inhibitors displaying a multicentered short (<2.3 ANG.) hydrogen bond binding mode: Inhibitors of urokinase-type plasminogen activator and factor Xa.," Verner, E., et al., *Journal of Medicinal Chemistry,* 44(17):2753-2771, 2001; "DNA-binding activity and cytotoxicity of the extended diphenylfuran bisamidines in breast cancer MCF-7 cells," Bielawski, K., et al., *Biological & Pharmaceutical Bulletin,* 24(6):704-706, 2001; "Effect of amidine derivatives on *Leishmania* amazonensis axenic amastigotes. Preliminary studies of structure-activity relationships," Canto-Cavalheiro, M. M., et al., *Arzneimittel-Forschung,* 50(10):925-928, 2000; "Rationally-designed guanidine and amidine fungicides," Liebeschuetz, J. W., et al., *Pesticide Science,* 50(3): 258-274, 1997; "Synthesis and biochemical activity of novel amidine derivatives as m1 muscarinic receptor agonists," Ojo, B., et al., *Bioorganic & Medicinal Chemistry,* 4(10):1605-1615, 1996; Bis(5-amidino-2-benzimidazolyl)methane and related amidines are potent, reversible inhibitors of mast cell tryptases," Caughey, G. H., et al., *Journal of Pharmacology and Experimental Therapeutics,* 264(2):676-82, 1993; "Structure-activity relationships among amidine acaricides and insecticides," Knowles, C. O., *Insectic. Mode Action,* pp. 243-77, 1982; "Structure-activity relations of amidine derivatives," Fastier, F. N., *Pharmacological Reviews,* 14:37-90, 1962; "Structure-activity studies of novel amidine analogues of chlorambucil: correlation of cytotoxic activity with DNA-binding affinity and topoisomerase II inhibition," Bielawska A., et al., *Archiv der Pharmazie,* 336(6-7):293-9, August 2003; "Development of serine protease inhibitors displaying a multicentered short (<2.3 A) hydrogen bond binding mode: inhibitors of urokinase-type plasminogen activator and factor Xa," Verner E., et al., *Journal of Medicinal Chemistry,* 44(17): 2753-71, 2001; "Synthesis, characterization, and structure-activity relationships of amidine-substituted (bis)benzylidene-cycloketone olefin isomers as potent and selective factor Xa inhibitors," Guilford, W. J., et al., *Journal of Medicinal Chemistry,* 42(26):5415-25, Dec. 30, 1999; "On the structure-activity relationship of histamine H2-receptor antagonists based on the X-ray crystal structures and 1H-NMR spectra of amidine derivatives," Ishida, T., et al., *Molecular Pharmacology,* 31(4):410-6, April 1987; "Structure-activity relationships in distamycin A analogues: effect of alkyl groups on the pyrrole nitrogen at the non-amidine end of the molecule combined with methyl elimination in the following ring," Grehn L., et al., *Acta chemica Scandinavica. Series B: Organic chemistry and biochemistry,* 40(2): 145-51, February 1986; "Quantitative structure-activity relationships and molecular graphics in ligand receptor interactions: amidine inhibition of trypsin," Recanatini M., et al., *Molecular Pharmacology,* 29(4):436-46, April 1986; "Structure-activity relationships of pyrrole amidine antiviral antibiotics III: preparation of distamycin and congocidine derivatives based on 2,5-disubstituted pyrroles," Bialer, M., et al., *Journal of Pharmaceutical Sciences,* 69(11):1334-8, November 1980; "Structure-activity relationships of pyrrole amidine antiviral antibiotics. 1. Modifications of the alkylamidine side chain," Bialer, M., et al., *Journal of Medicinal Chemistry,* 22(11): 1296-301, November 1979; "Oximes, amidoximes and hydroxamic acids as nitric oxide donors," Koikov, L. N., et al., *Mendeleev Communications,* (4): 165-168, 1998; "Anti-Pneumocystis activities of aromatic diamidoxime prodrugs," Hall, J. E., et al., *Antimicrobial Agents and Chemotherapy,* 42(3):666-674, 1998; "Hemodynamic effects of a series of new trypanocidal indoleamidino compounds," Steinmann, U., et al., *Drug Development Research,* 7(2):153-63, 1986; "Hydroxylamine derivatives as potential antimalarial agents. 2. Hydroxamates and amidoximes," Hynes, J. B., et al., *Journal of Medicinal Chemistry,* 15(11):1194-6, 1972; and "Cyclopolycondensations. IX. Syntheses of fully polyether-poly(1,2,4-oxadiazoles)," Dogoshi, N., et al., *Makromolekulare Chemie,* 108: 170-81, 1967; all of which are hereby incorporated by reference in their entirety.

Microbial Species

The microbial species to be inhibited through the use of an efflux pump inhibitor as described herein, can be from multiple bacterial groups or species. Non-limiting examples include one or more of the following: *Pseudomonas aeruginosa, Pseudomonas fluorescens, Pseudomonas acidovorans, Pseudomonas alcaligenes, Pseudomonas putida, Stenotrophomonas maltophilia, Burkholderia cepacia, Aeromonas hydrophilia, Escherichia coli, Citrobacter freundii, Salmonella typhimurium, Salmonella typhi, Salmonella paratyphi, Salmonella enteritidis, Shigella dysenteriae, Shigella flexneri, Shigella sonnei, Enterobacter cloacae, Enterobacter aerogenes, Klebsiella pneumoniae, Klebsiella oxytoca, Serratia marcescens, Francisella tularensis, Morganella morganii, Proteus mirabilis, Proteus vulgaris, Providencia alcalifaciens, Providencia rettgeri, Providencia stuartii, Acinetobacter calcoaceticus, Acinetobacter haemolyticus, Yersinia enterocolitica, Yersinia pestis, Yersinia pseudotuber-* culosis, *Yersinia intermedia, Bordetella pertussis, Bordetella parapertussis, Bordetella bronchiseptica, Haemophilus influenzae, Haemophilus parainfluenzae, Haemophilus haemolyticus, Haemophilus parahaemolyticus, Haemophilus ducreyi, Pasteurella multocida, Pasteurella haemolytica, Branhamella catarrhalis, Helicobacter pylori, Campylobacter fetus, Campylobacter jejuni, Campylobacter coli, Borrelia burgdorferi, Vibrio cholerae, Vibrio parahaemolyticus, Legionella pneumophila, Listeria monocytogenes, Neisseria gonorrhoeae, Neisseria meningitidis, Kingella, Moraxella, Gardnerella vaginalis, Bacteroides fragilis, Bacteroides distasonis, Bacteroides* 3452A homology group, *Bacteroides vulgatus, Bacteroides ovalus, Bacteroides thetaiotaomicron, Bacteroides uniformis, Bacteroides eggerthii, Bacteroides splanchnicus, Clostridium difficile, Mycobacterium tuberculosis, Mycobacterium avium, Mycobacterium intracellulare, Mycobacterium leprae, Corynebacterium diphtheriae, Corynebacterium ilcerans, Streptococcus pneumoniae, Streptococcus agalactiae, Streptococcus pyogenes, Enterococcus faecalis, Enterococcus faecium, Staphylococcus aureus, Staphylococcus epidermidis, Staphylococcus saprophyticus, Staphylococcus intermedius, Staphylococcus hyicus* subsp. *hyicus, Staphylococcus haemolyticus, Staphylococcus hominis,* or *Staphylococcus saccharolyticus.*

A particularly appropriate example of a microbe appropriate for the use of an efflux pump inhibitor disclosed herein is a pathogenic bacterial species, *Pseudomonas aeruginosa,* which is intrinsically resistant to many of the commonly used antibacterial agents. Exposing this bacterium to an efflux pump inhibitor can significantly slow the export of an antibacterial agent from the interior of the cell or the export of siderophores. Therefore, if an antibacterial agent is administered in conjunction with the efflux pump inhibitor, the antibacterial agent, which would otherwise be maintained at a very low intracellular concentration by the export process, can accumulate to a concentration that will inhibit the growth of the bacterial cells. This growth inhibition can be due to either bacteriostatic or bactericidal activity, depending on the specific antibacterial agent used. While *P. aeruginosa* is an example of an appropriate bacterium, other bacterial and microbial species may contain similar broad substrate pumps, which actively export a variety of antimicrobial agents, and thus can also be appropriate targets.

Antimicrobial Agents

In particular embodiments various antibacterial agents can be used in combination with the efflux pump inhibitors described herein. These include quinolones, tetracyclines, glycopeptides, aminoglycosides, β-lactams, rifamycins, macrolides/ketolides, oxazolidinones, coumermycins, chloramphenicol, and glycylcycline. In particular embodiments, an antibiotic of the above classes can be, for example, one of the following:

Beta-Lactam Antibiotics imipenem, meropenem, biapenem, cefaclor, cefadroxil, cefamandole, cefatrizine, cefazedone, cefazolin, cefixime, cefmenoxime, cefodizime, cefonicid, cefoperazone, cefo ranide, cefotaxime, cefotiam, cefpimizole, cefpiramide, cefpodoxime, cefsulodin, ceftazidime, cefteram, ceftezole, ceftibuten, ceftizoxime, ceftriaxone, cefuroxime, cefuzonam, cephaacetrile, cephalexin, cephaloglycin, cephaloridine, cephalothin, cephapirin, cephradine, cefmetazole, cefoxitin, cefotetan, azthreonam, carumonam, flomoxef, moxalactam, amidinocillin, amoxicillin, ampicillin, azlocillin, carbenicillin, benzylpenicillin, carfecillin, cloxacillin, dicloxacillin, methicillin, mezlocillin, nafcillin, oxacillin, penicillin G, piperacillin, sulbenicillin, temocillin, ticarcillin, cefditoren, SC004, KY-020, cefdinir, ceftibuten, FK-312, S-1090, CP-0467, BK-218, FK-037, DQ-2556, FK-518, cefozopran, ME1228, KP-736, CP-6232, Ro 09-1227, OPC-20000, LY206763

Macrolides azithromycin, clarithromycin, erythromycin, oleandomycin, rokitamycin, rosaramicin, roxithromycin, troleandomycin Ketolides telithromycin, cethromycin Quinolones amifloxacin, cinoxacin, ciprofloxacin, enoxacin, fleroxacin, flumequine, lomefloxacin, nalidixic acid, norfloxacin, ofloxacin, levofloxacin, lomefloxacin, oxolinic acid, pefloxacin, rosoxacin, temafloxacin, tosufloxacin, sparfloxacin, clinafloxacin, gatifloxacin, moxifloxacin; gemifloxacin; garenoxacin; PD131628, PD138312, PD140248, Q-35, AM-1155, NM394, T-3761, rufloxacin, OPC-17116, sitafloxacin (Sato, K. et al., 1992, Antimicrob Agents Chemother. 37:1491-98), DV-7751a (Tanaka, M. et al., 1992, Antimicrob. Agents Chemother. 37:2212-18), and (Kurosaka et al., *Interscience Conference on Antimicrobial Agents and Chemotherapy,* 2003, 43rd: Chicago (F-1061)).

Tetracyclines, Glycylcyclines and Oxazolidinones chlortetracycline, demeclocycline, doxycycline, lymecycline, methacycline, minocycline, oxytetracycline, tetracycline, tigecycline; linezolide, eperozolid Aminoglycosides amikacin, arbekacin, butirosin, dibekacin, fortimicins, gentamicin, kanamycin, meomycin, netilmicin, ribostamycin, sisomicin, spectinomycin, streptomycin, tobramycin Lincosamides clindamycin, lincomycin.

Methods of Treatment or Prophylaxis

It has been discovered that pentamidine, which is known to inhibit growth of various protozoal pathogens, such as Pneumocystis, *Trypanosoma* and *Leishmania,* also is capable of inhibiting cellular efflux pumps of bacteria or other microbes. Such efflux pumps export substrate molecules from the cytoplasm in an energy-dependent manner, and the exported substrate molecules can include antibacterial agents. Such efflux pump inhibitors are useful, for example, for treating microbial infections by reducing the export of a co-administered antimicrobial agent or by preventing the export of a compound synthesized by microbes (e.g., bacteria) to allow or improve their growth. While the endogenous substrates of efflux pumps are not yet identified, there are some indications that efflux pumps may be important for bacterial virulence. Thus, also disclosed herein are compositions that include such efflux pump inhibitors and methods for treating microbial infections using those compositions.

In some embodiments, a method is provided for treating a microbial infection in an animal, specifically including in a mammal, by treating an animal suffering from such an infection with an antimicrobial agent and an efflux pump inhibitor, which increase the susceptibility of the microbe for that antimicrobial agent. Such efflux pump inhibitors can be selected from any of the pentamidine or pentamidine analog compounds generically or specifically described herein. In this way a microbe involved in the infection can be treated using the antimicrobial agent in smaller quantities, or can be treated with an antimicrobial agent, which is not therapeutically effective when used in the absence of the efflux pump inhibitor. Thus, this method of treatment is especially appropriate for the treatment of infections involving microbial strains that are difficult to treat using an antimicrobial agent alone due to a need for high dosage levels (which can cause undesirable side effects), or due to lack of any clinically effective antimicrobial agents. However, it is also appropriate for treating infections involving microbes that are susceptible to particular antimicrobial agents as a way to reduce the dosage of those particular agents. This can reduce the risk of side effects. It is also appropriate for treating infections involving microbes that are susceptible to particular antimicrobial agents as a way of reducing the frequency of selection of resistant microbes. In particular embodiments the microbe is a bacterium, which may, for example, be from any of the groups or species indicated above.

In some embodiments, a method is provided for prophylactic treatment of a mammal. In this method, an antimicrobial agent and an efflux pump inhibitor is administered to a mammal at risk of a microbial infection, e.g., a bacterial infection. The efflux pump inhibitor can be selected from any of the pentamidine or pentamidine analog compounds generically or specifically described herein.

In some embodiments, a method is provided for enhancing the antimicrobial activity of an antimicrobial agent against a microbe, in which such a microbe is contacted with an efflux pump inhibitor, and an antibacterial agent. The efflux pump inhibitor can be selected from any of the pentamidine or pentamidine analog compounds generically or specifically described herein. In one embodiment, the efflux pump inhibitor is pentamidine. Thus, this method makes an antimicrobial agent more effective against a cell, which expresses an efflux pump when the cell is treated with the combination of an antimicrobial agent and an efflux pump inhibitor. In particular embodiments the microbe is a bacterium or a fungus, such as any of those indicated above; the antibacterial agent can be selected from a number of structural classes of antibiotics including, e.g., beta-lactams, glycopeptides, aminoglycosides, quinolones, oxazolidinones, tetracyclines, rifamycins, coumermycins, macrolides, and chloramphenicol. In particular embodiments an antibiotic of the above classes can be as stated above.

In other embodiments, a method is provided for suppressing growth of a microbe, e.g., a bacterium, expressing a multidrug resistance efflux pump. As illustrated by the case where the microbe is a bacterium, the method involves contacting that bacterium with an efflux pump inhibitor, in the presence of a concentration of antibacterial agent below the MIC of the bacterium. The efflux pump inhibitor can be selected from any of the pentamidine or pentamidine analog compounds generically or specifically described herein. This method is useful, for example, to prevent or cure contamination of a cell culture by a bacterium possessing an efflux pump. However, it applies to any situation where such growth suppression is desirable.

In some embodiments, any of the compounds generically or specifically described herein may be administered as an efflux pump inhibitor either alone or, in conjunction with another therapeutic agent. In some embodiments, any of the compounds generically or specifically described herein may be administered as an efflux pump inhibitor in conjunction with any of the antimicrobial agents specifically or generically described herein, as well as with any other antimicrobial agent useful against the species of microbe to be treated, when such microbe do not utilize an efflux pump resistance mechanism. In some embodiments, the antimicrobial agents are administered at their usual recommended dosages. In other embodiments, the antimicrobial agents are administered at reduced dosages, as determined by a physician. For all conventional antimicrobials on the market, and many in clinical development, dosage ranges and preferred routes of administration are well established, and those dosages and routes can be used in conjunction with the efflux pump inhibitors of the present invention. Reduced dosages of the antimicrobials are contemplated due to the increased efficacy of the antimicrobial when combined with an efflux pump inhibitor.

In various embodiments, one or more administrations of a compound disclosed herein is provided so as to achieve a delivered daily dose of at least about 5 mg, 10 mg, 15 mg, 40 mg, 60 mg, 80 mg, or 100 mg.

In some embodiments, a compound disclosed herein is administered along with an antimicrobial agent. The two agents may be administered in a predetermined ratio. For example, the agents may be administered in a 1:1 ratio, 1:2 ratio, 2:1 ratio, etc. The agents may be administered separately, together, simultaneously, or sequentially. The agents may be administered as a combined, fixed dosage form or as separate dosage forms.

In some embodiments, a subject is identified as infected with bacteria that are resistant to an antimicrobial agent. The subject may then be treated with the antimicrobial agent in combination with a compound disclosed herein. A subject may be identified as infected with bacteria that are resistant based on observing an ineffective response of the infection to the antimicrobial. Alternatively, the bacteria may be cultured and identified as a known resistant strain by appropriate microbiological techniques known in the art.

In some embodiments, a subject is identified as a subject that is infected with bacteria that are capable of developing resistance to an antimicrobial. The subject may then be treated with the antimicrobial agent in combination with a compound disclosed herein. A subject may be identified as infected with bacteria that are capable of developing resistance by diagnosing the subject as having symptoms that are characteristic a bacterial infection with a bacteria species known to have resistant strains or a with a bacteria that is a member of group that are known to have resistant strains. Alternatively, the bacteria may be cultured and identified as a species known to have resistant strains or a bacteria that is a member of group that are known to have resistant strains.

In some embodiments, an efflux pump inhibitor is administered at a level sufficient to overcome or suppress the emergence of efflux pump-mediated resistance in bacteria. In some embodiments, this level produces the effective efflux pump inhibitory concentration at the site of infection. In other embodiments, this level produces an effect equivalent to shutting down all efflux pumps in the bacteria.

In some embodiments, a subject is identified as a subject that is at risk of infection with bacteria. The subject may then be prophylactically treated with an efflux pump inhibitor and an antimicrobial agent in order to prevent infection with a resistant bacterial strain. For example, subjects in environments likely to have resistant bacteria, such as a hospital, may be prophylactically treated.

In some embodiments, a subject is treated with an efflux pump inhibitor that is not otherwise generally effective as an antimicrobial. Thus, for example, the MIC of the efflux pump inhibitor may be greater than about 32 µg/ml, 64 µg/ml, 128 µg/ml, or 256 µg/ml.

In some embodiments, the subject to which an efflux pump inhibitor is administered is a human. In other embodiments, the subject is a non-human vertebrate. In another embodiments, the subject is a non-mammal mammal, bird, fish, amphibian, or reptile.

Treatment of Ophthalmic Infections

In some embodiments, an efflux pump inhibitor disclosed herein is co-administered with an antimicrobial agent to an eye having a microbial infection. In some embodiments, the efflux pump inhibitor is selected such that it is capable of inhibiting efflux pumps in bacteria that cause ophthalmic infections. In various embodiments, the efflux pump inhibitor is propamidine, dibromopropamidine, or hexamidine. When used to treat an ophthalmic infection that employs efflux pump(s) as a resistance mechanism, these efflux pump inhibitors inhibit the activity of the pump(s) allowing a co-administered antimicrobial agent to achieve sufficient concentrations to inhibit the microbe and treat the infection. In some embodiments, the microbe is a bacteria and the antimicrobial agent is an antibacterial agent. In some embodiments, the microbe is a fungus and the antimicrobial agent is an antifungal agent. In some embodiments, the microbe is an amoeba and the antimicrobial agent is an antiameobic agent.

By non-limiting example, the combination of propamidine with levofloxacin, gatifloxacin, moxifloxcin, clinafloxacin, or tosufloxacin may be used to decrease the minimum inhibitory concentration (MIC) of these compounds to ophthalmic *Pseudomonas aeruginosa* isolates by 8-32 fold.

In some embodiments, ophthalmic pharmaceutical formulations are provided that include an efflux pump inhibitor capable of inhibiting efflux pumps in bacteria that cause ophthalmic infections along with an antibacterial agent. In some embodiments, both the efflux pump inhibitor and the antibacterial agent are in the same solution. One non-limiting example includes the efflux pump inhibitor and antimicrobial agent in a fixed ratio in solution (e.g., about 0.3% gatifloxacin plus 0.5% propamidine). The formulations may be administered by any suitable means including topically to the eye or by injection into the eye. For topical administration, the formulations may take the form of eye drops.

Treatment of Otic Infections

In some embodiments, an efflux pump inhibitor disclosed herein is co-administered with an antimicrobial agent to an ear having a microbial infection. By non-limiting example, microbial infections of the ear include otitis media, otitis external malignant otitis external and mastoiditis. In some embodiments, the efflux pump inhibitor is selected such that it is capable of inhibiting efflux pumps in bacteria that cause otic infections. In various embodiments, the efflux pump inhibitor is a diamidine, including but not limited to propamidine, pentamidine, dibromopropamidine, or hexamidine. When used to treat an otic infection that employs efflux pump(s) as a resistance mechanism, these efflux pump inhibitors inhibit the activity of the pump(s) allowing a co-administered antimicrobial agent to achieve sufficient concentrations to inhibit the microbe and treat the infection.

By non-limiting example, the combination of propamidine with levofloxacin, gatifloxacin, moxifloxcin, clinafloxacin, or tosufloxacin may be used to decrease the minimum inhibitory concentration (MIC) of these compounds to otic *Pseudomonas aeruginosa* isolates by 8-32 fold.

In some embodiments, otic pharmaceutical formulations are provided that include an efflux pump inhibitor capable of inhibiting efflux pumps in bacteria that cause otic infections along with an antibacterial agent. In some embodiments, both the efflux pump inhibitor and the antibacterial agent are in the same solution. One non-limiting example includes the efflux pump inhibitor and antimicrobial agent in a fixed ratio in solution. The formulations may be administered by any suitable means including topically to the ear or by injection into the ear. For topical administration, the formulations may take the form of ear drops or gel. Some embodiments include a kit comprising an ear dropper to facilitate administration of efflux pump inhibitors disclosed herein, either alone or in combination with an antimicrobial.

Screening for Efflux Pump Inhibitors

Potential efflux pump inhibitor compounds can be tested for their ability to inhibit multi-drug resistance efflux pumps of various microbes and to potentiate various antimicrobial agents by using the methods described herein as well as those known in the art. For example, strains of microbes known to overexpress efflux pumps may be treated with the antimicrobial agent with and without the test efflux pump inhibitor compound. A checkerboard assay may be used with varying concentrations of both antimicrobial agent and test compound to determine the relative concentrations at which potentiation is observed.

In one non-limiting example, treatment of *P. aeruginosa* with a test compound allows obtaining one or more of the following biological effects:

1) *P. aeruginosa* strains will become susceptible to antibiotics that could not be used for treatment of pseudomonas infections, or become more susceptible to antibiotics, become more susceptible to antibiotics currently used for treatment of pseudomonas infections.

2) *P. aeruginosa* strains which developed resistance to antibiotics currently used for treatment of pseudomonas infections will become susceptible to these antibiotics.

3) Inhibition of the pump will result in a decreased frequency of resistance development to antibiotic, which is a substrate of the pump.

Obtaining even one of these effects provides a potential therapeutic treatment for infections by this bacterium. Also, similar pumps are found in other microorganisms. Some or all of the above effects can also be obtained with those microbes, and they are therefore also appropriate targets for detecting or using efflux pump inhibitors.

Pharmaceutical Compositions

For purposes of co-administration of an EPI as described herein and another antimicrobial compound, the EPI may be administered by the same route as the other anti-bacterial compound, either simultaneously or sequentially. For example, both the EPI and the antimicrobial compound may be administered directly to the eye or ear.

In some embodiments, the EPI and other anti-bacterial compound to be co-administered are administered by separate routes. For example, the EPI may be administered directly to the eye or ear while the antimicrobial compound is administered by inhalation, i.v., i.m., or orally. Any other possible combination of separate route administration is also contemplated.

In some embodiments, an efflux pump inhibitor disclose herein is combined in a fixed combination with an antimicrobial agent. In some embodiments, the fixed combination includes the efflux pump inhibitor and antimicrobial agent packaged in separate containers (e.g., in separate eye or ear dropper containers). In other embodiments, the fixed combination includes the efflux pump inhibitor and antimicrobial agent being physically combined together in the same formulation (e.g., a combined, fixed dosage form).

Administration

The efflux pump inhibitors disclosed herein may be administered at a therapeutically effective dosage, e.g., a dosage sufficient to provide treatment for the disease states previously described. While human dosage levels have yet to be optimized for the compounds of the invention, generally, a daily dose of pentamidine and for most of the inhibitors described herein is from about 0.05 to 100 mg/kg of body weight, preferably about 0.10 to 10.0 mg/kg of body weight, and most preferably about 0.15 to 1.0 mg/kg of body weight. Thus, for administration to a 70 kg person, the dosage range would be about 3.5 to 7000 mg per day, preferably about 7.0 to 700.0 mg per day, and most preferably about 10.0 to 100.0 mg per day. The amount of active compound administered will, of course, be dependent on the subject and disease state being treated, the severity of the affliction, the manner and schedule of administration and the judgment of the prescribing physician; for example, a likely dose range for oral administration would be about 70 to 700 mg per day, whereas for intravenous administration a likely dose range would be about 700 to 7000 mg per day, the active agents being selected for longer or shorter plasma half-lives, respectively. Screening techniques described herein for pentamidine can be used with other efflux pump inhibitors described herein to establish the efficacy of those inhibitors in comparison to pentamidine, and the dosage of the inhibitor can thus be adjusted to achieve an equipotent dose to the dosages of pentamidine.

Administration of the compounds disclosed herein or the pharmaceutically acceptable salts thereof can be via any of the accepted modes of administration for agents that serve similar utilities including, but not limited to, orally, subcutaneously, intravenously, intranasally, topically, transdermally, intraperitoneally, intramuscularly, intrapulmonarilly, vaginally, rectally, or intraocularly (e.g., applied topically to the eye or injected into the eye). Oral and parenteral administration are customary in treating the indications that are the subject of the present invention.

Pharmaceutically acceptable compositions include solid, semi-solid, liquid and aerosol dosage forms, such as, e.g., tablets, capsules, powders, liquids, suspensions, suppositories, aerosols or the like. The compounds can also be administered in sustained or controlled release dosage forms, including depot injections, osmotic pumps, pills, transdermal (including electrotransport) patches, and the like, for prolonged and/or timed, pulsed administration at a predetermined rate. Preferably, the compositions are provided in unit dosage forms suitable for single administration of a precise dose.

The compounds can be administered either alone or more typically in combination with a conventional pharmaceutical carrier, excipient or the like (e.g., mannitol, lactose, starch, magnesium stearate, sodium saccharine, talcum, cellulose, sodium crosscarmellose, glucose, gelatin, sucrose, magnesium carbonate, and the like). If desired, the pharmaceutical composition can also contain minor amounts of nontoxic auxiliary substances such as wetting agents, emulsifying agents, solubilizing agents, pH buffering agents and the like (e.g., sodium acetate, sodium citrate, cyclodextrine derivatives, sorbitan monolaurate, triethanolamine acetate, triethanolamine oleate, and the like). Generally, depending on the intended mode of administration, the pharmaceutical formulation will contain about 0.005% to 95%, preferably about 0.5% to 50% by weight of a compound of the invention. Actual methods of preparing such dosage forms are known, or will be apparent, to those skilled in this art; for example, see Remington's Pharmaceutical Sciences, Mack Publishing Company, Easton, Pa.

In addition, the compounds can be co-administered with, and the pharmaceutical compositions can include, other medicinal agents, pharmaceutical agents, adjuvants, and the like. Suitable additional active agents include, for example, antimicrobial agents as described above. When used, other active agents may be administered before, concurrently, or after administration of an efflux pump inhibitor of the present invention. In some embodiments, an efflux pump inhibitor is co-administered with one or more other antimicrobial agents.

Thus, in the present invention, an efflux pump inhibitor compound as set forth herein can be administered through a first route of administration, and the antimicrobial agent can be administered through a second route. The blood levels of drugs are affected by the route of administration. Thus, in one preferred embodiment, when the efflux pump inhibitor is administered by a first route, and the antibiotic or antimicrobial through a second route, the dosages or dosage forms are adjusted, as appropriate, to match the pharmcokinetic profiles of each drug. This may also be done when both drugs are administered by the same route. In either event, conventional techniques, including controlled release formulations, timing of administration, use of pumps and depots, and/or use of biodegradable or bioerodible carriers can be used to match the pharmacokinetics of the two active moieties.

In one preferred embodiment, the compositions will take the form of a unit dosage form such as a pill or tablet and thus the composition may contain, along with the active ingredient, a diluent such as lactose, sucrose, dicalcium phosphate, or the like; a lubricant such as magnesium stearate or the like; and a binder such as starch, gum acacia, polyvinylpyrrolidine, gelatin, cellulose, cellulose derivatives or the like. In another solid dosage form, a powder, marume, solution or suspension (e.g., in propylene carbonate, vegetable oils or triglycerides) is encapsulated in a gelatin capsule. Unit dosage forms in which the two active ingredients (inhibitor and antimicrobial) are physically separated are also contemplated; e.g., capsules with granules of each drug; two-layer tablets; two-compartment gel caps, etc.

Liquid pharmaceutically administrable compositions can, for example, be prepared by dissolving, dispersing, etc. an active compound as defined above and optional pharmaceutical adjuvants in a carrier (e.g., water, saline, aqueous dextrose, glycerol, glycols, ethanol or the like) to form a solution or suspension. Injectables can be prepared in conventional forms, either as liquid solutions or suspensions, as emulsions, or in solid forms suitable for dissolution or suspension in liquid prior to injection. The percentage of active compound contained in such parenteral compositions is highly dependent on the specific nature thereof, as well as the activity of the compound and the needs of the subject. However, percentages of active ingredient of 0.01% to 10% in solution are employable, and will be higher if the composition is a solid, which will be subsequently diluted to the above percentages. In some embodiments, the composition will comprise 0.2-2% of the active agent in solution.

Pharmaceutical compositions for intraocular delivery include aqueous ophthalmic solutions of the active compounds in water-soluble form, such as eyedrops, or in gellan gum (Shedden et al., *Clin. Ther.*, 23(3):440-50 (2001)) or hydrogels (Mayer et al., *Opthalmologica*, 210(2):101-3 (1996)); ophthalmic ointments; ophthalmic suspensions, such as microparticulates, drug-containing small polymeric particles that are suspended in a liquid carrier medium (Joshi, A., *J. Ocul. Pharmacol.*, 10(1):29-45 (1994)), lipid-soluble formulations (Alm et al., *Prog. Clin. Biol. Res.*, 312:447-58 (1989)), and microspheres (Mordenti, *Toxicol. Sci.*, 52(1): 101-6 (1999)); and ocular inserts. All of the above-mentioned references, are incorporated herein by reference in their entireties. Such suitable pharmaceutical formulations are most often and preferably formulated to be sterile, isotonic and buffered for stability and comfort. As disclosed in Remington's Pharmaceutical Sciences, 18th Ed., Mack Publishing Co., Easton, Pa. (1990), which is incorporated herein by reference in its entirety, and well-known to those skilled in the art, suitable formulations are most often and preferably isotonic, slightly buffered to maintain a pH of 5.5 to 6.5, and may include antimicrobial preservatives and appropriate drug stabilizers. Pharmaceutical formulations for intraauricular delivery include suspensions and ointments for topical application in the ear. Common solvents for such aural formulations include glycerin and water.

Liposomal Compositions

In some embodiments, efflux pump inhibitors disclosed herein may be formulated into liposome particles. Lipids which are useful in the present invention can be any of a variety of lipids including both neutral lipids and charged lipids. Carrier systems having desirable properties can be prepared using appropriate combinations of lipids, targeting groups and circulation enhancers. Additionally, the compositions provided herein can be in the form of liposomes or lipid particles, preferably lipid particles. As used herein, the term "lipid particle" refers to a lipid bilayer carrier which "coats" a nucleic acid and has little or no aqueous interior. More particularly, the term is used to describe a self-assembling lipid bilayer carrier in which a portion of the interior layer comprises cationic lipids which form ionic bonds or ion-pairs with negative charges on the nucleic acid (e.g., a plasmid phosphodiester backbone). The interior layer can also comprise neutral or fusogenic lipids and, in some embodiments, negatively charged lipids. The outer layer of the particle will typically comprise mixtures of lipids oriented in a tail-to-tail fashion (as in liposomes) with the hydrophobic tails of the interior layer. The polar head groups present on the lipids of the outer layer will form the external surface of the particle.

Liposomal bioactive agents can be designed to have a sustained therapeutic effect or lower toxicity allowing less frequent administration and an enhanced therapeutic index. Liposomes are composed of bilayers that entrap the desired pharmaceutical. These can be configured as multilamellar vesicles of concentric bilayers with the pharmaceutical trapped within either the lipid of the different layers or the aqueous space between the layers.

By non-limiting example, lipids used in the compositions may be synthetic, semi-synthetic or naturally-occurring lipids, including phospholipids, tocopherols, steroids, fatty acids, glycoproteins such as albumin, negatively-charged lipids and cationic lipids. Phospholipids include egg phosphatidylcholine (EPC), egg phosphatidylglycerol (EPG), egg phosphatidylinositol (EPI), egg phosphatidylserine (EPS), phosphatidylethanolamine (EPE), and egg phosphatidic acid (EPA); the soya counterparts, soy phosphatidylcholine (SPC); SPG, SPS, SPI, SPE, and SPA; the hydrogenated egg and soya counterparts (e.g., HEPC, HSPC), other phospholipids made up of ester linkages of fatty acids in the 2 and 3 of glycerol positions containing chains of 12 to 26 carbon atoms and different head groups in the 1 position of glycerol that include choline, glycerol, inositol, serine, ethanolamine, as well as the corresponding phosphatidic acids. The chains on these fatty acids can be saturated or unsaturated, and the phospholipid can be made up of fatty acids of different chain lengths and different degrees of unsaturation. In particular, the compositions of the formulations can include dipalmitoylphosphatidylcholine (DPPC), a major constituent of naturally-occurring lung surfactant as well as dioleoylphosphatidylcholine (DOPC) and dioleoylphosphatidylglycerol (DOPG). Other examples include dimyristoylphosphatidylcholine (DMPC) and dimyristoylphosphatidylglycerol (DMPG) dipalmitoylphosphatidcholine (DPPC) and dipalmitoylphosphatidylglycerol (DPPG) distearoylphosphatidylcholine (DSPC) and distearoylphosphatidylglycerol (DSPG), dioleylphosphatidylethanolamine (DOPE) and mixed phospholipids like palmitoylstearoylphosphatidylcholine (PSPC) and palmitoylstearoylphosphatidylglycerol (PSPG), and single acylated phospholipids like mono-oleoyl-phosphatidylethanolamine (MOPE).

In a preferred embodiment, PEG-modified lipids are incorporated into the compositions of the present invention as the aggregation-preventing agent. The use of a PEG-modified lipid positions bulky PEG groups on the surface of the liposome or lipid carrier and prevents binding of DNA to the outside of the carrier (thereby inhibiting cross-linking and aggregation of the lipid carrier). The use of a PEG-ceramide is often preferred and has the additional advantages of stabilizing membrane bilayers and lengthening circulation lifetimes. Additionally, PEG-ceramides can be prepared with different lipid tail lengths to control the lifetime of the PEG-ceramide in the lipid bilayer. In this manner, "programmable" release can be accomplished which results in the control of lipid carrier fusion. For example, PEG-ceramides having $C_{20}$-acyl groups attached to the ceramide moiety will diffuse out of a lipid bilayer carrier with a half-life of 22 hours. PEG-ceramides having $C_{14}$- and $C_8$-acyl groups will diffuse out of the same carrier with half-lives of 10 minutes and less than 1 minute, respectively. As a result, selection of lipid tail length provides a composition in which the bilayer becomes destabilized (and thus fusogenic) at a known rate. Though less preferred, other PEG-lipids or lipid-polyoxyethylene conjugates are useful in the present compositions. Examples of suitable PEG-modified lipids include PEG-modified phosphatidylethanolamine and phosphatidic acid, PEG-modified diacylglycerols and dialkylglycerols, PEG-modified dialkylamines and PEG-modified 1,2-diacyloxypropan-3-amines. Particularly preferred are PEG-ceramide conjugates (e.g., PEG-Cer-$C_8$, PEG-Cer-$C_{14}$ or PEG-Cer-$C_{20}$) which are described in U.S. Pat. No. 5,820,873, incorporated herein by reference.

The compositions of the present invention can be prepared to provide liposome compositions which are about 50 nm to about 400 nm in diameter. One of skill in the art will understand that the size of the compositions can be larger or smaller depending upon the volume which is encapsulated. Thus, for larger volumes, the size distribution will typically be from about 80 nm to about 300 nm.

Surface Modifiers

Efflux pump inhibitors disclosed herein, in the presence or absence of antibiotic, may be prepared in a pharmaceutical composition with suitable surface modifiers which may be selected from known organic and inorganic pharmaceutical excipients. Such excipients include low molecular weight oligomers, polymers, surfactants and natural products. Preferred surface modifiers include nonionic and ionic surfactants. Two or more surface modifiers can be used in combination.

Representative examples of surface modifiers include cetyl pyridinium chloride, gelatin, casein, lecithin (phosphatides), dextran, glycerol, gum acacia, cholesterol, tragacanth, stearic acid, benzalkonium chloride, calcium stearate, glycerol monostearate, cetostearyl alcohol, cetomacrogol emulsifying wax, sorbitan esters, polyoxyethylene alkyl ethers (e.g., macrogol ethers such as cetomacrogol 1000), polyoxyethylene castor oil derivatives, polyoxyethylene sorbitan fatty acid esters (e.g., the commercially available Tweens® such as e.g., Tween 20® and Tween 80® (ICI Specialty Chemicals)); polyethylene glycols (e.g., Carbowaxs 3350® and 1450®, and Carbopol 934® (Union Carbide)), dodecyl trimethyl ammonium bromide, polyoxyethylenestearates, colloidal silicon dioxide, phosphates, sodium dodecylsulfate, carboxymethylcellulose calcium, hydroxypropyl cellulose (UPC, UPC-SL, and UPC-L), hydroxypropyl methylcellulose (UPMC), carboxymethylcellulose sodium, methylcellulose, hydroxyethylcellulose, hydroxypropylcellulose, hydroxypropylmethyl-cellulose phthalate, noncrystalline cellulose, magnesium aluminum silicate, triethanolamine, polyvinyl alcohol (PVA), polyvinylpyrrolidone (PVP), 4-(1, 1,3,3-tetaamethylbutyl)-phenol polymer with ethylene oxide and formaldehyde (also known as tyloxapol, superione, and triton), poloxamers (e.g., Pluronics F68® and F108®, which are block copolymers of ethylene oxide and propylene oxide); poloxamines (e.g., Tetronic 908®, also known as Poloxamine 908®, which is a tetrafunctional block copolymer derived from sequential addition of propylene oxide and ethylene oxide to ethylenediamine (BASF Wyandotte Corporation, Parsippany, N.J.)); a charged phospholipid such as dimyristoyl phophatidyl glycerol, dioctylsulfosuccinate (DOSS); Tetronic 1508® (T-1508) (BASF Wyandotte Corporation), dialkylesters of sodium sulfosuccinic acid (e.g., Aerosol OT®, which is a dioctyl ester of sodium sulfosuccinic acid (American Cyanamid)); Duponol P®, which is a sodium lauryl sulfate (DuPont); Tritons X-200®, which is an alkyl aryl polyether sulfonate (Rohm and Haas); Crodestas F-110®, which is a mixture of sucrose stearate and sucrose distearate (Croda Inc.); p-isononylphenoxypoly-(glycidol), also known as Olin-Log® or Surfactant 10-G® (Olin Chemicals, Stamford, Conn.); Crodestas SL-40® (Croda, Inc.); and SA9OHCO, which is C.sub.18H.sub.37 CH.sub.2 (CON (CH.sub.3)-CH.sub.2 (CHOH).sub.4 (CH.sub.20H).sub.2 (Eastman Kodak Co.); decanoyl-N-methylglucamide; n-decyl beta.-D-glucopyranoside; n-decyl beta.-D-maltopyranoside; n-dodecyl beta.-D-glucopyranoside; n-dodecyl beta.-D-maltoside; heptanoyl-N-methylglucamide; n-heptyl-.beta.-D-glucopyranoside; n-heptyl .beta.-D-thioglucoside; n-hexyl .beta.-D-glucopyranoside; nonanoyl-N-methylglucamide; n-noyl .beta.-D-glucopyranoside; octanoyl-N-methylglucamide; n-octyl-.beta.-D-glucopyranoside; octyl beta.-D-thioglucopyranoside; and the like. Tyloxapol is a particularly preferred surface modifier for the pulmonary or intranasal delivery of steroids, even more so for nebulization therapies.

Most of these surface modifiers are known pharmaceutical excipients and are described in detail in the Handbook of Pharmaceutical Excipients, published jointly by the American Pharmaceutical Association and The Pharmaceutical Society of Great Britain (The Pharmaceutical Press, 1986), specifically incorporated by reference. The surface modifiers are commercially available and/or can be prepared by techniques known in the art. The relative amount of drug and surface modifier can vary widely and the optimal amount of the surface modifier can depend upon, for example, the particular drug and surface modifier selected, the critical micelle concentration of the surface modifier if it forms micelles, the hydrophilic-lipophilic-balance (HLB) of the surface modifier, the melting point of the surface modifier, the water solubility of the surface modifier and/or drug, the surface tension of water solutions of the surface modifier, etc.

In the present invention, the optimal ratio of drug to surface modifier is ~0.1% to ~99.9% efflux pump inhibitor in the presence or absence of antibiotic, more preferably about 10% to about 90%.

Dispersion-Enhancing Peptides

Compositions may include one or more di- or tripeptides containing two or more leucine residues. By further non-limiting example, U.S. Pat. No. 6,835,372 disclosing dispersion-enhancing peptides, is hereby incorporated by reference in its entirety. This patent describes the discovery that dileucyl-containing dipeptides (e.g., dileucine) and tripeptides are superior in their ability to increase the dispersibility of powdered composition.

In another embodiment, highly dispersible particles including an amino acid are administered. Hydrophobic amino acids are preferred. Suitable amino acids include naturally occurring and non-naturally occurring hydrophobic amino acids. Some naturally occurring hydrophobic amino acids, including but not limited to, non-naturally occurring amino acids include, for example, beta-amino acids. Both D, L and racemic configurations of hydrophobic amino acids can be employed. Suitable hydrophobic amino acids can also include amino acid analogs. As used herein, an amino acid analog includes the D or L configuration of an amino acid having the following formula: —NH—CHR—CO—, wherein R is an aliphatic group, a substituted aliphatic group, a benzyl group, a substituted benzyl group, an aromatic group or a substituted aromatic group and wherein R does not correspond to the side chain of a naturally-occurring amino acid. As used herein, aliphatic groups include straight chained, branched or cyclic C1-C8 hydrocarbons which are completely saturated, which contain one or two heteroatoms such as nitrogen, oxygen or sulfur and/or which contain one or more units of desaturation. Aromatic groups include carbocyclic aromatic groups such as phenyl and naphthyl and heterocyclic aromatic groups such as imidazolyl, indolyl, thienyl, furanyl, pyridyl, pyranyl, oxazolyl, benzothienyl, benzofuranyl, quinolinyl, isoquinolinyl and acridintyl.

Suitable substituents on an aliphatic, aromatic or benzyl group include —OH, halogen (—Br, —Cl, —I and —F) —O (aliphatic, substituted aliphatic, benzyl, substituted benzyl, aryl or substituted aryl group), —CN, —NO.sub.2, —COOH, —NH.sub.2, —NH (aliphatic group, substituted aliphatic, benzyl, substituted benzyl, aryl or substituted aryl group), —N (aliphatic group, substituted aliphatic, benzyl, substituted benzyl, aryl or substituted aryl group).sub.2, —COO (aliphatic group, substituted aliphatic, benzyl, substituted benzyl, aryl or substituted aryl group), —CONH.sub.2, —CONH (aliphatic, substituted aliphatic group, benzyl, substituted benzyl, aryl or substituted aryl group)), —SH, —S (aliphatic, substituted aliphatic, benzyl, substituted benzyl, aromatic or substituted aromatic group) and —NH—C(.dbd.NH)—NH.sub.2. A substituted benzylic or aromatic group can also have an aliphatic or substituted aliphatic group as a substituent. A substituted aliphatic group can also have a benzyl, substituted benzyl, aryl or substituted aryl group as a substituent. A substituted aliphatic, substituted aromatic or substituted benzyl group can have one or more substituents. Modifying an amino acid substituent can increase, for example, the lypophilicity or hydrophobicity of natural amino acids which are hydrophilic.

A number of the suitable amino acids, amino acids analogs and salts thereof can be obtained commercially. Others can be synthesized by methods known in the art.

Hydrophobicity is generally defined with respect to the partition of an amino acid between a nonpolar solvent and water. Hydrophobic amino acids are those acids which show a preference for the nonpolar solvent. Relative hydrophobicity of amino acids can be expressed on a hydrophobicity scale on which glycine has the value 0.5. On such a scale, amino acids which have a preference for water have values below 0.5 and those that have a preference for nonpolar solvents have a value above 0.5. As used herein, the term hydrophobic amino acid refers to an amino acid that, on the hydrophobicity scale, has a value greater or equal to 0.5, in other words, has a tendency to partition in the nonpolar acid which is at least equal to that of glycine.

Examples of amino acids which can be employed include, but are not limited to: glycine, proline, alanine, cysteine, methionine, valine, leucine, tyosine, isoleucine, phenylalanine, tryptophan. Preferred hydrophobic amino acids include leucine, isoleucine, alanine, valine, phenylalanine and glycine. Combinations of hydrophobic amino acids can also be employed. Furthermore, combinations of hydrophobic and hydrophilic (preferentially partitioning in water) amino acids, where the overall combination is hydrophobic, can also be employed.

The amino acid can be present in the particles of the invention in an amount of at least 10 weight %. Preferably, the amino acid can be present in the particles in an amount ranging from about 20 to about 80 weight %. The salt of a hydrophobic amino acid can be present in the particles of the invention in an amount of at least 10 weight percent. Preferably, the amino acid salt is present in the particles in an amount ranging from about 20 to about 80 weight %. In preferred embodiments the particles have a tap density of less than about 0.4 g/cm.sup.3.

Methods of forming and delivering particles which include an amino acid are described in U.S. patent application Ser. No. 09/382,959, filed on Aug. 25, 1999, entitled Use of Simple Amino Acids to Form Porous Particles During Spray Drying, the teachings of which are incorporated herein by reference in their entirety.

Proteins/Amino Acids

Protein excipients may include albumins such as human serum albumin (HSA), recombinant human albumin (rHA), gelatin, casein, hemoglobin, and the like. Suitable amino acids (outside of the dileucyl-peptides of the invention), which may also function in a buffering capacity, include alanine, glycine, arginine, betaine, histidine, glutamic acid, aspartic acid, cysteine, lysine, leucine, isoleucine, valine, methionine, phenylalanine, aspartame, tyrosine, tryptophan, and the like. Preferred are amino acids and polypeptides that function as dispersing agents. Amino acids falling into this category include hydrophobic amino acids such as leucine, valine, isoleucine, tryptophan, alanine, methionine, phenylalanine, tyrosine, histidine, and proline. Dispersibility-enhancing peptide excipients include dimers, trimers, tetramers, and pentamers comprising one or more hydrophobic amino acid components such as those described above.

Carbohydrates

By non-limiting example, carbohydrate excipients may include monosaccharides such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol sorbitol (glucitol), pyranosyl sorbitol, myoinositol, isomalt, trehalose and the like.

Polymers

By non-limiting example, compositions may also include polymeric excipients/additives, e.g., polyvinylpyrrolidones, derivatized celluloses such as hydroxymethylcellulose, hydroxyethylcellulose, and hydroxypropylmethylcellulose, Ficolls (a polymeric sugar), hydroxyethylstarch, dextrates (e.g., cyclodextrins, such as 2-hydroxypropyl-.beta.-cyclodextrin and sulfobutylether-.beta.-cyclodextrin), polyethylene glycols, and pectin may also be used.

Highly dispersible particles administered comprise a bioactive agent and a biocompatible, and preferably biodegradable polymer, copolymer, or blend. The polymers may be tailored to optimize different characteristics of the particle including: i) interactions between the agent to be delivered and the polymer to provide stabilization of the agent and retention of activity upon delivery; ii) rate of polymer degradation and, thereby, rate of drug release profiles; iii) surface characteristics and targeting capabilities via chemical modification; and iv) particle porosity.

Surface eroding polymers such as polyanhydrides may be used to form the particles. For example, polyanhydrides such as poly[(p-carboxyphenoxy)hexane anhydride] (PCPH) may be used. Biodegradable polyanhydrides are described in U.S. Pat. No. 4,857,311. Bulk eroding polymers such as those based on polyesters including poly(hydroxy acids) also can be used. For example, polyglycolic acid (PGA), polylactic acid (PLA), or copolymers thereof may be used to form the particles. The polyester may also have a charged or functionalizable group, such as an amino acid. In a preferred embodiment, particles with controlled release properties can be formed of poly(D,L-lactic acid) and/or poly(DL-lactic-co-glycolic acid) ("PLGA") which incorporate a surfactant such as dipalmitoyl phosphatidylcholine (DPPC).

Other polymers include polyamides, polycarbonates, polyalkylenes such as polyethylene, polypropylene, poly(ethylene glycol), poly(ethylene oxide), poly(ethylene terephthalate), poly vinyl compounds such as polyvinyl alcohols, polyvinyl ethers, and polyvinyl esters, polymers of acrylic and methacrylic acids, celluloses and other polysaccharides, and peptides or proteins, or copolymers or blends thereof. Polymers may be selected with or modified to have the appropriate stability and degradation rates in vivo for different controlled drug delivery applications.

Highly dispersible particles can be formed from functionalized polyester graft copolymers, as described in Hrkach et al., Macromolecules, 28: 4736-4739 (1995); and Hrkach et al., "Poly(L-Lactic acid-co-amino acid) Graft Copolymers: A Class of Functional Biodegradable Biomaterials" in Hydrogels and Biodegradable Polymers for Bioapplications, ACS Symposium Series No. 627, Raphael M. Ottenbrite et al., Eds., American Chemical Society, Chapter 8, pp. 93-101, 1996.

In a preferred embodiment of the invention, highly dispersible particles including a bioactive agent and a phospholipid are administered. Examples of suitable phospholipids include, among others, phosphatidylcholines, phosphatidylethanolamines, phosphatidylglycerols, phosphatidylserines, phosphatidylinositols and combinations thereof. Specific examples of phospholipids include but are not limited to phosphatidylcholines dipalmitoyl phosphatidylcholine (DPPC), dipalmitoyl phosphatidylethanolamine (DPPE), distearoyl phosphatidyicholine (DSPC), dipalmitoyl phosphatidyl glycerol (DPPG) or any combination thereof. Other phospholipids are known to those skilled in the art.

The phospholipid, can be present in the particles in an amount ranging from about 0 to about 90 weight %. More commonly it can be present in the particles in an amount ranging from about 10 to about 60 weight %.

In another embodiment of the invention, the phospholipids or combinations thereof are selected to impart controlled release properties to the highly dispersible particles. The phase transition temperature of a specific phospholipid can be below, around or above the physiological body temperature of a patient. Preferred phase transition temperatures range from 30.degree. C. to 50.degree. C., (e.g., within .+-.0.10 degrees of the normal body temperature of patient). By selecting phospholipids or combinations of phospholipids according to their phase transition temperature, the particles can be tailored to have controlled release properties. For example, by administering particles which include a phospholipid or combination of phospholipids which have a phase transition temperature higher than the patient's body temperature, the release of dopamine precursor, agonist or any combination of precursors and/or agonists can be slowed down. On the other hand, rapid release can be obtained by including in the particles phospholipids having lower transition temperatures.

Flavor, Other

By non-limiting example, compositions may further include flavoring agents, taste-masking agents, inorganic salts (e.g., sodium chloride), antimicrobial agents (e.g., benzalkonium chloride), sweeteners, antioxidants, antistatic agents, surfactants (e.g., polysorbates such as "TWEEN 20" and "TWEEN 80"), sorbitan esters, lipids (e.g., phospholipids such as lecithin and other phosphatidylcholines, phosphatidylethanolamines), fatty acids and fatty esters, steroids (e.g., cholesterol), and chelating agents (e.g., EDTA, zinc and other such suitable cations). Other pharmaceutical excipients and/or additives suitable for use in the compositions according to the invention are listed in "Remington: The Science & Practice of Pharmacy", 19.sup.th ed., Williams & Williams, (1995), and in the "Physician's Desk Reference", 52.sup.nd ed., Medical Economics, Montvale, N.J. (1998).

EXAMPLES

The following examples serve to more fully describe the manner of using the above-described invention, as well as to set forth the best modes contemplated for carrying out various aspects of the invention. It is understood that these examples in no way serve to limit the true scope of this invention, but rather are presented for illustrative purposes. All references cited herein are incorporated by reference in their entirety.

Example 1

Potentiation of Levofloxacin by Pentamidine

Initial identification of pentamidine as an efflux pump inhibitor was performed by assessing its antibiotic potentiation activity.

Potentiation effect was observed by the reduction of the minimum inhibitory concentration of levofloxacin in the presence of pentamidine. The activity of pentamidine in combination with levofloxacin was assessed by the checkerboard assay (Antimicrobial Combinations. In Antibiotics in Laboratory Medicine, Ed. Victor Lorian, M.D., Fourth edition, 1996, pp 333-338, which is incorporated herein by reference in its entirety) using broth microdilution method performed as recommended by the NCCLS (National Committee for Clinical Laboratory Standards (NCCLS). 1997. Methods for Dilution of Antimicrobial Susceptibility Tests for Bacteria That Grow Aerobically—Fourth Edition; Approved Standard. NCCLS Document M7-A4, Vol 17 No. 2, which is incorporated herein by reference in its entirety). In this assay, multiple dilutions of two drugs, namely pentamidine and levofloxacin, were tested, alone and in combination, at concentrations equal to, above and below their respective minimal inhibitory concentrations (MICs). Pentamidine is readily soluble in water and stock solution was prepared at a final concentration of 10 mg/ml. Stock solutions were further diluted, according to the needs of a particular assay, in Mueller Hinton Broth (MHB). Stock solution was stored at −80° C.

The checkerboard assay was performed in microtiter plates. Levofloxacin was diluted in the x axis, each column containing a single concentration of levofloxacin. Pentamidine was diluted in the y axis, each row containing an equal concentration of pentamidine. The result of these manipulations is that each well of the microtiter plate contains a unique combination of concentrations of the two agents. The assay was performed in MHB with a final bacterial inoculum of $5 \times 10^5$ CFU/ml (from an early-log phase culture). Microtiter plates were incubated during 20 h at 35° C. and were read using a microtiterplate reader (Molecular Devices) at 650 nm as well as visual observation using a microtiter plate reading mirror. The MIC was defined as the lowest concentration of antibiotics, within the combination, at which the visible growth of the organism was completely inhibited.

Levofloxacin potentiation was studied in *Pseudomonas aeruginosa*. The test organisms used was PAM1020, which is a wild type strain of *P. aeruginosa* expressing the basal level of MexAB-OprM, as well as PAM1723, PAM1738, and PAM1753, overexpressing the MexAB-OprM, MexCD-OprJ, and MexEF-OprN pump, respectively. In addition levofloxacin potentiation by pentamidine was tested for the strain PAM1626, which lacks all the three efflux pumps mentioned above. Pentamidine was tested at the maximum concentration of 80 μg/ml. At this concentration, pentamidine demonstrated inhibition of growth of the wild type, however at 20 μg/ml it decreased the levofloxacin MIC in this strain 8-fold. Pentamidine MICs against PAM1723 and PAM1738 were higher than 80 μg/ml, however, at 20 μg/ml pentamidine decreased MICs in these strains 8- and 4-fold respectively. Almost no decrease in levofloxacin MIC was seen for PAM1626 lacking efflux pumps. These experiments demonstrated that pentamidine is capable of potentiating levofloxacin activity against strains of *P. aeruginosa* over-producing efflux pumps but not against the strain which lacks efflux pumps. This result strongly indicates that inhibition of efflux activity is a mechanism of levofloxacin potentiation (Table 1).

Importantly, the MIC of pentamidine against PAM1626 lacking efflux pumps was 10 μg/ml, which is lower than for the strains expressing efflux pumps. This indicates that pentamidine itself is a substrate of these pumps and therefore provides evidence of pentamidine directly interacting with pump proteins. One possible explanation for its pump inhibitory activity in the presence of other substrates such as levofloxacin, is its higher binding affinity to the substrate binding site.

TABLE 1

Potentiation of levofloxacin by pentamidine against the strains of *P. aeruginosa* expressing or lacking various efflux pumps.

| Strain | Relevant genotype | Pump which contributes to resistance | MIC* (μg/ml) | Levofloxacin MIC (μg/ml) in the presence of pentamidine (μg/ml) | | | | | | | |
|---|---|---|---|---|---|---|---|---|---|---|---|
| | | | | 0 | 1.25 | 2.5 | 5 | 10 | 20 | 40 | 80 |
| PAM1020 | wt | MexAB-OprM | 80 | 0.25 | 0.25 | 0.25 | 0.125 | 0.06 | 0.03 | 0.015 | NG |
| PAM1723 | nalB ΔmexCD-oprJ ΔmexEF-OprN | MexAB-OprM | >80 | 2 | 2 | 1 | 1 | 0.5 | 0.25 | 0.06 | 0.007 |
| PAM1738 | nfxB ΔmexCD-oprJ ΔmexAB-OprM | MexCD-OprJ | >80 | 0.5 | 0.5 | 0.25 | 0.25 | 0.25 | 0.125 | 0.03 | 0.015 |
| PAM1753 | nfxC ΔmexAB-oprM ΔmexCD-OprJ | MexEF-OprN | 40 | 4 | 2 | 2 | 2 | 1 | 0.25 | NG | NG |

TABLE 1-continued

Potentiation of levofloxacin by pentamidine against the strains of *P. aeruginosa* expressing or lacking various efflux pumps.

| Strain | Relevant genotype | Pump which contributes to resistance | MIC* (μg/ml) | Levofloxacin MIC (μg/ml) in the presence of pentamidine (μg/ml) | | | | | | | |
|---|---|---|---|---|---|---|---|---|---|---|---|
| | | | | 0 | 1.25 | 2.5 | 5 | 10 | 20 | 40 | 80 |
| PAM1626 | ΔmexAB-OprM ΔmexCD-oprJ ΔmexEF-OprN | none | 10 | 0.015 | 0.007 | 0.007 | 0.007 | NG | NG | NG | NG |

*MIC for the efflux pump inhinbitor (pentamidine)

Example 2

Potentiation of Efflux Pump Substrates by Pentamidine

While not being bound by any particular theory, it is proposed that pentamidine potentiates antibiotics which are substrates for efflux pumps inhibited by pentamidine. To test this, MICs to several antibiotics for the strain PAM1723 of *P. aeruginosa* were measured with or without a fixed concentration of pentamidine (40 μg/ml). Pentamidine decreased the MICs of several substrates of MexAB-OprM including levofloxacin (16-fold), ciprofloxacin (8-fold), azithromycin (64-fold), erythromycin (4-fold), and chloramphenicol (16-fold) (Table 2). In contrast, almost no effect of pentamidine was seen for tobramycin, which is not a substrate of this pump (see PAM1723 vs. PAM1154 in Table 2).

TABLE 2

Impact of pentamidine on susceptibility to multiple antibiotics.

| | Impact of EPIs on susceptibility of PAM1723 (MexAB-OprM overexpressed) to various antibiotics | | PAM1154 (MexAB-OprM deleted) |
|---|---|---|---|
| Antibiotic | No Pentamidine | Pentamidine (40 μg/ml) | No Pentamidine |
| Levo | 1 | 0.06 | 0.015 |
| Cipro | 0.25 | 0.03 | 0.008 |
| Azithro | 64 | 1 | 0.5 |
| Erm | 256 | 64 | 8 |
| Cm | 128 | 8 | 1 |
| Tb | 0.06 | 0.03 | 0.03 |

Example 3

Accumulation Assays

Further proof of efflux pump inhibitory activity of pentamidine was obtained in accumulation assays. Leucine-β-naphthylamide (Leu-Nap) is a substrate of the Mex pumps from *P. aeruginosa*. Leu-Nap, which is not fluorescent in solution, is cleaved enzymatically inside the cells to produce highly fluorescent β-naphthylamine. The more Leu-Nap enters cells, the more fluorescence is produced. The rate of production of β-naphthylamine (recorded as an increase in fluorescence) is limited by the rate of entry of Leu-Nap into the cell. To assess the uptake of Leu-Nap, cultures of *P. aeruginosa* were grown to $OD_{600}$ ~1, washed and re-suspended in buffer at pH 7.0 containing $K_2HPO_4$ 50 mM, $MgSO_4$ 1 mM, and Glucose 0.4% (Buffer A). Assays were performed in 96-well flat bottom black plates (Applied Scientific or Costar) in a final volume of 200 μl and were initiated by addition of Leu-Nap to suspensions of intact cells to a final concentration of 100-20 μg/ml. Fluorescence was measured on a fMAX spectrofluorometer (Molecular Devices) using excitation of 320 nm and emission of 460 nm. To measure effects of pentamidine on the rate of Leu-Nap uptake, cells were pre-incubated with different concentrations of pentamidine compounds prior to Leu-Nap addition.

Figure 1B:
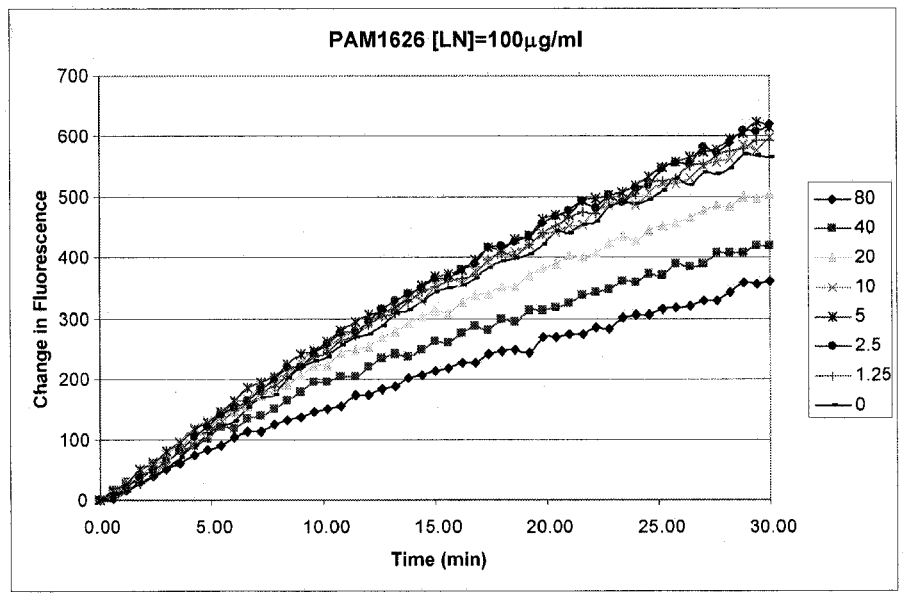
FIG. 1B illustrates the effect in PAM 1626 cells.

The uptake of Leu-Nap (100 μg/ml) by PAM1723 (FIG. 1A) or PAM1626 (FIG. 1B) cells was studied in the presence of various concentrations (0 μg/ml to 80 μg/ml) of pentamidine. When no pentamidine is added, the rate of cleavage of Leu-Nap was much higher in PAM1626 (FIG. 1B) than in PAM1723 (FIG. 1A—over expressing efflux pump) indicating the Leu-Nap is indeed a substrate of the pump. Addition of pentamidine to PAM1723 cells increases Leu-Nap uptake in the dose-dependent manner (FIG. 1A).

No such increase was seen in the case of PAM1626 cells (lacking the efflux pump). In fact, addition of pentamidine caused a decrease of fluorescence in this latter strain, most probably due to quenching of naphthylamine fluorescence by pentamidine. At a pentamidine concentration of 40 μg/ml (squares in FIGS. 1A and 1B) the rate of uptake in both strains was very similar, indicating that at this concentration pentamidine completely inhibits efflux of Leu-Nap from PAM1723.

Example 4

Mechanism of Efflux Pump Inhibition

Figure 2A:
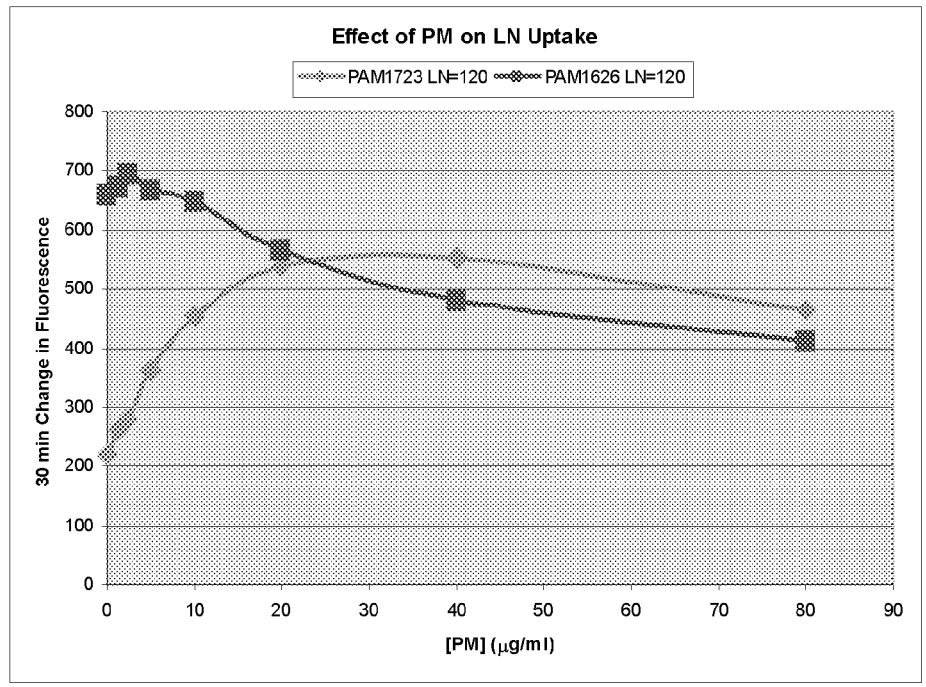
FIGS. 2A and 2B illustrate the effect of Leu-Nap concentration (120 μg/ml in FIG. 2B; 60 μg/ml in FIG. 2A) of the pentamidine inhibitory activity.
Figure 2B:
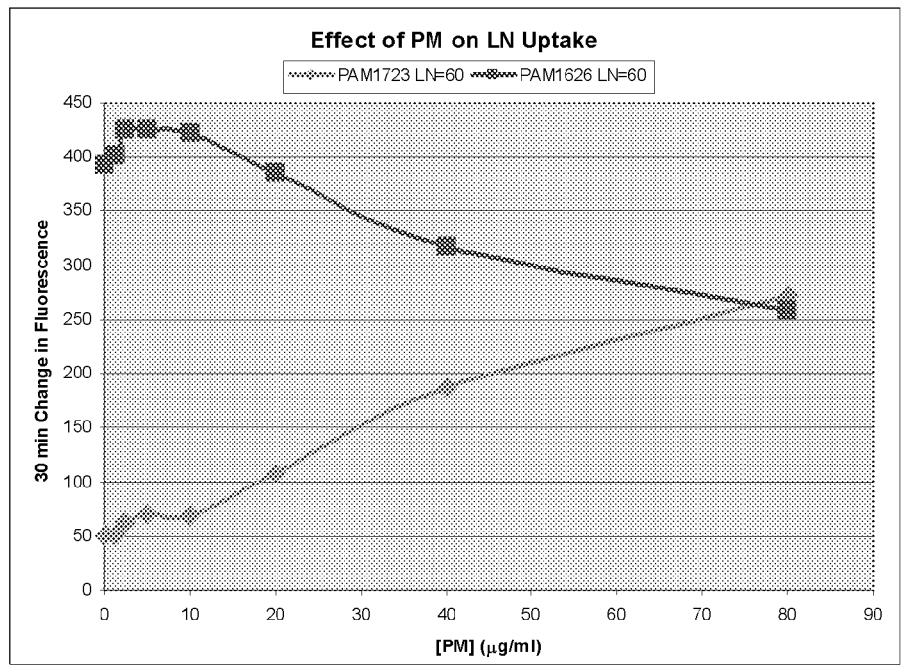

The effect of Leu-Nap substrate concentration on inhibition was investigated. For both PAM1626 and PAM1723 strains, change in Leu-Nap fluorescence in 30 min. was plotted as a function of pentamidine concentration for external Leu-Nap concentrations of 120 μg/ml (FIG. 2A) and 60 μg/ml (FIG. 2B). When external concentration of Leu-Nap was 120 μg/ml, 20 μg/ml of pentamidine was required to completely inhibit MexAB-OprM-mediated efflux (i.e., the same fluorescence is produced in PAM1723 and PAM1626). When the Leu-Nap concentration was decreased to 60 μg/ml, 80 μg/ml of pentamidine was required for complete inhibition of the pump. This result implies that the degree of inhibition is inversely dependent on the substrate concentration, indicating uncompetitive inhibition. The effect of the substrate on the degree of inhibition is a strong indication of the efflux pump inhibitory mode of action of pentamidine.

Example 5

Membrane Permeabilization

Both antibiotic potentiation and increased uptake in the presence of pentamidine might be a result of the permeabilization of the outer membrane of *P. aeruginosa* by this compound. To rule out this possibility a direct outer membrane permeabilization experiment was performed. In this assay the rates of hydrolysis of a chromogenic β-lactam, nitrocefin, by intact cells of *P. aeruginosa* expressing β-lactamase, was examined. β-lactamase is located in the periplasm. An increased rate of hydrolysis in intact cells is indicative of increased permeation of nitrocefin across the outer membrane since the rate of hydrolysis is limited by the rate of this permeation. The potential outer membrane permeabilizing effect of pentamidine was examined using *P. aeruginosa* strain PAM2005. This strain constitutively produces β-lactamase AmpC, encoded by the corresponding gene normally present in the genome of this bacterium. PAM2005 also overproduces the MexAB-OprM efflux pump. PMBN, the known outer membrane permeabilizing agent was used for these experiments. Cells were grown overnight in L-broth, harvested, washed in $Mg^{2+}$ free accumulation buffer, and re-suspended in the same buffer at $OD_{600}$ of 0.5. To 100 μl of cell suspension, 50 μl of either PMBN or pentamidine was added to give a final concentration ranging from 2 to 64 μg/ml. Next, 50 μl of nitrocefin was added to give a final concentration of 64 μg/ml. Hydrolysis of nitrocefin was monitored spectrophotometrically by measurement of the increase in absorbance at 574 nm. Assays were performed in 96-well plates in a SpectraMAX Plus spectrophotometer (Molecular Devices).

Figure 3A:
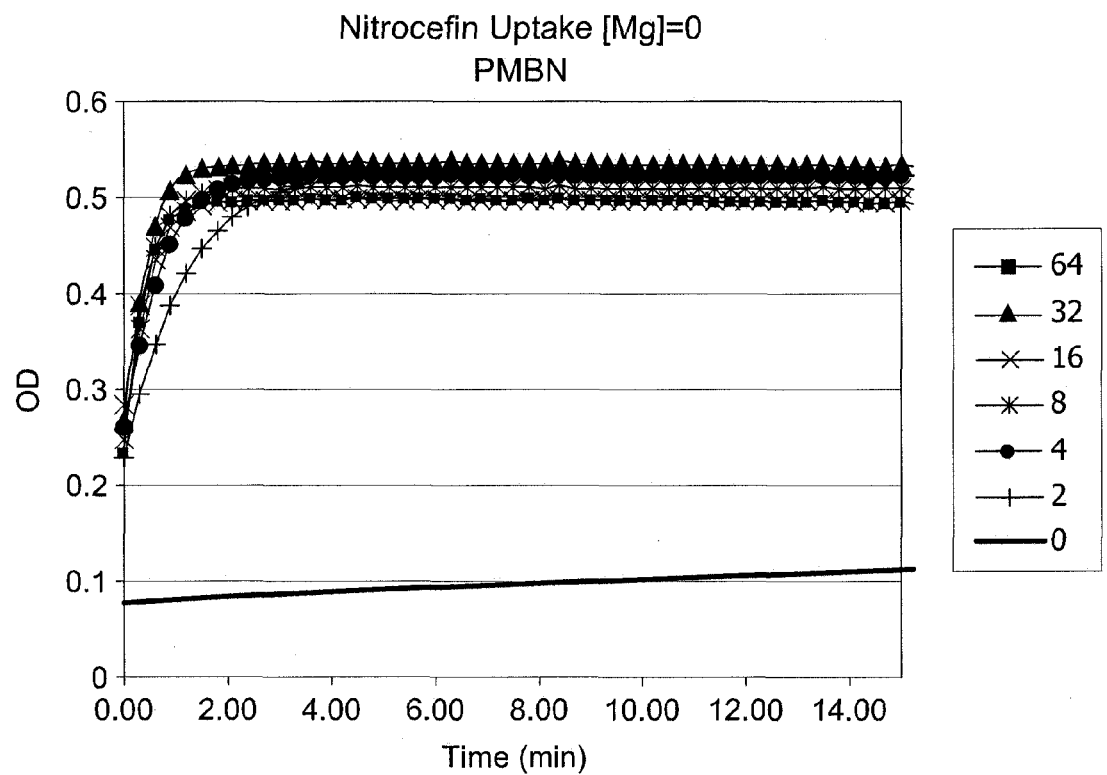
FIGS. 3A and 3B depict the results of the investigation of the outer membrane permeabilizing activity of PMBN (FIG. 3A) and pentamidine (FIG. 3B).
Figure 3B:
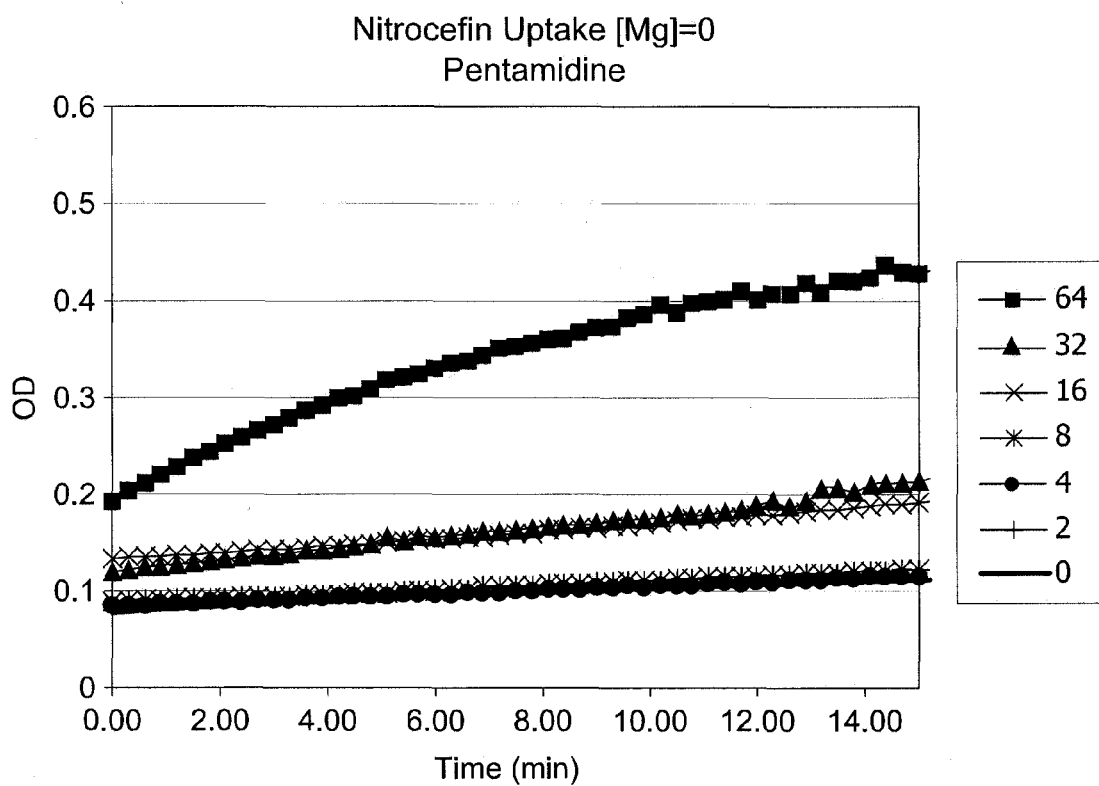
Figure 4:
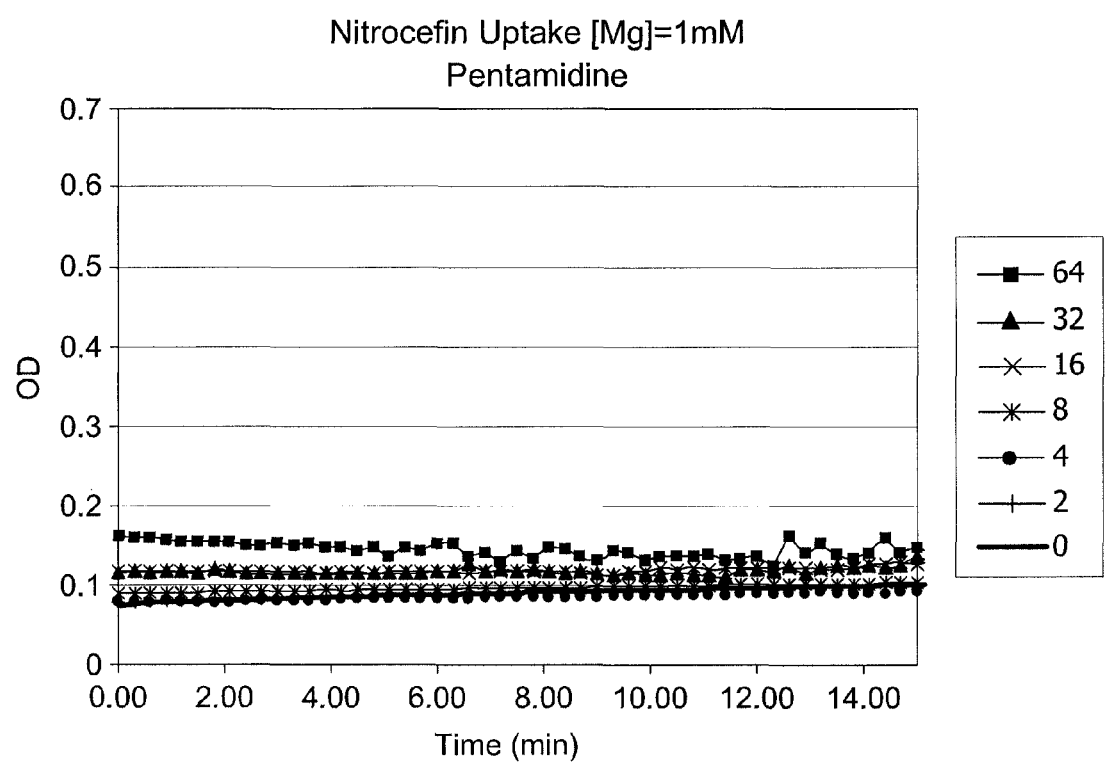
FIG. 4 depicts the results of the investigation of the outer membrane permeabilizing activity of pentamidine in the presence of $Mg^{2+}$.

PMBN had a dramatic effect on the permeabilization of the outer membrane with $IC_{50}$<2 μg/ml (FIG. 3A). In contrast pentamidine had rather weak membrane permeabilization activity with $IC_{50}$ exceeding 64 μg/ml (FIG. 4). Even this weak activity is completely abrogated when 1 mM $Mg^{2+}$ is added to the reaction buffer (FIG. 4). At this concentration of $Mg^{2+}$, pentamidine has an effect in Leu-Nap accumulation experiments. Thus, it is proposed that pentamidine acts on efflux pumps rather than promoting membrane permeabilization.

Example 6

Proton Gradient Disruption

Figure 5A:
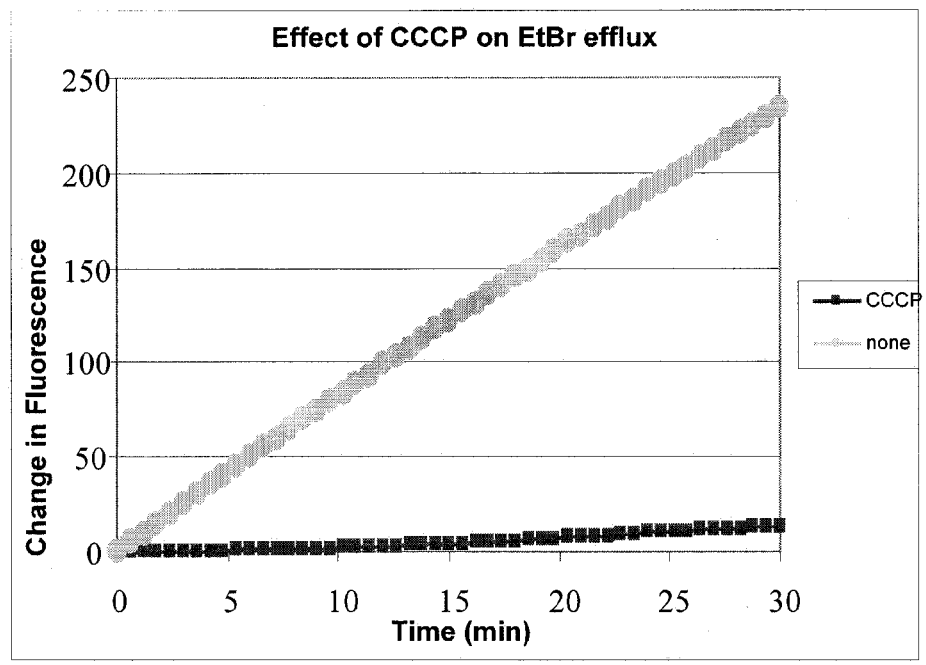
FIGS. 5A and 5B show the effect of CCCP (FIG. 5A) and pentamidine (FIG. 5B) on efflux of EtBr in *P. aeruginosa*.
Figure 5B:
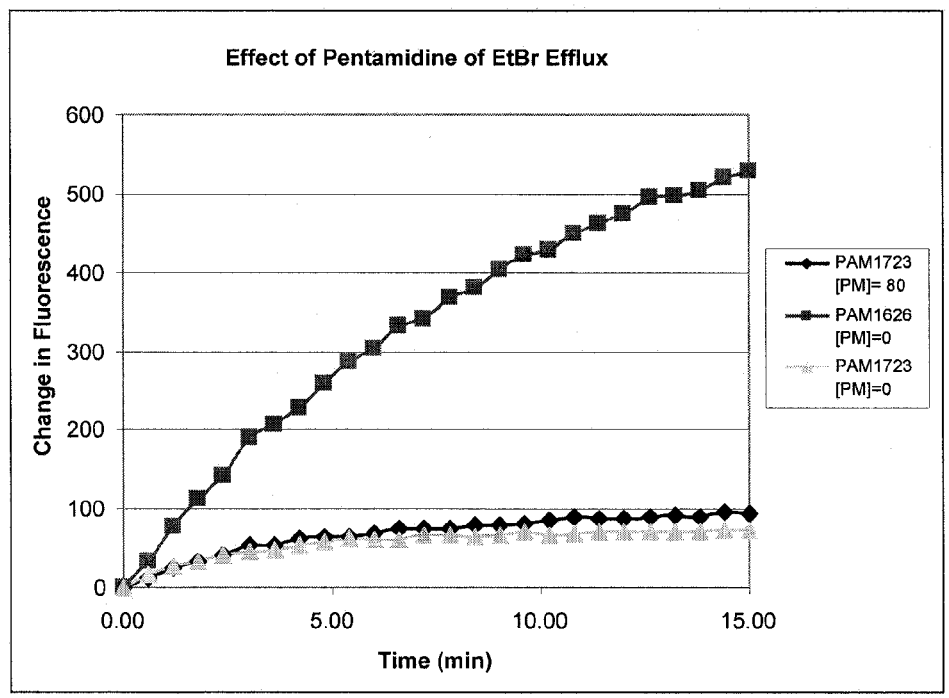

A proton gradient is necessary for efflux pump activity. Accordingly, compounds that are capable of proton gradient disruption will appear as efflux inhibitors in accumulation assays. This possibility was tested for pentamidine. EtBr is a substrate of the MexAB-OprM efflux pump from *P. aeruginosa* as evident from the differential rates of its uptake in PAM1723 and PAM1626, MexAB-OprM overexpressing or lacking strains, respectively. CCCP is a well-known protonophore, which rapidly dissipates the proton gradient. Treatment of PAM1723 cells with 50 μg/ml of CCCP for 15 minutes resulted in dramatic increase of EtBr uptake (FIG. 5A). In contrast, treatment of cells with pentamidine at 80 μg/ml did not result in increased EtBr uptake (FIG. 5B) indicating that pentamidine unlike CCCP does not disrupt the proton gradient. The pump inhibitory activity of pentamidine is not based on disruption of the proton gradient across the inner membrane of *P. aeruginosa*.

Example 7

Effect of Pentamidine on Multiple Over-expressing Efflux Pumps

The impact of fixed concentrations of pentamidine on the susceptibility of fluoroquinolones to various *P. aeruginosa* strains was determined. Multiple concentrations of antibiotics were tested in the presence of a single chosen concentration of pentamidine. As above, the MIC was defined as the lowest concentration of antibiotic, within the combination, at which the visible growth of the organism was completely inhibited.

A set of strains that simultaneously over-expressed pairs or triplicates of pumps, e.g. PAM2302 and PAM2303 was tested. Simultaneous over-expression of efflux pumps has been recently detected in clinical strains. The data indicate that pentamidine increased susceptibility in strains over-expressing multiple pumps. Moreover, in the presence of pentamidine, susceptibility to both fluoroquinolones was similar.

TABLE 3

Impact of pentamidine on Susceptibility to fluoroquinolones of *P. aeruginosa* Strains Simultaneously Over-expressing Multiple Efflux Pumps.

| | | Levofloxacin MIC (μg/ml) | | Ciprofloxacin MIC (μg/ml) | |
| --- | --- | --- | --- | --- | --- |
| Strain | Pump status | w/o pentamidine | w/pentamidine at 20 μg/ml | w/o pentamidine | w/pentamidine at 20 μg/ml |
| PAM1020 | none | 0.25 | 0.03 | 0.06 | 0.015 |
| PAM1032 | MexAB-OprM | 2 | 0.125 | 0.5 | 0.06 |
| PAM1033 | MexCD-OprJ | 4 | 0.25 | 1 | 0.25 |
| PAM1034 | MexEF-OprN | 4 | 0.125 | 1 | 0.06 |
| PAM1438 | MexAB-OprM MexCD-OprJ | 4 | 0.25 | 16 | 0.25 |
| PAM2281 | MexAB-OprM MexEF-OprN | 8 | 0.25 | 8 | 0.25 |
| PAM2282 | MexAB-OprM MexEF-OprN | 8 | 0.25 | 2 | 0.125 |
| PAM2302 | MexAB-OprM MexCD-OprJ MexEF-OprN | 8 | 0.25 | 2 | 0.25 |
| PAM2466 | MexAB-OprM MexXY-OprM | 2 | 0.125 | 0.5 | 0.06 |

Example 8

Effect of Pentamidine on Target Mutation Antibiotic Resistance

In addition to increased efflux, resistance to fluoroquinolones may be due to target mutations (gyrase and topoisimerase IV) or due to combination of these two resistance mechanisms in a single bacterial cell. Consequently, the effect of fixed concentrations of pentamidine on strains of *P. aeruginosa* containing various combinations of efflux-mediated and target-based mutations was measured. All tested fluoroquinolones were affected by target-based mutations. Moreover, the degree of this impact was similar for all the tested fluoroquinolones in that each mutation demonstrated a 4 to 8-fold effect. As expected, both mechanisms contribute to fluoroquinolone resistance independently. The same contribution of target-based mutations was observed regardless of which pump was over-expressed, and conversely the same contribution of efflux was observed regardless of which target-based mutation was present. Pentamidine increased susceptibility to fluoroquinolones in strains with efflux-based and target-mediated mutations (Table 4).

Figure 6:
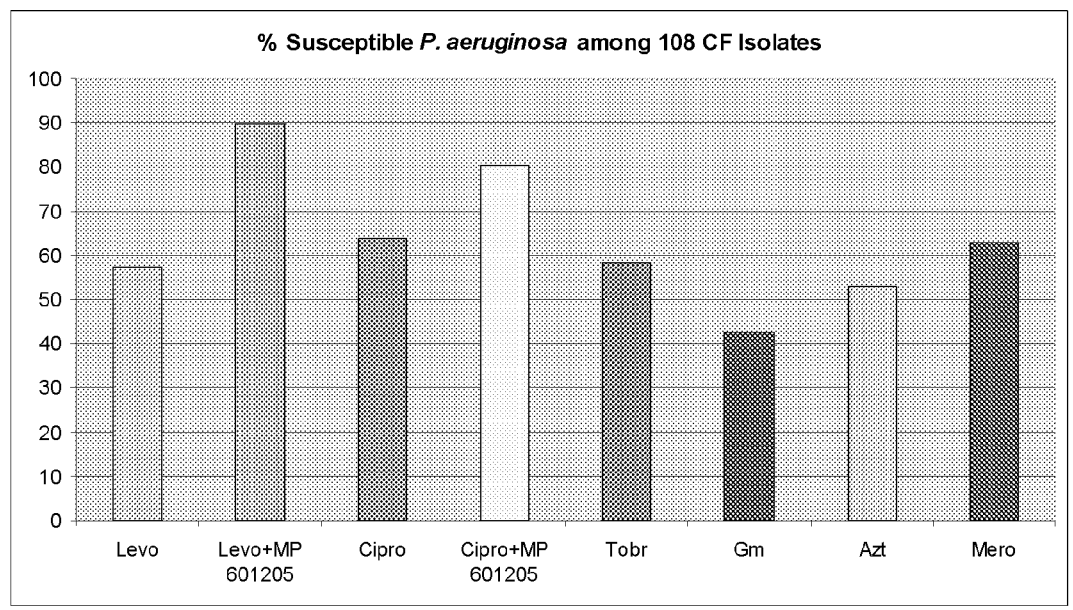
FIG. 6 shows the susceptibility of the cystic fibrosis isolates *P. aeruginosa* to various antibiotics and fluoroquinolone/pentamidine combinations.

These later antibiotics are used to treat *P. aeruginosa* infections during exacerbation of the disease. Susceptibility of clinical isolates of *P. aeruginosa* to antibiotics was determined using broth two-fold broth-micro-dilution method in according to the National Committee for Clinical Laboratory Standards (NCCLS) recommendations. Ciprofloxacin, levofloxacin, and aztreonam were tested at concentrations raging from 64 µg/ml to 0.06 µg/ml. Tobramycin and gentamicin were tested at concentrations raging from 128 µg/ml to 1.25 µg/ml. Additionally, the isolates were tested against ciprofloxacin and levofloxacin in the presence of 20 µg/ml of pentamidine (the same range of fluoroquinolones of 64 µg/ml to 0.06 µg/ml was used). The strains were determined to be Resistant (R), Intermediate (I) or Susceptible (S) according to NCCLS susceptibility breakpoints. Finally, the percent of susceptible organisms was calculated for each antibiotic (FIG. 6). In the case of fluoroquinolone/pentamidine combinations, susceptibility breakpoints were based on the corresponding antibiotics.

TABLE 4

Impact of Pentamidine on Susceptibility of *P. aeruginosa* Strains with Combinations of Efflux and Target Mutations.

| | | | Levofloxacin MIC (µg/ml) | | Ciprofloxacin MIC (µg/ml) | |
| --- | --- | --- | --- | --- | --- | --- |
| Strain | Pump status | Target mutation | w/o pentamidine | w/pentamidine at 20 µg/ml | w/o pentamidine | w/pentamidine at 20 µg/ml |
| PAM1020 | none | none | 0.25 | 0.03 | 0.06 | 0.015 |
| PAM1032 | MexAB-OprM | none | 2 | 0.125 | 0.5 | 0.06 |
| PAM1033 | MexCD-OprJ | none | 4 | 0.25 | 1 | 0.25 |
| PAM1034 | MexEF-OprN | none | 4 | 0.125 | 1 | 0.06 |
| PAM1481 | MexAB-OprM | gyrA (Asp87Tyr) | 16 | 1 | 4 | 0.5 |
| PAM1482 | MexCD-OprJ | gyrA (Asp87Tyr) | 16 | 1 | 8 | 2 |
| PAM1483 | MexAB-OprM MexCD-OprJ | gyrA (Asp87Tyr) | 16 | 1 | 8 | 2 |
| PAM1491 | MexEF-OprN | gyrA (Asp87Tyr) | 32 | 2 | 8 | 1 |
| PAM1548 | none | gyrA (Thr83Ile) | 2 | 0.25 | 2 | 0.5 |
| PAM1569 | MexCD-OprJ | gyrA (Thr83Ile) | 32 | 4 | 16 | 4 |
| PAM1570 | MexEF-OprN | gyrA (Thr83Ile) | 32 | 2 | 16 | 2 |
| PAM1573 | MexAB-OprM | gyrA (Thr83Ile) | 16 | 1 | 8 | 1 |
| PAM1582 | MexAB-OprM | gyrA (Thr83Ile) parC (Ser87Leu) | 64 | 4 | 64 | 8 |
| PAM1609 | MexAB-OprM | gyrA (Thr83Ile) parC (Ser87Leu) gyrA (Asp87Tyr) | >128 | 16 | >64 | 16 |
| PAM1667 | none | gyrA (Thr83Ile) parC (Ser87Leu) | 8 | 1 | 32 | 4 |
| PAM1669 | none | gyrA (Thr83Ile) parC (Ser87Leu) gyrA (Asp87Tyr) | 32 | 4 | 64 | 8 |

Example 9

Effect of Pentamidine on *P. aeruginosa* Isolated from Patients with Cystic Fibrosis Susceptibility to levofloxacin and ciprofloxacin of 108 recent clinical isolates of *P. aeruginosa* obtained from cystic fibrosis patients was determined in the presence of fixed concentrations of 20 µg/ml pentamidine. In addition, susceptibilities of the same strains to aminoglycosides tobramycin and gentamicin and beta-lactam aztreonam was determined.

Figure 7:
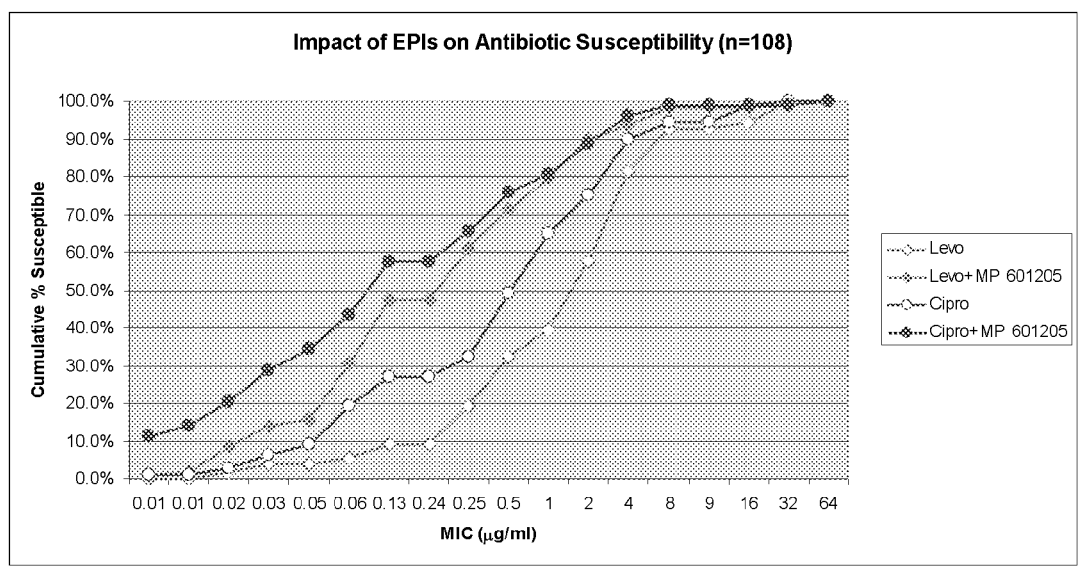
FIG. 7 depicts the impact of pentamidine on fluoroquinolone susceptibility of strains of *P. aeruginosa* isolated from patients with Cystic Fibrosis.

The results indicated that among all antibiotics tested, fluoroquinolone/pentamidine combinations possessed the most potent anti-pseudomonal activity. This result can be also presented as a distribution of MICs with or without potentiators (FIG. 7). Such presentation allows determination of $MIC_{50}$ and $MIC_{9-50}$ of the population (i.e., MIC of 50% and 90% of the strains respectively). In the case of this particular panel of strains, pentamidine decreased $MIC_{50}$ and $MIC_{90}$ of levofloxacin and ciprofloxacin 8-fold and 2-fold, respectively (Table 5).

TABLE 5

MICs for antibiotics tested.

|  | Levo | Levo/pentamidine | Cipro | Cipro/pentamidine |
|---|---|---|---|---|
| $MIC_{50}$ | 2 | 0.25 | 1 | 0.125 |
| $MIC_{90}$ | 8 | 4 | 8 | 4 |

Figure 8:
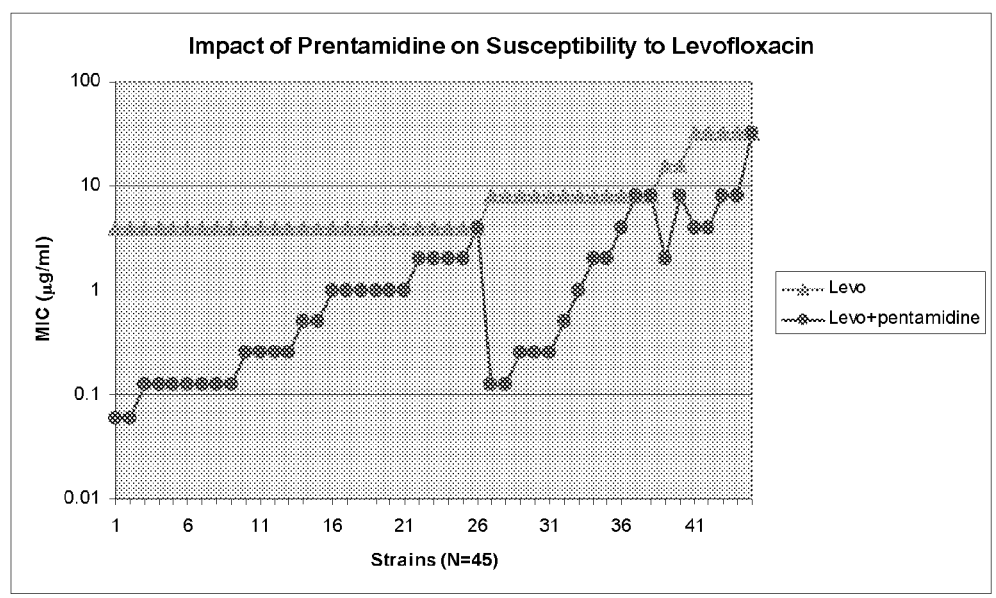
FIG. 8 depicts the impact of pentamidine on levofloxacin susceptibility of strains of *P. aeruginosa* isolated from patients with Cystic Fibrosis.

Examples of potentiation of the antibiotic effect by pentamidine against the individual strains are shown in the graph in FIG. 8. The 45 strains shown on this Figure were selected based on their resistance to levofloxacin (MIC>2 µg/ml). Pentamidine decreased levofloxacin MICs of the most of resistant stains 4-fold to 64-fold.

Example 10

Effect of Pentamidine on Bacterial Death

Figure 9A:
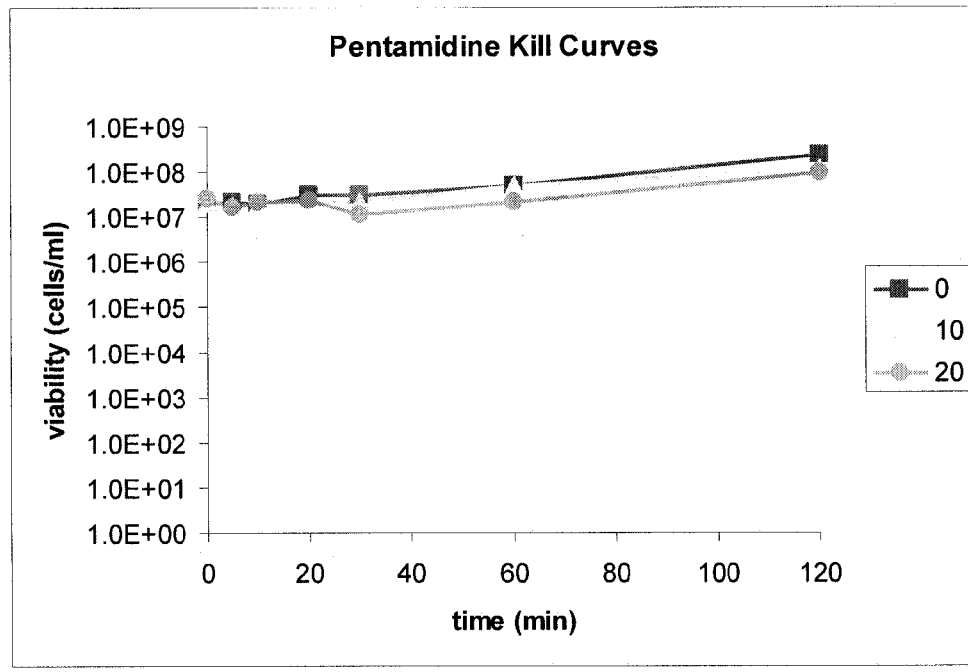
FIG. 9A depicts the impact of pentamidine alone on bacterial killing
Figure 9B:
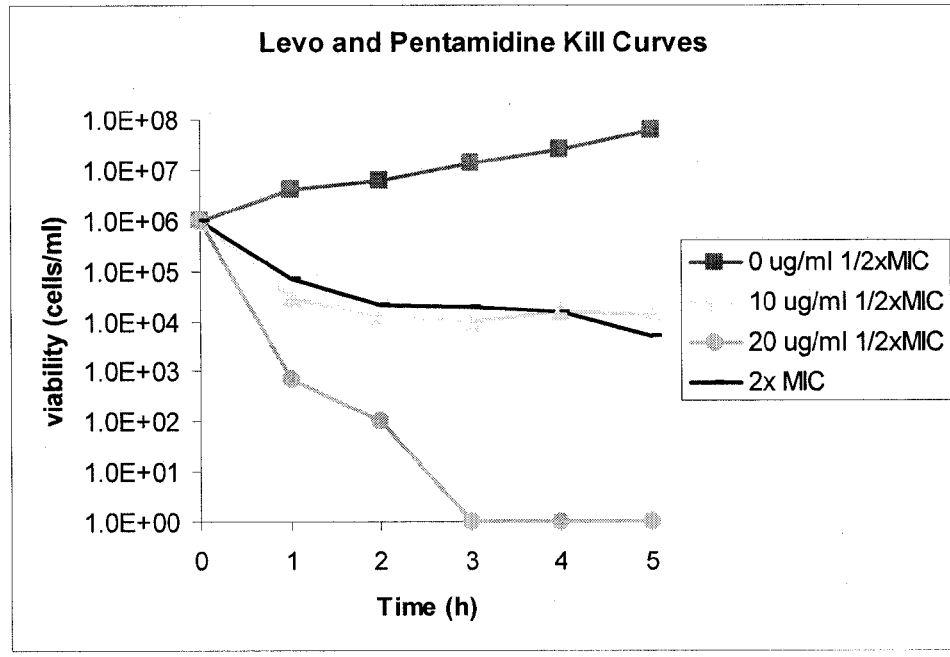
FIG. 9B depicts the impact of pentamidine on bacterial killing by Levofloxacin.

Another way to establish potentiating activity of EPIs is to demonstrate their effect on killing by fluoroquinolones. The strain PAM1032 overexpressing the MexAB-OprM efflux pump was grown in the presence of sub-inhibitory concentration of levofloxacin (½ of MIC or 1 g/ml) either with no addition or in the presence of 10 µg/ml or 20 µg/ml of pentamidine. The effect of pentamidine on killing was compared to the effect of 4 µg/ml of levofloxacin (2×MIC). While pentamidine alone did not have any effect on killing of *P. aeruginosa* (FIG. 9A), it significantly inhanced levofloxacin killing (FIG. 9B). In fact, 10 µg/ml of pentamidin in the presence of ½×MIC of levofloxacin had similar effect on killing of *P. aeruginosa* as 2×MIC and 20 had even stronger effect.

Example 11

Efflux Pump Inhibitory Activity of Pentamidine Analogs

Efflux pump inhibitory activity of three pentamidine analogs were evaluated using the levofloxacin potentiation checkerboard assay against five strains of *P. aeruginosa* overexpressing or lacking efflux pumps (as in Example 1). All three compounds, propamidine, dibromopropamidine, and hexamidine potentiated levofloxacin against the strains overexpressing various efflux pumps. The levofloxacin potentiating activity of these compounds was comparable to pentamidine. For example, all three compounds and pentamidine reduced the levofloxacin MIC of the strain PAM1723 (2 µg/ml) overexpressing the MexAB-OprM efflux pump at least 8-fold at concentrations of 10 µg/ml to 20 µg/ml (Table 5). Importantly, the MICs of all tested pentamidine analogs against PAM1626 lacking efflux pumps were lower than for the strains expressing efflux pumps. This indicates that similar to pentamidine, pentamidine analogs are substrates of these pumps.

TABLE 5

Potentiation of levofloxacin by several pentamidine analogs against the strains of *P. aeruginosa* expressing or lacking various efflux pumps.

A. Propamidine

| Strain | Relevant genotype | Pump which contributes to resistance | MIC* (µg/ml) | Levofloxacin MIC (µg/ml) in the presence of propamidine [MP 001039] (ug/ml) | | | | | | |
|---|---|---|---|---|---|---|---|---|---|---|
| | | | | 0 | 1.25 | 2.5 | 5 | 10 | 20 | 40 | 80 |
| PAM1020 | wt | MexAB-OprM | 40 | 0.25 | 0.25 | 0.125 | 0.125 | 0.06 | 0.03 | NG | NG |
| PAM1723 | nalB ΔmexCD-oprJ ΔmexEF-OprN | MexAB-OprM | 40 | 2 | 2 | 2 | 1 | 0.5 | 0.25 | NG | NG |
| PAM1738 | nfxB ΔmexCD-oprJ ΔmexAB-OprM | MexCD-OprJ | 40 | 0.5 | 0.5 | 0.5 | 0.25 | 0.125 | 0.015 | NG | NG |
| PAM1753 | nfxC ΔmexAB-oprM ΔmexCD-OprJ | MexEF-OprN | 5 | 4 | 4 | 2 | NG | NG | NG | NG | NG |
| PAM1626 | ΔmexAB-OprM ΔmexCD-oprJ ΔmexEF-OprN | none | 10 | 0.015 | 0.015 | 0.007 | 0.007 | NG | NG | NG | NG |

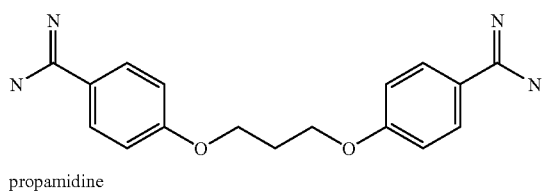

propamidine

TABLE 5-continued

Potentiation of levofloxacin by several pentamidine analogs against the strains of *P. aeruginosa* expressing or lacking various efflux pumps.

B. Dibromopropamidine

| Strain | Relevant genotype | Pump which contributes to resistance | MIC* (µg/ml) | Levofloxacin MIC (µg/ml) in the presence of dibromopropamidine [MP 001040] (ug/ml) | | | | | | | |
|---|---|---|---|---|---|---|---|---|---|---|---|
| | | | | 0 | 1.25 | 2.5 | 5 | 10 | 20 | 40 | 80 |
| PAM1020 | wt | MexAB-OprM | 80 | 0.25 | 0.25 | 0.25 | 0.125 | 0.06 | 0.03 | 0.03 | NG |
| PAM1723 | nalB ΔmexCD-oprJ ΔmexEF-OprN | MexAB-OprM | 80 | 2 | 2 | 1 | 0.5 | 0.125 | 0.06 | 0.06 | NG |
| PAM1738 | nfxB ΔmexCD-oprJ ΔmexAB-OprM | MexCD-OprJ | 80 | 0.5 | 0.5 | 0.25 | 0.125 | 0.06 | 0.03 | 0.03 | NG |
| PAM1753 | nfxC ΔmexAB-oprM ΔmexCD-OprJ | MexEF-OprN | 20 | 4 | 2 | 1 | 0.5 | 0.125 | NG | NG | NG |
| PAM1626 | ΔmexAB-OprM ΔmexCD-oprJ ΔmexEF-OprN | none | 5 | 0.015 | 0.0075 | 0.007 | NG | NG | NG | NG | NG |

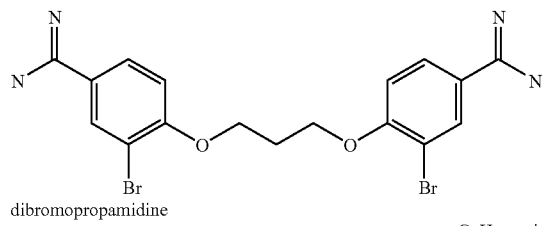
dibromopropamidine

C. Hexamidine

| Strain | Relevant genotype | Pump which contributes to resistance | MIC* (µg/ml) | Levofloxacin MIC (µg/ml) in the presence of hexamidine [MP 001041] (ug/ml) | | | | | | | |
|---|---|---|---|---|---|---|---|---|---|---|---|
| | | | | 0 | 1.25 | 2.5 | 5 | 10 | 20 | 40 | 80 |
| PAM1020 | wt | MexAB-OprM | 20 | 0.25 | 0.125 | 0.125 | 0.03 | 0.007 | NG | NG | NG |
| PAM1723 | nalB ΔmexCD-oprJ ΔmexEF-OprN | MexAB-OprM | 40 | 2 | 2 | 1 | 1 | 0.125 | 0.015 | NG | NG |
| PAM1738 | nfxB ΔmexCD-oprJ ΔmexAB-OprM | MexCD-OprJ | 80 | 0.5 | 0.5 | 0.5 | 0.25 | 0.06 | 0.015 | 0.007 | NG |
| PAM1753 | nfxC ΔmexAB-oprM ΔmexCD-OprJ | MexEF-OprN | 20 | 4 | 2 | 2 | 1 | 0.25 | NG | NG | NG |
| PAM1626 | ΔmexAB-OprM ΔmexCD-oprJ ΔmexEF-OprN | none | 2.5 | 0.015 | 0.007 | NG | NG | NG | NG | NG | NG |

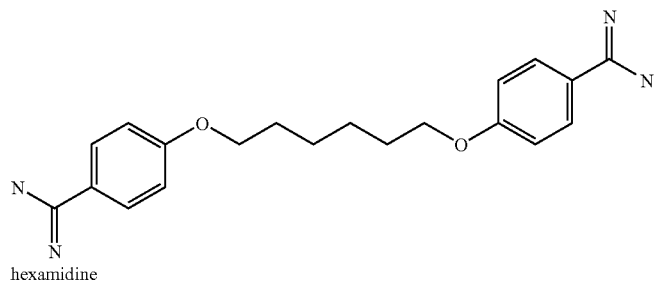
hexamidine

Example 12

Accumulation Assays of Pentamidine Analogs

Figure 10A:
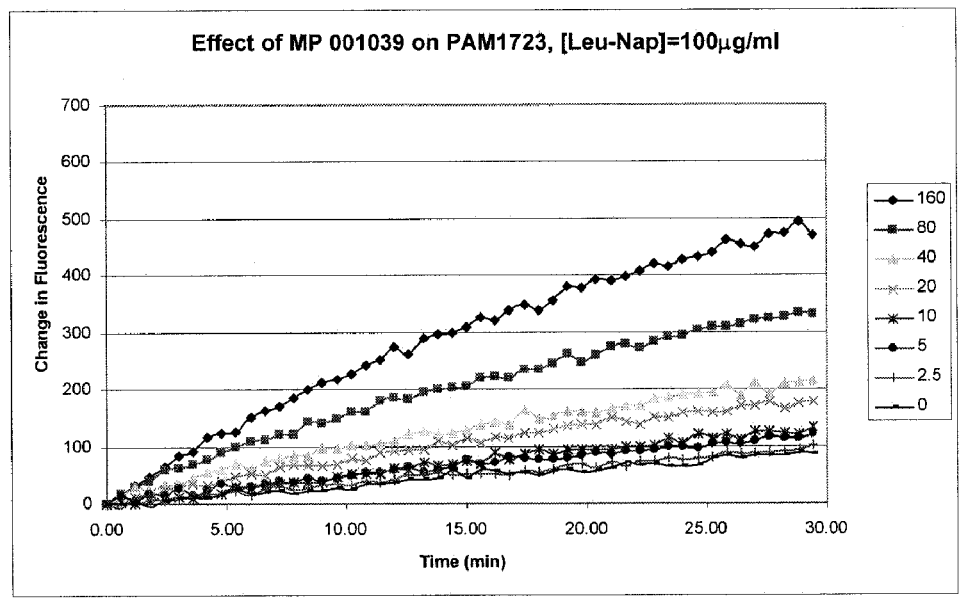
FIG. 10A depicts inhibition Leu-Nap efflux from PAM1723 by Propamidine.
Figure 10B:
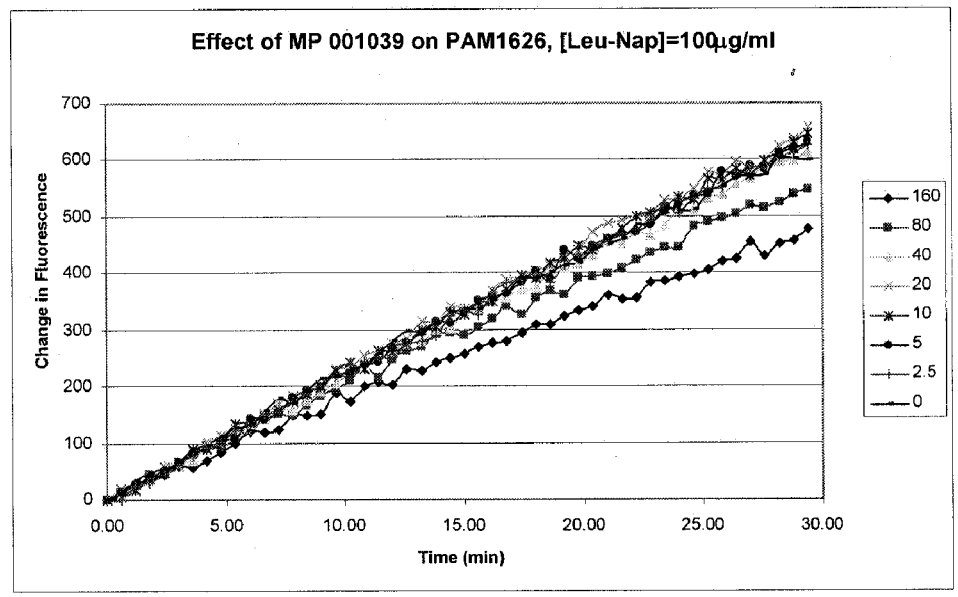
FIG. 10B depicts inhibition Leu-Nap efflux from PAM1626 by Propamidine.
Figure 10C:
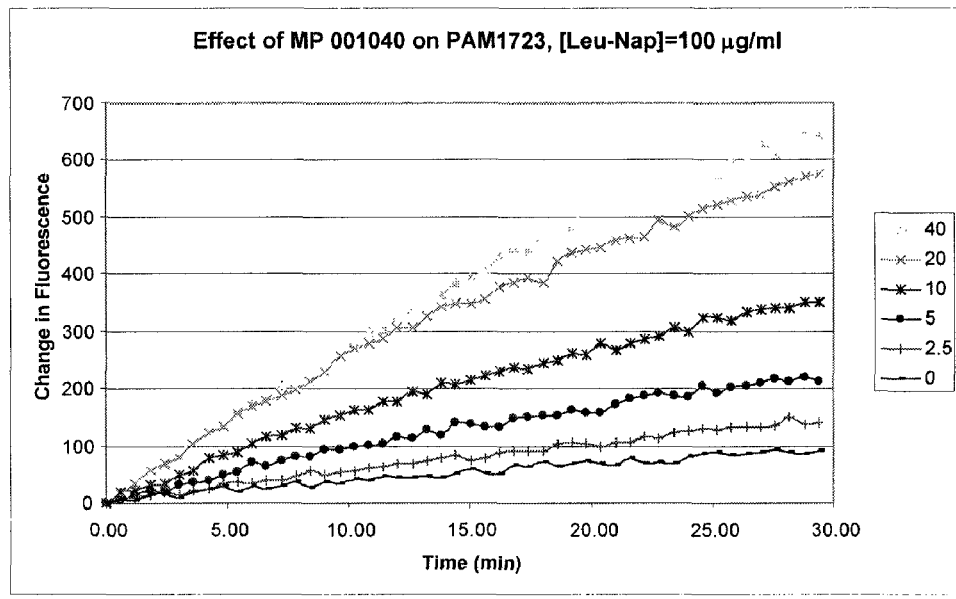
FIG. 10C depicts inhibition Leu-Nap efflux from PAM1723 by Dibromopropamidine.
Figure 10D:
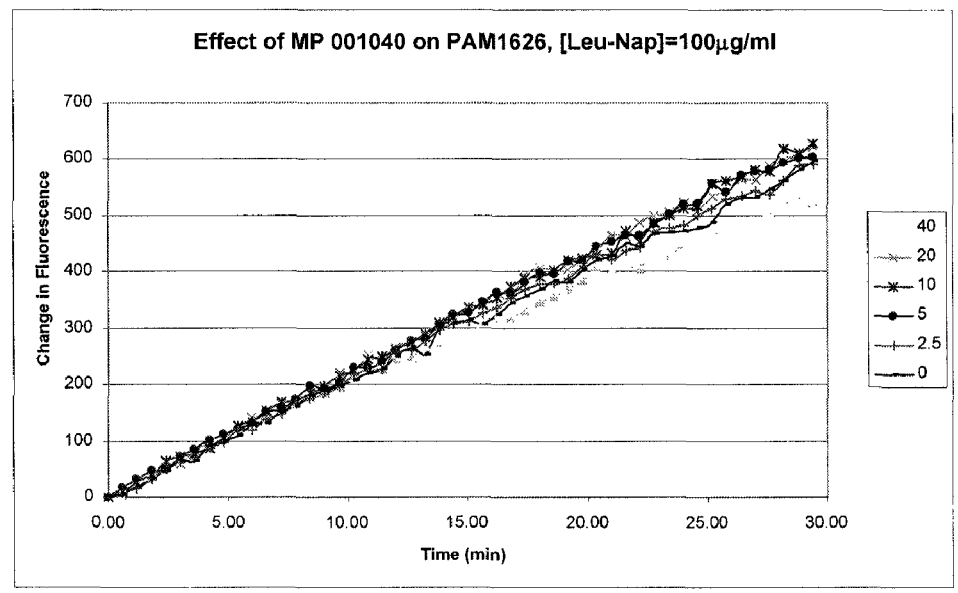
FIG. 10D depicts inhibition Leu-Nap efflux from PAM1626 by Dibromopropamidine.
Figure 10E:
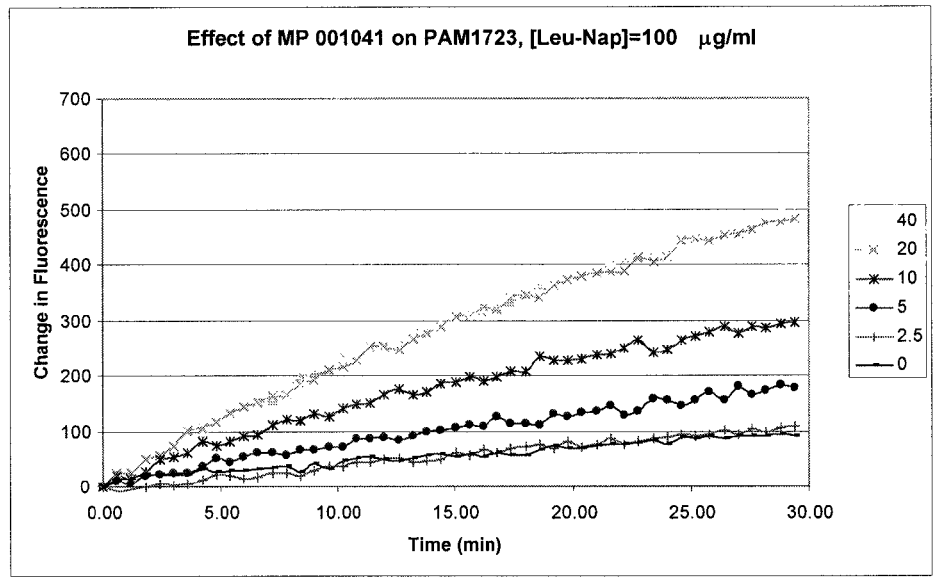
FIG. 10E depicts inhibition Leu-Nap efflux from PAM1723 by Hexamidine.
Figure 10F:
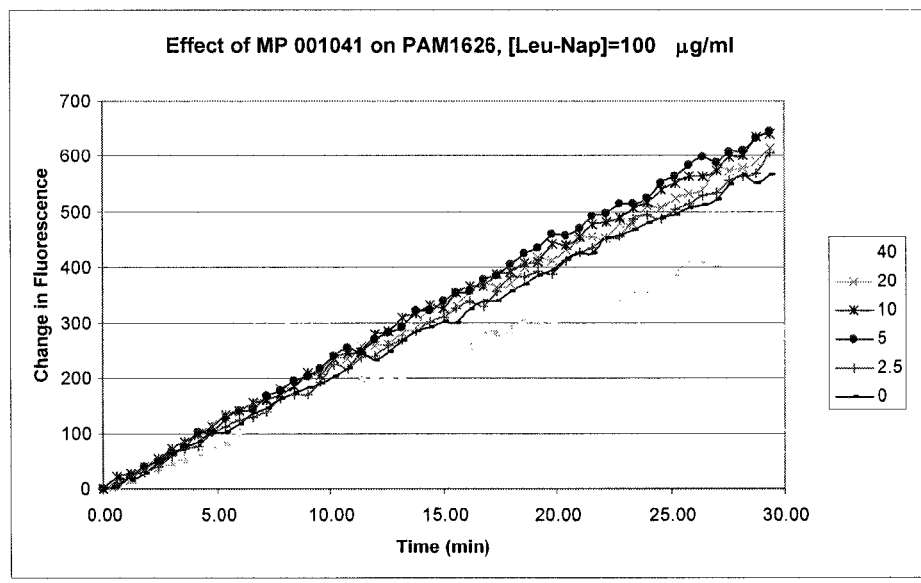
FIG. 10F depicts inhibition Leu-Nap efflux from PAM1626 by Hexamidine.

Efflux pump inhibitory activity of propamidine, dibromopropamidine, and hexamidine was confirmed in Leu-Nap accumulation assays. The uptake of Leu-Nap (100 µg/ml) by PAM1723 (FIGS. 10A, C, and E) or PAM1626 (FIGS. 10B, D, and F) cells was studied in the presence of various concentrations of propamidine (0 µg/ml to 160 µg/ml), dibromopropamidine (0 to µg/ml to 40 µg/ml), and hexamidine (0 µg/ml to 40 µg/ml), respectively. All three compounds were capable of completely inhibiting the MexAB-OprM-mediated efflux of Leu-Nap from the strain overexpressing this pump. The rate of Leu-NAp uptake into PAM1626 and PAM1723 in the presence of 160 µg/ml propamidine, 20 µg/ml of dibromoproapmidine, and 20 µg/ml of hexamidine was the same.

Example 13

Efflux Pump Inhibitory Activity of Diamidine Analogs

Efflux pump inhibitory activity of several commercially available diamidine analogs was evaluated using the checkerboard assay of Example 1 against the strain of *P. aeruginosa* overexpressing the MexAB-OprM efflux pump. Two compounds with measurable efflux pump inhibitory activity are shown in Table 6.

TABLE 6

Potentiation of levofloxacin by diamidine analogs relative to pentamidine against
the strain of *P. aeruginosa*, PAM1723, expressing the MexAB-OprM efflux pump.

| Compound | MIC* (μg/ml) | Levofloxacin MIC (μg/ml) in the presence of dimidines (μg/ml) | | | | | | | |
|---|---|---|---|---|---|---|---|---|---|
| | | 0 | 1.25 | 2.5 | 5 | 10 | 20 | 40 | 80 |
| Pentamidine MP 601205 | >81 | 2 | 2 | 1 | 1 | 1 | 0.25 | 0.06 | 0.007 |
| MP 601206 | 80 | 2 | 2 | 2 | 1 | 1 | 0.5 | 0.06 | NG |
| MP 601319 | >80 | 2 | 2 | 2 | 2 | 2 | 1 | 0.25 | 0.125 |

Example 14

Synergistic Antibacterial Effect of Propamidine in Combination with Quinolone Antibiotics Against Ophthalmic *P. aeruginosa*

Ophthalmic clinical isolates were obtained from patients suffering from *Pseudomonas aeruginosa* eye infections. Overnight cultures of the isolated *P. aeruginosa* strains were diluted 1/1000 in Mueller-Hinton Broth (MHB), allowed to grow to $OD_{600}$~0.3, and diluted 4-fold with fresh MHB containing various concentrations of quinolone antibiotics alone or in combination with a propamidine for 24 hours. After 24 hours, the minimum inhibitor concentrations were determined. Results are shown in Table 7.

TABLE 7

Antibacterial activity of propamidine in combination with quinolone antibiotics.

| Strain | 0 | 1.25 | 2.5 | 5 | 10 | 20 | 40 | 80 |
|---|---|---|---|---|---|---|---|---|
| Levofloxacin MIC (mg/l) in the presence of Propamidine (mg/l) | | | | | | | | |
| 1 | 64 | 64 | 64 | 64 | 32 | 16 | 8 | NG |
| 2 | 32 | 32 | 32 | 32 | 16 | 16 | 8 | NG |
| 3 | 8 | 8 | 8 | 8 | 4 | 1 | NG | NG |
| Gatifloxacin MIC (mg/l) in the presence of Propamidine (mg/l) | | | | | | | | |
| 1 | 64 | 64 | 64 | 32 | 32 | 16 | 8 | NG |
| 2 | 32 | 32 | 32 | 16 | 16 | 8 | 4 | NG |
| 3 | 8 | 8 | 8 | 4 | 2 | 0.5 | NG | NG |

TABLE 7-continued

Antibacterial activity of propamidine in combination with quinolone antibiotics.

| Strain | 0 | 1.25 | 2.5 | 5 | 10 | 20 | 40 | 80 |
|---|---|---|---|---|---|---|---|---|
| Moxifloxacin MIC (mg/l) in the presence of Propamidine (mg/l) | | | | | | | | |
| 1 | 64 | 64 | 64 | 64 | 32 | 32 | 8 | NG |
| 2 | 64 | 64 | 64 | 64 | 32 | 32 | 16 | NG |
| 3 | 16 | 16 | 16 | 16 | 8 | 2 | NG | NG |
| Clinafloxacin MIC (mg/l) in the presence of Propamidine (mg/l) | | | | | | | | |
| 1 | 4 | 4 | 4 | 4 | 2 | 1 | 0.5 | NG |
| 2 | 2 | 2 | 2 | 2 | 1 | 1 | 0.25 | NG |
| 3 | 1 | 0.5 | 0.5 | 0.5 | 0.25 | £0.125 | NG | NG |
| Tosufloxacin MIC (mg/l) in the presence of Propamidine (mg/l) | | | | | | | | |
| 1 | >32 | >32 | >32 | >32 | >32 | >32 | 4 | NG |
| 2 | >128 | >128 | >128 | >128 | >128 | >128 | 4 | NG |
| 3 | >128 | >128 | >128 | >128 | 4 | 1 | NG | NG |

Example 15

In Vivo Antibacterial Activity of Gatifloxacin in Combination with Propamidine Against Ophthalmic *P. aeruginosa*

Studies were conducted to compare the combination of an EPI and gatifloxacin in a rabbit model of keratitis caused by ophthalmic *P. aeruginosa* isolate strain 3, which was found to have elevated MICs to fluoroquinolones due to efflux pumps. Rabbits were treated with gatifloxacin alone or a combination of gatifloxacin and propamidine for 8 hours. Treatment with 0.3% gatifloxacin alone produced 0.28 logs of bacterial killing while the combination of 0.3% gatifloxacin and 0.5% propamidine produced 2.51 logs of bacterial killing. These results suggest that the efficacy of the combination is superior to the antibiotic alone.

A clinical isolate of gatifloxacin-resistant *Pseudomonas aeruginosa* (isolate strain 3, MIC: Gatifloxacin 8 μg/ml) was subcultured on 5% sheep blood agar and incubated at 37° C. in 6% $CO_2$ overnight. The next morning, a colony of the PA strain was suspended in 5 ml of sterile trypticase soy broth and allowed to incubate at 37° C. in 6% $CO_2$ for 4 hours. After incubation, the absorbance of the bacterial suspension was measured at 650 nm using a spectrophotometer. The bacterial suspension was diluted in sterile trypticase soy broth to provide an inoculum of approximately 1,000 ($1.0 \times 10^3$) cfu/eye in 25 μl.

Rabbits were anesthetized by intramuscular injections of ketamine & xylazine and topical anesthesia with proparacaine. Rabbits were inoculated intrastromally with 25 μl of the bacterial inocula. After 16 hours, rabbits were divided into groups and were administered nineteen drops of test medicament in solution (prepared in 0.9% saline) over 8 hours. One hour after the final treatment, rabbits were sacrificed and large 9.5 mm buttons were removed from the corneas. The buttons were homogenized and plated to determine colony counts.

Figure 11:
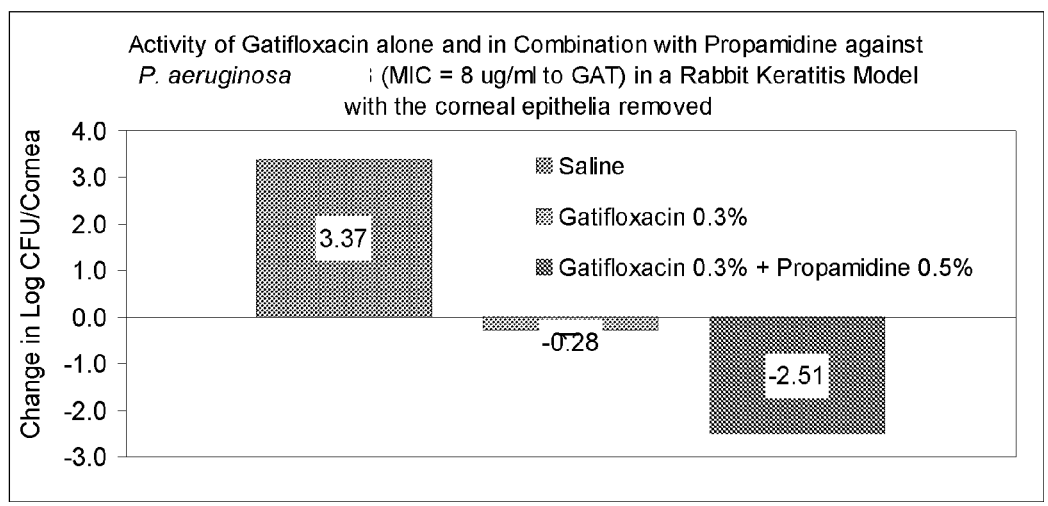
FIG. 11 is a bar chart illustrating the antibacterial activity of gatifloxacin alone and in combination with propamidine.

Treatment with 0.3% gatifloxacin alone produced 0.28 logs of bacterial killing while the combination of 0.3% gatifloxacin and 0.5% propamidine produced 2.51 logs of bacterial killing. The results are illustrated in FIG. 11.

Example 16

Synergistic Antibacterial Effect of Various Diamidines in Combination with Quinolone Antibiotics An overnight culture of *P. aeruginosa* was diluted 1/1000 in Mueller-Hinton Broth (MHB), allowed to grow to $OD_{600}$~0.3, diluted 4-fold with fresh MHB containing various concentrations of levofloxacin or moxifloxacin alone or in combination fixed concentrations of various diamidine EPIs for 24 hours. After 24 hours, the minimum inhibitor concentrations were determined, results are shown in Table 8.

nolone are placed in the outer ear of the rat using an ear dropper. The following combinations are tested: propamidine with ciprofloxacin, gatifloxacin, levofloxacin, moxifloxacin, clinafloxacin, tosufloxacin, and ofloxacin; dibromopropamidine with ciprofloxacin, gatifloxacin, levofloxacin, moxifloxacin, clinafloxacin, tosufloxacin, and ofloxacin; and hexamidine with ciprofloxacin, gatifloxacin, levofloxacin, moxifloxacin, clinafloxacin, tosufloxacin, and ofloxacin. Solutions containing 0.1-1.5% fluoroquinolone alone are administered to a separate set of rats as a control. The progression of the otitis externa infection is monitored by visual inspection of the outer ear and by determining bacterial counts over 20 days. The results indicate that the various combinations of diamidine with fluoroquinolone reduce the extent of infection when compared to administration of fluoroquinolone alone.

All references cited herein are incorporated herein by reference in their entirety. To the extent publications and patents or patent applications incorporated by reference contradict the disclosure contained in the specification, the specification is intended to supersede and/or take precedence over any such contradictory material.

All numbers expressing quantities of ingredients, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

Many modifications and variations of this invention can be made without departing from its spirit and scope, as will be apparent to those skilled in the art. The specific embodiments described herein are offered by way of example only and are not meant to be limiting in any way. It is intended that the specification and examples be considered as exemplary only.

TABLE 8

Antibacterial activity of diamidines in combination with quinolone antibiotics.

| | *P. aeruginosa* PAM 1723 (MexAB-OprM overexpressed) MIC of antibiotics (mg/l) in the presence of the EPI | | | | |
|---|---|---|---|---|---|
| Antibiotic | No EPI | Pentamidine (20 mg/l) | Propamidine (10 mg/l) | Dibromopropamidine (10 mg/l) | Hexamidine (10 mg/l) |
| Levofloxacin | 2 | 0.125 | 0.5 | 0.125 | 0.125 |
| Moxifloxacin | 4 | 0.25 | 1 | 0.125 | 0.25 |

Example 17

Antibacterial Effect of Diamidines in Combination with Fluoroquinolones in a Rat Model of Otitis Externa A rat model of otitis externa infection is generated by anesthetizing the rats and mechanically irritating the external ear canal with a plastic cone while taking care not to induce an ulcer or bleeding. One minute after irritating the canal, the site is infected by applying 0.1 mL of a *P. aeruginosa* suspension. After the infection has taken hold, drops of a solution containing 0.1-1.5% diamidine and 0.1-1.5% fluoroqui-

What is claimed is:

1. A method of therapeutic treatment of a gram negative bacterial infection in an eye or ear of a subject, comprising co-administering to the eye or ear infected with a gram negative bacteria having an efflux pump an effective amount of an antimicrobial agent and a compound of formula I:

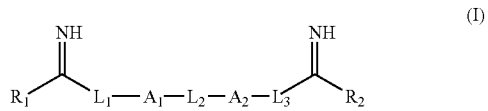

wherein R₁ and R₂ are separately selected from the group consisting of amine and $C_{1-4}$ alkylamine;

linkers $L_1$ and $L_3$ are separately selected from the group consisting of amine and $C_{1-2}$ alkylamine or are separately absent;

aromatic rings $A_1$ and $A_2$ are separately selected from the group consisting of

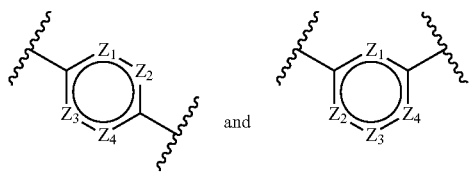

wherein $Z_1$-$Z_4$ are each C, with the proviso that aromaticity of the aromatic rings are maintained;

$Z_1$-$Z_4$ that are C are optionally substituted with $C_{1-4}$ alkyl, $CH_2NH_2$, halogen, methoxy, $CH_2C(O)NMe_2$, $C(O)NH_2$, $C(O)NMe_2$, $SO_2Me$, or $SO_2NH_2$;

linker $L_2$ is a 1 to 12 unit chain, wherein each units is independently selected from the group consisting of $CH_2$, $C(CH_3)_2$, O, C(O), S, S(O), $S(O)_2$, NH, $NR_4$, phenyl, monocyclic 5-membered heteroaryl, monocyclic 6-membered heteroaryl, —CH=CH— cis, —CH=CH— trans, NHC(O)NH, $NR_4$C(O)NH, NHC(O)$NR_4$, $NR_4$C(O)$NR_4$, OC(O)NH, $NR_4$C(O)O, OC(O)$NR_4$, and NHC(O)O with the proviso that $L_2$ does not contain a C(O)NH, C(O)$NR_4$, C(O)O, or C(O)S unit;

wherein the 5-membered heteroaryls are selected from the group consisting of imidazole, furane, thiophene, thiazole, isothiazole, oxazole, isoxazole, 1,2,3-oxadiazole, 1,3,4-oxadiazole, 1,2,4-oxadiazole, 1,2,3-triazole, and 1,3,4-triazole;

the 6-membered heteroaryls are selected from the group consisting of pyridine, pyrimidine, pyridazine, 1,2,4-triazine, and 1,3,5-triazine; and $R_4$ is selected from the group consisting of H and $C_{1-4}$ alkyl.

2. The method of claim 1, wherein the microbial infection is infection with one or more organisms selected from the group consisting of *Pseudomonas aeruginosa, Pseudomonas fluorescens, Pseudomonas acidovorans, Pseudomonas alcaligenes, Pseudomonas putida, Stenotrophomonas maltophilia, Burkholderia cepacia, Aeromonas hydrophilia, Escherichia coli, Citrobacter freundii, Salmonella typhimurium, Salmonella typhi, Salmonella paratyphi, Salmonella enteritidis, Shigella dysenteriae, Shigella flexneri, Shigella sonnei, Enterobacter cloacae, Enterobacter aerogenes, Klebsiella pneumoniae, Klebsiella oxytoca, Serratia marcescens, Francisella tularensis, Morganella morganii, Proteus mirabilis, Proteus vulgaris, Providencia alcalifaciens, Providencia rettgeri, Providencia stuartii, Acinetobacter calcoaceticus, Acinetobacter haemolyticus, Yersinia enterocolitica, Yersinia pestis, Yersinia pseudotuberculosis, Yersinia intermedia, Bordetella pertussis, Bordetella parapertussis, Bordetella bronchiseptica, Haemophilus influenzae, Haemophilus parainfluenzae, Haemophilus haemolyticus, Haemophilus parahaemolyticus, Haemophilus ducreyi, Pasteurella multocida, Pasteurella haemolytica, Branhamella catarrhalis, Helicobacter pylori, Campylobacter fetus, Campylobacter jejuni, Campylobacter coli, Borrelia burgdorferi, Vibrio cholerae, Vibrio parahaemolyticus, Legionella pneumophila, Listeria monocytogenes, Neisseria gonorrhoeae, Neisseria meningitidis, Kingella, Moraxella, Gardnerella vaginalis, Bacteroides fragilis, Bacteroides distasonis, Bacteroides 3452A homology group, Bacteroides vulgatus, Bacteroides ovalus, Bacteroides thetaiotaomicron, Bacteroides uniformis, Bacteroides eggerthii*, and *Bacteroides splanchnicus*.

3. The method of claim 1, wherein the infection is one or more of otitis media, otitis externa, malignant otitis externa, and mastoiditis.

4. The method of claim 1, wherein the infection is ophthalmic *Pseudomonas aeruginosa*.

5. The method of claim 1, wherein the compound of formula I is selected from the group consisting of propamidine, pentamidine, hexamidine, dibromopropamidine,

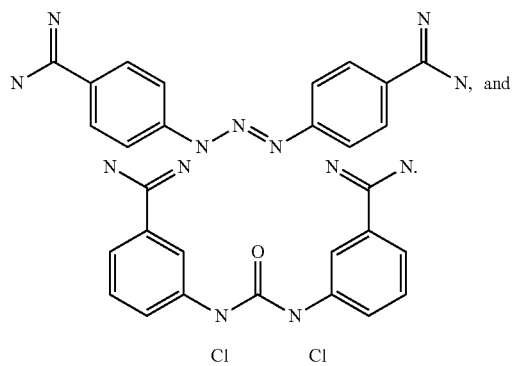

6. The method of claim 1, wherein the co-administration comprises administering a pharmaceutical composition that comprises both the compound of formula I and the antimicrobial agent to the eye or ear.

7. The method of claim 1, wherein the co-administration comprises topically administering the compound of formula I and the antimicrobial agent to the eye or ear.

8. The method of claim 1, wherein the co-administration comprises injecting the compound of formula I and the antimicrobial agent into the eye.

9. The method of claim 1, wherein the compound of formula I and the antimicrobial agent are administered simultaneously.

10. The method of claim 1, wherein the compound of formula I and the antimicrobial agent are administered sequentially.

11. A method for reducing the onset of a gram negative bacterial infection in an eye or ear of a subject, comprising co-administering to an eye or ear at risk of infection with a gram negative bacteria having an efflux pump an effective amount of an antimicrobial agent and a compound of formula I:

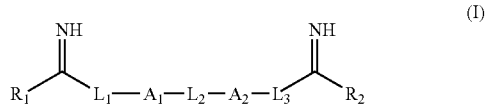

wherein R₁ and R₂ are separately selected from the group consisting of amine and $C_{1-4}$ alkylamine;

linkers $L_1$ and $L_3$ are separately selected from the group consisting of amine and $C_{1-2}$ alkylamine or are separately absent;

aromatic rings $A_1$ and $A_2$ are separately selected from the group consisting of

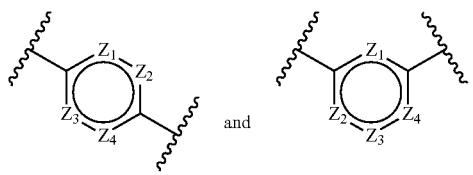

and wherein $Z_1$-$Z_4$ are each C, with the proviso that aromaticity of the aromatic rings are maintained;

$Z_1$-$Z_4$ that are C are optionally substituted with $C_{1-4}$ alkyl, $CH_2NH_2$, halogen, methoxy, $CH_2C(O)NMe_2$, $C(O)NH_2$, $C(O)NMe_2$, $SO_2Me$, or $SO_2NH_2$;

linker $L_2$ is a 1 to 12 unit chain, wherein each unit is independently selected from the group consisting of $CH_2$, $C(CH_3)_2$, O, C(O), S, S(O), $S(O)_2$, NH, $NR_4$, =N—, phenyl, monocyclic 5-membered heteroaryl, monocyclic 6-membered heteroaryl, —CH=CH— cis, —CH=CH— trans, NHC(O)NH, $NR_4$C(O)NH, NHC(O)$NR_4$, $NR_4$C(O)$NR_4$, OC(O)NH, $NR_4$C(O)O, OC(O)$NR_4$, and NHC(O)O with the proviso that $L_2$ does not contain a C(O)NH, C(O)$NR_4$, C(O)O, or C(O)S unit;

wherein the 5-membered heteroaryls are selected from the group consisting of imidazole, furane, thiophene, thiazole, isothiazole, oxazole, isoxazole, 1,2,3-oxadiazole, 1,3,4-oxadiazole, 1,2,4-oxadiazole, 1,2,3-triazole, and 1,3,4-triazole;

the 6-membered heteroaryls are selected from the group consisting of pyridine, pyrimidine, pyridazine, 1,2,4-triazine, and 1,3,5-triazine; and $R_4$ is selected from the group consisting of H and $C_{1-4}$ alkyl.

12. The method of claim 11, wherein the compound of formula I is selected from the group consisting of propamidine, pentamidine, hexamidine, dibromopropamidine,

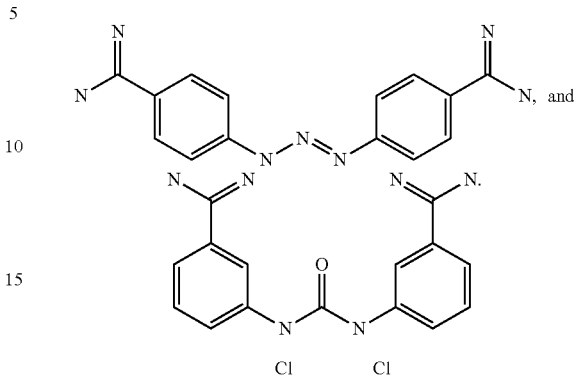

13. The method of claim 11, wherein the co-administration comprises administering a pharmaceutical composition that comprises both the compound of formula I and the antimicrobial agent to the eye or ear.

14. The method of claim 11, wherein the co-administration comprises topically administering the compound of formula I and the antimicrobial agent to the eye or ear.

15. The method of claim 11, wherein the co-administration comprises injecting the compound of formula I and the antimicrobial agent into the eye.

16. The method of claim 11, wherein the compound of formula I and the antimicrobial agent are administered simultaneously.

17. The method of claim 11, wherein the compound of formula I and the antimicrobial agent are administered sequentially.

* * * * *

UNITED STATES PATENT AND TRADEMARK OFFICE
CERTIFICATE OF CORRECTION

PATENT NO. : 7,994,225 B2
APPLICATION NO. : 11/856657
DATED : August 9, 2011
INVENTOR(S) : Bostian et al.

It is certified that error appears in the above-identified patent and that said Letters Patent is hereby corrected as shown below:

At column 8, line 29, please delete "*typhimrium*" and insert therefore --*typhimurium*--.

At column 17, line 22, please delete "1231" and insert therefore --123I--.

At column 25, line 10, please delete " 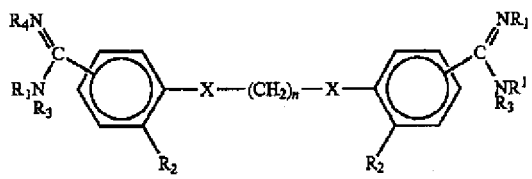 " and insert therefore -- 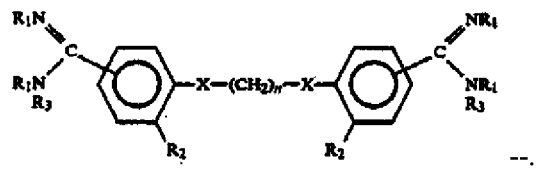 --.

At column 25, line 40, please delete " 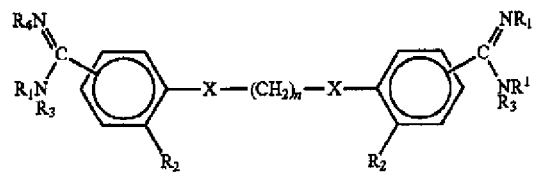 " and insert therefore -- 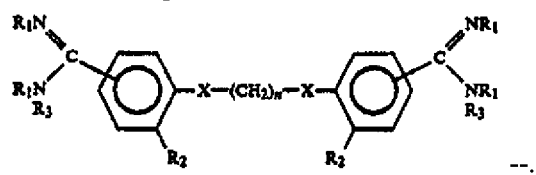 --.

At column 26, line 10, please delete " 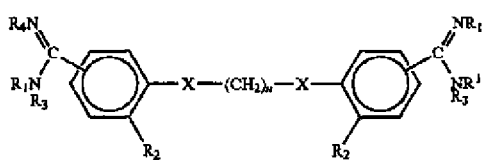 " and insert

Signed and Sealed this
Twelfth Day of March, 2013

Teresa Stanek Rea
*Acting Director of the United States Patent and Trademark Office*

CERTIFICATE OF CORRECTION (continued)

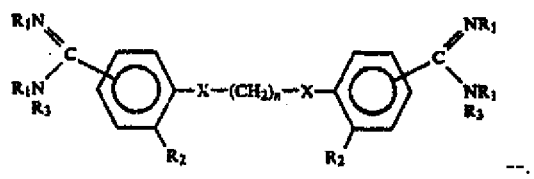

therefore --                                                                            --.

At column 36, line 29, please delete "(I)" and insert therefore --(i)--.

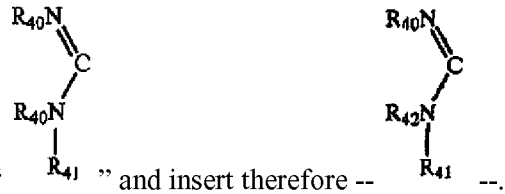

At column 38, line 7, please delete " " and insert therefore -- --.

At column 45, line 62, please delete "H2" and insert therefore --$H_2$--.

At column 51, line 4, please delete "$(CH_2)_m(C_6H_3)R^7$, $(CH_2)_m(C_6H_3)R^{2}$" and insert therefore --$(CH_2)_m(C_6H_3)R^{17}$, $(CH_2)_m(C_6H_3)R^{20}$--.

At column 51, line 5, please delete "$R^7$" and insert therefore --$R^{17}$--.

At column 51, line 6, please delete "$CONHCHRR^{21}$" and insert therefore --$CONHCHR^{20}R^{21}$--.

At column 57, line 14, please delete "µl" and insert therefore --A1--.

At column 57, line 25, please delete " 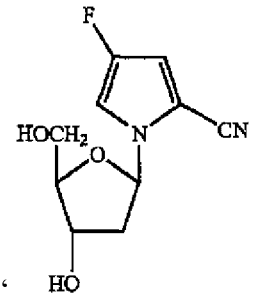 " and insert therefore

-- 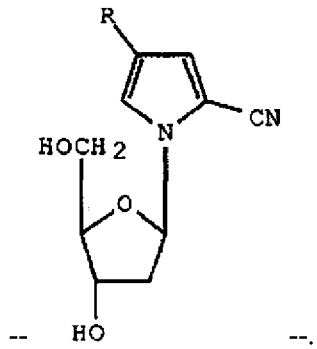 --.

At column 59, line 67, please delete "XI" and insert therefore --X1--.

CERTIFICATE OF CORRECTION (continued)

At column 60, line 5, delete " 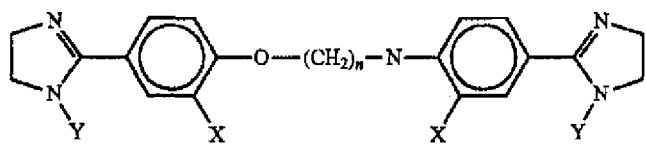 " and insert therefore -- 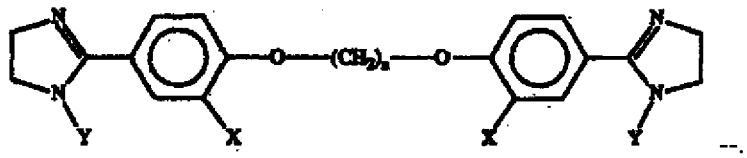 --.

At column 63-64, last row of chemical structures, please delete

" 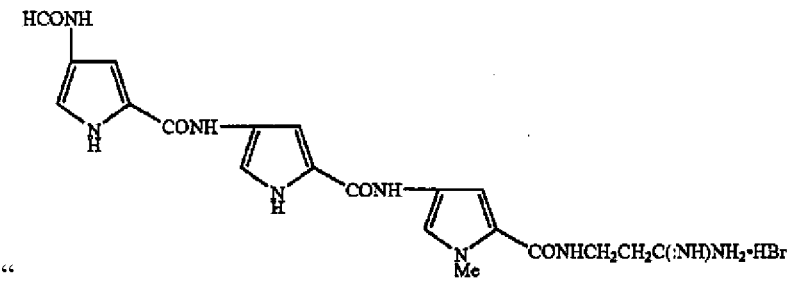 " and insert therefore

-- 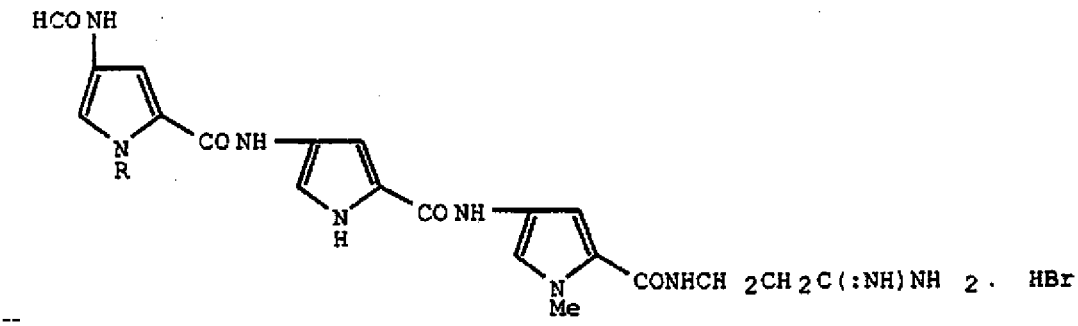 --.

At column 71, line 23, please delete "$X^1$=O. H" and insert therefore --$X^1$=O, H--.

At column 83, line 18, please delete "*ilcerans*" and insert therefore --*ulcerans*--.

At column 87, line 38, please delete "external malignant otitis external" and insert therefore --externa, malignant otitis externa,--.

At column 90, line 48, please delete ""Opthalmologica" and insert therefore --Ophthalmologica--.

At column 92, line 64, please delete "(UPC, UPC-SL, and UPC-L)" and insert therefore --(HPC, HPC-SL, and HPC-L)--.

At column 92, line 65, please delete "(UPMC)" and insert --(HPMC)--.

At column 93, line 24, please delete "(CH.sub.20H).sub.2" and insert therefore

CERTIFICATE OF CORRECTION (continued)
U.S. Pat. No. 7,994,225 B2

--(CH$_2$OH)$_2$--.

At column 105, line 26, please delete "g/ml)" and insert therefore --µg/ml)--.

At column 113, line 23 in Claim 1, please delete "units" and insert therefore --unit--.

At column 113, line 25 in Claim 1, after "NR$_4$," please insert --=N-,--.